(12) United States Patent
Schohe-Loop et al.

(10) Patent No.: US 7,320,977 B2
(45) Date of Patent: Jan. 22, 2008

(54) SUBSTITUTED 2-PHENYL-3(2H)-PYRIDAZINONES

(75) Inventors: Rudolf Schohe-Loop, Wuppertal (DE);
Elmar Burchardt, Wuppertal (DE);
Christiane Faeste, Oslo (NO); Claudia Hirth-Dietrich, Wuppertal (DE); Jörg Keldenich, Wuppertal (DE); Andreas Knorr, Erkrath (DE); Thomas Lampe, Düsseldorf (DE); Paul Naab, Wuppertal (DE); Delf Schmidt, Wuppertal (DE); Gunter Schmidt, Wuppertal (DE)

(73) Assignee: Bayer Healthcare AG, Leverkusen (DE)

( * ) Notice: Subject to any disclaimer, the term of this patent is extended or adjusted under 35 U.S.C. 154(b) by 305 days.

(21) Appl. No.: 10/511,225

(22) PCT Filed: Apr. 8, 2003

(86) PCT No.: PCT/EP03/03628

§ 371 (c)(1),
(2), (4) Date: Jul. 11, 2005

(87) PCT Pub. No.: WO03/097612

PCT Pub. Date: Nov. 27, 2003

(65) Prior Publication Data

US 2006/0004015 A1    Jan. 5, 2006

(30) Foreign Application Priority Data

Apr. 12, 2002  (DE)  ................. 102 16 144

(51) Int. Cl.
*C07D 403/04*  (2006.01)
*A61K 31/501*  (2006.01)

(52) U.S. Cl. .................... 514/252.02; 514/252.03; 514/227.8; 544/58.2; 544/114; 544/238

(58) Field of Classification Search ............... 544/238, 544/58.2, 114; 514/252.02, 252.03, 227.8, 514/236.5

See application file for complete search history.

(56) References Cited

U.S. PATENT DOCUMENTS 6,307,047 B1 * 10/2001 Black et al. ................ 544/240

OTHER PUBLICATIONS

Patent Abstracts of Japan, vol. 14 (485), Oct. 23, 1990 and JP 02200634A (Aug. 8, 1990).

* cited by examiner

*Primary Examiner*—Kahsay Habte

(57) ABSTRACT

The invention relates to substituted 2-Phenyl-3(2H)-Pyridazinones, to a method for the production thereof, and to their use as medicaments for the prophylaxis and/or treatment of diseases in humans and/or animals.

6 Claims, No Drawings

SUBSTITUTED 2-PHENYL-3(2H)-PYRIDAZINONES

The invention relates to novel substituted 2-phenyl-3(2H)-pyridazinone derivatives, to processes for their preparation and to their use for producing medicaments, in particular for controlling fibrotic disorders.

Lysyl oxidase is a copper-dependent amine oxidase (EC 1.4.3.13) which oxidatively deaminates the peptidyl-lysine residues in collagen and elastin molecules [H. M. Kagan, Lysyloxidase: Mechanism, regulation and relationship to liver fibrosis, *Path. Res. Pract.* 190, 910-919 (1994)]. This results in the formation of stable covalent linkages of tropocollagen or tropoelastin, which makes the assembly of stable collagen fibers from tropocollagen possible.

Lysyl oxidase plays a key role in disorders in which there is an increased deposition of collagen in the interstitial space. There is a many-fold increase in the activity of lysyl oxidase in patients with increased interstitial collagen deposition compared with a normal healthy population [R. C. Siegel, K. H. Chen, J. S. Greenspan, J. M. Aguiar, Biochemical and immunochemical study of lysyl oxidase experimental hepatic fibrosis in the rat, *Proc. Natl. Acad. Sci. USA* 75, 2945-2949 (1978); A. Konishi, H. Iguchi, J. Ochi, R. Kinoshita, K. Miura, H. Uchino, Increased lysyl oxidase in culture-medium of non-parenchymal cells from fibrotic livers, *Gastroenterol.* 89, 709-715 (1985)]. There was a measurable increase in the lysyl oxidase concentration in the serum from such patients [Y. Murawaki, Y. Kusakabe, C. Hirayama, Serum lysyl oxidase activity in chronic liver disease in comparison with serum levels of prolyl hydroxylase and laminin, *Hepatol.* 14, 1167-1173 (1991)]. In addition, it was possible to show in-animal-models [S. Ricard-Blum, G. Ville, J. A. Grimaud, Hepatic pyridoline level in murine schistosomiasis, in: *Molecular and cell biology of liver fibrogenesis*, edited by A. M. Gressner and G. Ramadori, Kluwer Academic Publishers, Dordrecht, 1992] and in patients [S. Ricard-Blum, S. Bresson-Hadni, D. A. Vuitton, G. Ville, J. A. Grimaud, Hydroxypyridinium collagen crosslinks in human liver fibrosis: a study of alveolar echinococcosis, *Hepatol.* 15, 599-602 (1992); A. Hayasaka, S. Iida, N. Suzuki, F. Kondo, M. Miyazaki, H. Yonemitsu, Pyridinolone collagen cross-links in patients with chronic viral hepatitis and cirrhosis, *J. Hepatol.* 24, 692-698 (1996)] that reaction products of lysyl oxidase, the dipyridinium crosslinks, are detectable in greatly increased concentrations in fibrotic tissues. It was shown that the degradability of deposited collagen depends on the degree of collagen crosslinking. Collagen with less crosslinking is more rapidly degraded by collagenase than is collagen with a high degree of crosslinking [C. A. Vater, E. D. Harris, R. C. Siegel, Native crosslinks in collagen fibrils induce resistance to human human synovial collagenase, *Biochem. J.* 181, 639-645 (1979)].

Lysyl oxidase thus has a key role in the formation of pathological collagen deposits through reducing the degradability of collagen fibers. Inhibition of lysyl oxidase activity thus leads to increased collagen degradation, so that the typical fibrotic tissue transformation can be prevented by inhibitors of lysyl oxidase.

It is an object of the present invention to provide medicaments for the prophylaxis and/or treatment of fibrotic disorders.

The object of the present invention is achieved by compounds of the formula (I), which act as lysyl oxidase inhibitors.

Structurally similar compounds are known for other indications and with different mechanisms of action. Thus, 4-ethoxy-2-methyl-5-morpholino-3(2H)-pyridazinone is described as non-steroidal analgesic and as antiinflammatory active substance [*J. Med. Chem.* 22, 53 (1979); Jpn. Kokai Tokkyo Koho JP 02200634]. An effect of 5-(4-methylsulfonylphenyl)pyridazinones as selective COX-2 inhibitors is described; they are suitable for controlling inflammatory or cyclooxygenase-mediated processes such as asthma or arthritis (WO-A-98/41511).

The present invention relates to compounds formula (I)

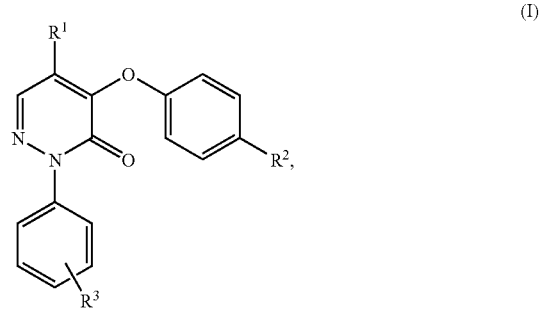

in which $R^1$ is 5- to 7-membered, saturated or partially unsaturated heterocyclyl which is linked via a ring nitrogen atom and optionally has a further heteroatom or hetero chain member from the series N, O, S, SO or $SO_2$, and which may be substituted once or twice, identically or differently, by substituents selected from the group of halogen, $(C_1-C_6)$-alkyl, $(C_2-C_6)$-alkenyl, $(C_3-C_8)$-cycloalkyl, hydroxy, oxo, carboxyl, $(C_1-C_6)$-alkoxycarbonyl, $(C_1-C_6)$-alkanoyl, $(C_3-C_8)$-cycloalkylcarbonyl, $(C_1-C_6)$-alkylsulfonyl, aminocarbonyl,

and $(C_1-C_6)$-alkylaminocarbonyl,
where $(C_1-C_6)$-alkyl and $(C_1-C_6)$-alkanoyl in turn may each be substituted by halogen, hydroxy, $(C_1-C_4)$-alkoxy, $(C_1-C_4)$-alkoxycarbonyl, amino, mono- or di-$(C_1-C_4)$-alkylamino, $(C_1-C_4)$-alkoxycarbonylamino or 5- or 6-membered heterocyclyl having up to two heteroatoms from the series N, O and/or S, or $R^1$ is 5-membered heteroaryl which is linked via a ring nitrogen atom and has up to two further ring nitrogen atoms, and which may be substituted once to three times, identically or differently, by halogen, $(C_1-C_6)$-alkoxycarbonyl or $(C_1-C_6)$-alkyl which is in turn optionally substituted by hydroxy or halogen, $R^2$ is $(C_6-C_{10})$-aryl which may be substituted once or twice, identically or differently, by substituents selected from the group of halogen, nitro, cyano, $(C_1-C_6)$-alkyl, trifluoromethyl, $(C_1-C_6)$-alkanoyl, $(C_1-C_6)$-alkoxy, hydroxy, $(C_1-C_6)$-acyloxy, amino, $(C_1-C_6)$-acylamino, mono- and di-[$(C_1-C_6)$-alkylsulfonyl]amino,
where $(C_1-C_6)$-alkyl and $(C_1-C_6)$-alkoxy in turn may each be substituted by hydroxy, amino, $(C_1-C_4)$-alkoxy or $(C_1-C_4)$-acylamino, or R² is 5- or 6-membered heteroaryl which has up to two ring nitrogen atoms and which may be substituted by amino, hydroxy, halogen, ($C_1$-$C_6$)-alkyl or ($C_1$-$C_6$)-alkoxy, and R³ is hydrogen, halogen, ($C_1$-$C_6$)-alkyl, trifluoromethyl, nitro, cyano, carboxyl or ($C_1$-$C_6$)-alkoxycarbonyl.

The compounds of the invention may also be present in the form of their salts, solvates or solvates of the salts.

The compounds of the invention may, depending on their structure, exist in stereoisomeric forms (enantiomers, diastereomers). The invention therefore relates to the enantiomers or diastereomers and respective mixtures thereof. The stereo-isomerically pure constituents can be isolated in a known manner from such mixtures of enantiomers and/or diastereomers.

The invention also relates, depending on the structure of the compounds, to tautomers of the compounds.

Salts preferred for the purposes of the invention are physiologically acceptable salts of the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Physiologically acceptable salts of the compounds of the invention also include salts of conventional bases, such as by way of example and preferably alkali metal salts (e.g. sodium and potassium salts), alkaline earth metal salts (e.g. calcium and magnesium salts) and ammonium salts derived from ammonia or organic amines having 1 to 16 C atoms, such as by way of example and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabiethylamine, arginine, lysine, ethylenediamine and methylpiperidine.

Solvates refers for the purposes of the invention to those forms of the compounds which form a complex in the solid or liquid state through coordination with solvent molecules. Hydrates are a specific form of solvates in which the coordination takes place with water.

For the purposes of the present invention, the substituents have the following meaning unless specified otherwise:

($C_1$-$C_6$)-alkanoyl is a straight-chain or branched alkanoyl radical having 1 to 6 carbon atoms. Examples which may be mentioned as preferred are: formyl, acetyl, propanoyl, butanoyl, isobutanoyl, pentanoyl, isopentanoyl and hexanoyl. A straight-chain or branched alkanoyl radical having 1 to 4 carbon atoms is preferred. Acetyl and propanoyl are particularly preferred.

($C_1$-$C_6$)- and ($C_1$-$C_4$)-alkyl are a straight-chain or branched alkyl radical having respectively 1 to 6 and 1 to 4 carbon atoms. Preference is given to a straight-chain or branched alkyl radical having 1 to 4, particularly preferably having 1 to 3, carbon atoms. Preferred examples which may be mentioned are: methyl, ethyl, n-propyl, isopropyl, tert-butyl, n-pentyl and n-hexyl.

($C_2$-$C_6$)- and ($C_2$-$C_4$)-alkenyl are a straight-chain or branched alkenyl radical having respectively 2 to 6 and 2 to 4 carbon atoms. Preference is given to a straight-chain or branched alkenyl radical having 2 to 4, particularly preferably having 2 to 3, carbon atoms. Preferred examples which may be mentioned are: vinyl, allyl, n-prop-1-en-1-yl and n-but-2-en-1-yl.

($C_1$-$C_6$)- and ($C_1$-$C_4$)-alkoxy are a straight-chain or branched alkoxy radical having respectively 1 to 6 and 1 to 4 carbon atoms. Preference is given to a straight-chain or branched alkoxy radical having 1 to 4, particularly preferably having 1 to 3, carbon atoms. Preferred examples which may be mentioned are: methoxy, ethoxy, n-propoxy, isopropoxy, tert-butoxy, n-pentoxy and n-hexoxy.

Mono-($C_1$-$C_6$)- and mono-($C_1$-$C_4$)-alkylamino are a straight-chain or branched monoalkylamino radical having respectively 1 to 6 and 1 to 4 carbon atoms. Preference is given to a straight-chain or branched alkylamino radical having 1 to 4, particularly preferably having 1 to 3, carbon atoms. Preferred examples which may be mentioned are: methylamino, ethylamino, n-propylamino, isopropylamino, tert-butylamino, n-pentylamino and n-hexylamino.

Di-($C_1$-$C_6$)- and di-($C_1$-$C_4$)-alkylamino are a straight-chain or branched dialkylamino radical, where the alkyl radicals may be identical or different and each respectively contains 1 to 6 and 1 to 4 carbon atoms. Preference is given to a straight-chain or branched dialkylamino radical in which the alkyl radicals each contain 1 to 4, particularly preferably 1 to 3, carbon atoms. Preferred examples which may be mentioned are: dimethylamino, diethylamino, di-n-propylamino, diisopropylamino, di-tert-butylamino, di-n-pentylamino, di-n-hexylamino, ethylmethylamino, isopropylmethylamino, n-butylmethylamino, tert-butylmethylamino, n-hexylisopentylamino.

($C_1$-$C_6$)- and ($C_1$-$C_4$)-alkoxycarbonyl is a straight-chain or branched alkoxycarbonyl radical having respectively 1 to 6 and 1 to 4 carbon atoms in the alkoxy group. Preferred examples which may be mentioned are: methoxycarbonyl, ethoxycarbonyl, n-propoxycarbonyl, isopropoxycarbonyl and tert-butoxycarbonyl.

($C_1$-$C_6$)- and ($C_1$-$C_4$)-alkylsulfonyl is a straight-chain or branched alkylsulfonyl radical having respectively 1 to 6 and 1 to 4 carbon atoms in the alkyl group. Preferred examples which may be mentioned are: methylsulfonyl, ethylsulfonyl, n-propylsulfonyl, isopropylsulfonyl and tert-butylsulfonyl.

($C_1$-$C_6$)-acyloxy is a straight-chain or branched alkyl radical which has 1 to 6 carbon atoms and which has in position 1 a doubly bonded oxygen atom and is linked in position 1 via a further oxygen atom. Preferred examples which may be mentioned are: acetoxy, propionoxy, n-butyroxy, i-butyroxy, pivaloyloxy, n-hexanoyloxy.

($C_1$-$C_6$)- and ($C_1$-$C_4$)-acylamino is an amino group having a straight-chain or branched alkanoyl substituent which has respectively 1 to 6 and 1 to 4 carbon atoms and is linked via the carbonyl group. Preferred examples which may be mentioned are: formamido, acetamido, propionamido, n-butyramido and pivaloylamido.

($C_1$-$C_6$)-alkylaminocarbonyl is an amino group which is linked via a carbonyl group and which has a straight-chain or branched alkyl substituent having 1 to 6 carbon atoms. An alkylaminocarbonyl radical having 1 to 4 carbon atoms is preferred. Preferred examples which may be mentioned are: methylaminocarbonyl, ethylaminocarbonyl, n-propylaminocarbonyl, isopropylaminocarbonyl and t-butylaminocarbonyl.

($C_1$-$C_4$)-alkoxycarbonylamino is an amino group having a straight-chain or branched alkoxycarbonyl substituent which has 1 to 4 carbon atoms in the alkoxy radical and is linked via the carbonyl group to the amino group. Preferred examples which may be mentioned are: methoxycarbonylamino, ethoxycarbonylamino, n-propoxycarbonylamino, isopropoxycarbonylamino and t-butoxycarbonylamino.

Mono- and di-[($C_1$-$C_6$)-alkylsulfonyl]amino is an amino group having respectively one and two identical or different, straight-chain or branched alkylsulfonyl substituents each having 1 to 6 carbon atoms in the alkyl group. Preferred examples which may be mentioned are: methylsulfonylamino, bis-(methylsulfonyl)amino, ethylsulfonylamino, n-propylsulfonylamino, isopropylsulfonylamino and tert-butylsulfonylamino.

($C_6$-$C_{10}$)-aryl is an aromatic radical having 6 to 10 carbon atoms. Preferred aryl radicals are phenyl and naphthyl.

($C_3$-$C_8$)-cycloalkyl is a cycloalkyl group having 3 to 8 carbon atoms. A cycloalkyl group having 3 to 6 carbon atoms is preferred. Preferred examples which may be mentioned are: cyclopropyl, cyclobutyl, cyclopentyl, cyclohexyl, cycloheptyl and cyclooctyl. Cyclopropyl, cyclopentyl and cyclohexyl are particularly preferred.

($C_3$-$C_8$)-cycloalkylcarbonyl is a cycloalkyl group as defined above which is linked via a carbonyl group. Cyclopropylcarbonyl is preferred.

5- or 6-membered heteroaryl is a heteroaromatic radical having respectively 1 to 3 or 1 to 2 ring nitrogen atoms which is linked via a ring carbon atom or, where appropriate, via a ring nitrogen atom. Preferred examples which may be mentioned are: pyrrolyl, imidazolyl, pyrazolyl, triazolyl, pyridyl, pyrimidinyl and pyridazinyl.

5- or 6-membered heterocyclyl having up to two heteroatoms from the series N, O and/or S is a saturated heterocycle. Preferred examples which may be mentioned are: pyrrolidinyl, piperazinyl, morpholinyl, thiomorpholinyl and piperidinyl. Piperazinyl is preferred.

5- to 7-membered, saturated or partially unsaturated heterocyclyl which is linked via a ring nitrogen atom is a nonaromatic heterocycle which, besides the nitrogen atom, may comprise a further heteroatom from the series N, O, S, SO or $SO_2$ and, where appropriate, one or two double bonds. A 5- to 6-membered saturated heterocycle which, besides the nitrogen atom, may comprise a further heteroatom from the series N, O or S is preferred. Preferred examples which may be mentioned are: pyrrolidinyl, pyrrolinyl, piperdinyl, 1,2-dihydropyridinyl, 1,4-dihydropyridinyl, piperazinyl, morpholinyl, thiomorpholinyl, hexahydroazepinyl and hexahydro-1,4-diazepinyl. Piperidinyl, piperazinyl, morpholinyl and pyrrolidinyl.

Halogen is fluorine, chlorine, bromine and iodine. Fluorine, chlorine and bromine are preferred. Fluorine and chlorine are particularly preferred.

Preferred compounds of the formula (I) are those in which
  $R^1$ is a group of the formula

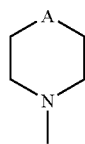

in which
  A is $CR^4R^5$, O, S, $NR^6$ or —$CH_2NR^6$—, where
    $R^4$ and $R^5$ are independently of one another hydrogen, ($C_1$-$C_4$)-alkyl, which may be substituted by hydroxy, or hydroxy, fluorine, carboxyl or ($C_1$-$C_4$)-alkoxycarbonyl, or together with the carbon atom to which they are bonded form a carbonyl group,
    and
    $R^6$ is hydrogen, ($C_2$-$C_4$)-alkenyl, ($C_3$-$C_6$)-cycloalkyl, ($C_1$-$C_4$)-alkoxycarbonyl, formyl, acetyl, ($C_3$-$C_6$)-cycloalkylcarbonyl, ($C_1$-$C_4$)-alkylsulfonyl, aminocarbonyl, ($C_1$-$C_4$)-alkylaminocarbonyl or is ($C_1$-$C_4$)-alkyl which in turn may be substituted by hydroxy, methoxy, ethoxy, ($C_1$-$C_4$)-alkoxycarbonyl, amino, dimethylamino, diethylamino, pyrrolidino, piperidino or morpholino, or
  $R^1$ is 5-membered heteroaryl which is linked via a ring nitrogen atom and has up to two further ring nitrogen atoms and which may be substituted once or twice, identically or differently, by fluorine, chlorine, ($C_1$-$C_4$)-alkoxycarbonyl or ($C_1$-$C_4$)-alkyl which in turn is optionally substituted by hydroxy,
  $R^2$ is phenyl which may be substituted once or twice, identically or differently, by substituents selected from the group of fluorine, chlorine, cyano, ($C_1$-$C_4$)-alkyl, trifluoromethyl, formyl, acetyl, ($C_1$-$C_4$)-alkoxy, hydroxy, acetoxy, pivaloyloxy, amino, formylamino, acetylamino and methylsulfonylamino,
    where ($C_1$-$C_4$)-alkyl and ($C_1$-$C_4$)-alkoxy in turn may each be substituted by hydroxy, amino, methoxy, ethoxy or acetylamino, or
  $R^2$ is pyrrolyl, pyridyl or pyrimidinyl, each of which may be substituted by amino, fluorine, chlorine, methyl, ethyl, methoxy or ethoxy, and
  $R^3$ is hydrogen, fluorine, chlorine, bromine, methyl, ethyl, trifluoromethyl, nitro or cyano.

Particularly important compounds of the formula (I) are those in which
  $R^1$ is an imidazolyl which is attached via a ring nitrogen atom or is a piperazinyl which is attached via a ring nitrogen atom and which may be substituted on the second ring nitrogen atom by methyl, ethyl, 2-hydroxyethyl, 2-methoxyethyl, acetyl, tert-butoxycarbonyl, cyclopropylcarbonyl, aminocarbonyl or methylsulfonyl.

Likewise particularly important compounds of the formula (I) are those in which
  $R^2$ is phenyl which may be substituted by hydroxy or fluorine or is pyridyl.

Very particularly preferred compounds of the formula (I) are those in which
  $R^1$ is imidazolyl which is attached via a ring nitrogen atom or is piperazinyl which is attached via a ring nitrogen atom and which may be substituted on the second ring nitrogen atom by methyl, ethyl, 2-hydroxyethyl, 2-methoxyethyl, acetyl, tert-butoxycarbonyl or methylsulfonyl,
  $R^2$ is phenyl which may be substituted by fluorine or hydroxy in position 4 relative to the linkage point on the phenyl ring, and
  $R^3$ is located in position 4 relative to the linkage point of the pyridazinone ring and is hydrogen, fluorine, chlorine, methyl or trifluoromethyl.

Especially preferred compounds of the formula (I) are selected from the group of the following compounds:

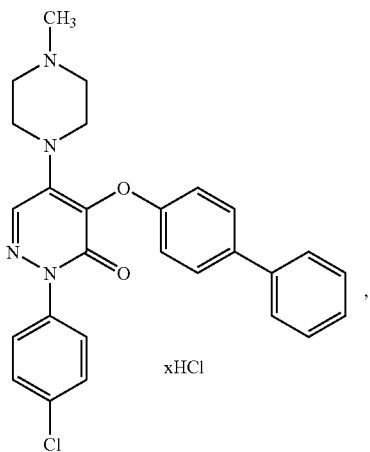

,

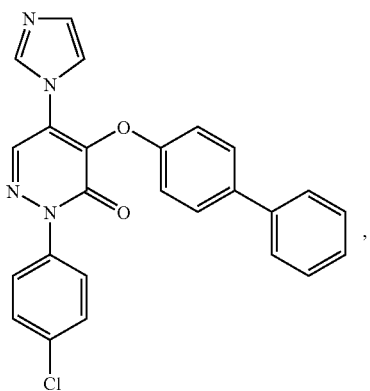

,

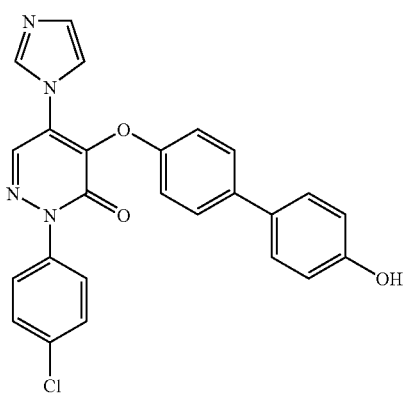

The invention further relates to a process for preparing the compounds of the formula (I), characterized in that compounds of the formula (II)

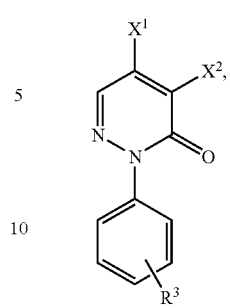

in which
R³ has the meaning indicated above, and
X¹ and X² are each halogen, preferably bromine or chlorine,
are first converted with a compound of the formula (III)

$$R^1\text{—}H \quad (III),$$

in which R¹ has the meaning indicated above in an inert solvent, where appropriate in the presence of an auxiliary base and/or of an alkali metal iodide, into compounds of the formula (IV)

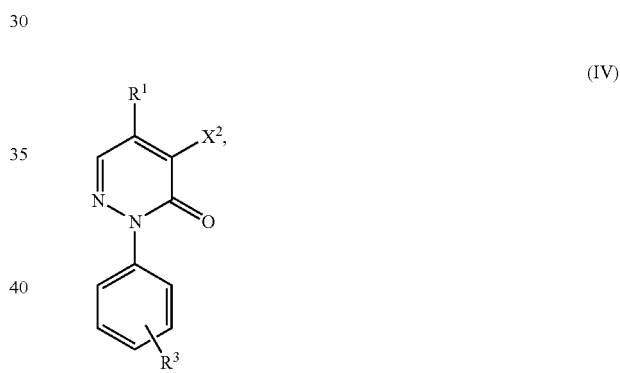

in which R¹, R³ and X² each have the abovementioned meaning, and the latter are then reacted with a compound of the formula (V)

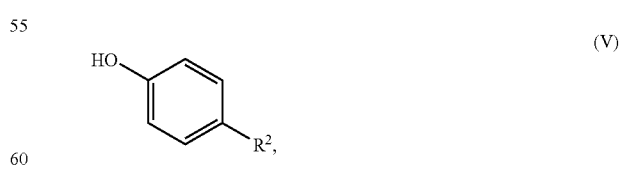

in which R² has the meaning indicated above, in an inert solvent in the presence of a base and, where appropriate, in the presence of an alkali metal iodide.

Inert solvents for both process steps are, for example, alcohols such as methanol, ethanol, n-propanol, isopropanol, n-butanol, tert-butanol or ethylene glycol mono-methyl ether, ethers such as diethyl ether, methyl tert-butyl ether, dioxane, tetrahydrofuran, ethylene glycol dimethyl ether or diethylene glycol dimethyl ether, or dipolar aprotic solvents such as dimethylformamide, dimethylacetamide, dimethyl sulfoxide, sulfolane or N-methylpyrrolidone. Dimethylformamide or n-methylpyrrolidone is preferred.

Both process steps can also where appropriate be carried out without solvent, i.e. undiluted or in the melt.

Examples of suitable auxiliary bases for process step (II)+(III)→(IV) are alkali metal or alkaline earth metal carbonates such as sodium, potassium, cesium or calcium carbonate, or tertiary organic amines such as triethylamine, diisopropylethylamine, N-methylmorpholine, N-methylpiperidine or 1,4-diazabicyclo-[2.2.2]octane. Tertiary amines are preferred. The auxiliary base is in this case employed in a molar ratio of from 0.75:1 to 2:1 based on the compound (II); a molar ratio of from 0.95:1 to 1.5:1 is preferred.

Bases suitable for process step (IV)+(V)→(I) are alkali metal or alkaline earth metal carbonates such as sodium, potassium or calcium carbonate, alkali metal alcoholates such as sodium or potassium methanolate, sodium or potassium ethanolate or potassium tert-butoxide, alkali metal hydrides such as sodium or potassium hydride, amides such as sodamide, lithium bis(trimethylsilyl)amide or lithium diisopropylamide, tertiary organic amines such as triethylamine, ethyldiisopropylamine, N-methylmorpholine, N-methylpiperidine or 1,4-diazabicyclo[2.2.2]octane, or organometallic compounds such as n-butyllithium. 1,4-Diazabicyclo[2.2.2]octane; sodium hydride, potassium hydride or potassium tert-butoxide is preferred. The base is in this case employed in a molar ratio of from 0.75:1 to 2:1 based on the compound (V); a molar ratio of from 0.95:1 to 1.5:1 is preferred.

Both process steps can be carried out in the presence of alkali metal iodides such as lithium, sodium, potassium or cesium iodide. The iodide in this case is employed in a molar ratio of from 0.001:1 to 2:1 based on the compound (II) or (IV); a molar ratio of from 0.01:1 to 1:1 is preferred.

The compounds (II) and (III) are employed in a molar ratio of from 1:1 to 1:10, preferably of from 1:1 to 1:5. The reaction is carried out in a temperature range from +20° C. to +200° C., preferably from +20° C. to +120° C. The reaction can be carried out under atmospheric pressure, under reduced or under elevated pressure; it is preferably carried out under atmospheric pressure.

The compounds (IV) and (V) are employed in a molar ratio of from 10:1 to 1:10, preferably from 1:1 to 1:3. The reaction is carried out in a temperature range from +20° C. to +200° C., preferably from +100° C. to +180° C. The reaction can be carried out under atmospheric pressure, under reduced or under elevated pressure; it is preferably carried out under atmospheric pressure.

The compounds of the formula (II) are known or can be prepared in analogy to processes known from the literature [see, for example, Drury, *Angew. Chemie* 77, 282 (1965)].

The compounds of the formulae (III) and (V) are commercially available, known from the literature or can be prepared in analogy to processes known from the literature.

In one variant of the process, the compounds of the formula (I) can also be obtained by either

[A] Reacting compounds of the formula (VI)

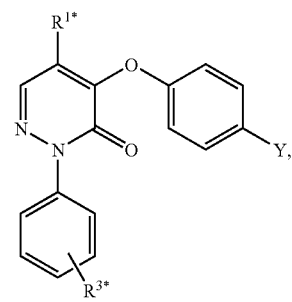

in which $R^{1*}$ has the meaning indicated above for $R^1$, but is not in turn substituted by bromine or iodine, $R^{3*}$ has the meaning indicated above for $R^3$, but is not bromine or iodine, and Y is bromine, iodine or trifluoromethylsulfonyloxy (triflate), in a coupling reaction with a compound of the formula (VII)

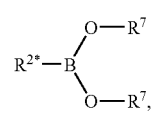

in which $R^{2*}$ has the meaning indicated above for $R^2$, but is not in turn substituted by bromine or iodine, and $R^7$ is hydrogen or methyl, or the two radicals together form a $CH_2CH_2$ or $C(CH_3)_2$—$C(CH_3)_2$ bridge, in an inert solvent in the presence of a suitable palladium catalyst and of a base, or

[B] Reacting compounds of the formula (VIII)

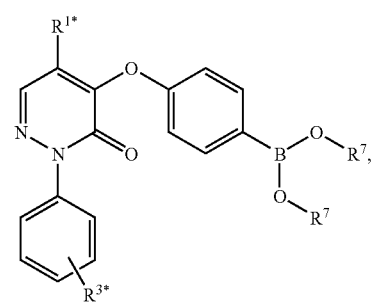

in which $R^{1*}$, $R^{3*}$ and $R^7$ each have the meaning indicated above, in a coupling reaction with a compound of the formula (IX)

$R^2$-Z (IX), in which

R² has the meaning indicated above, and

Z is bromine or iodine, in an inert solvent in the presence of a suitable palladium catalyst and of a base.

Examples of suitable inert solvents for variant [A] of the process are alcohols such as methanol, ethanol, n-propanol, isopropanol or n-butanol, aromatic hydrocarbons such as benzene, xylene or toluene, or dipolar aprotic solvents, such as dimethylformamide, dimethylacetamide, dimethyl sulfoxide, sulfolane or n-methylpyrrolidone. It is likewise possible to employ mixtures of said solvents. Dimethylformamide or a mixture of ethanol and toluene is preferred.

Examples of inert solvents suitable for variant [B] of the process are dipolar aprotic solvents such as dimethylformamide, dimethylacetamide, dimethyl sulfoxide, sulfolane or N-methylpyrrolidone. Dimethyl sulfoxide is preferred.

Palladium catalysts suitable for both variants of the process are the palladium(0) and palladium(II) complex compounds usual for Suzuki couplings; palladium tetrakis-triphenylphosphane, [1,1-bis(diphenylphosphino)-ferrocenyl] dichloropalladium(II) complex or bistriphenylphosphane dichloropalladium(II) complex is preferred. The palladium compound is in this case employed in a molar ratio of from 0.005:1 to 0.5:1, preferably in a molar ratio of from 0.02:1 to 0.15:1, based on the compound (VI) or (VIII).

Bases suitable for both variants of the process are aqueous solutions of alkali metal carbonates and bicarbonates and of alkali metal salts of acetic or propionic acid; sodium carbonate is preferred. Based on the compound (VI) or (VIII), a molar ratio of from 1:1 to 10:1, preferably of from 1.5:1 to 8:1, of the base is used.

The compounds (VI) and (VII) are employed in a molar ratio of from 3:1 to 1:3, preferably of from 1.2:1 to 1:1.2. The reaction is carried out in a temperature range from +20° C. to +150° C., preferably from +50° C. to +100° C. The reaction can be carried out under atmospheric pressure, under reduced or under elevated pressure; it is preferably carried out under atmospheric pressure.

The compounds (VIII) and (IX) are employed in a molar ratio of from 2:1 to 1:10, preferably from 1:1 to 1:3. The reaction is carried out in a temperature range from +20° C. to +150° C., preferably from +50° C. to +100° C. The reaction can be carried out under atmospheric pressure, under reduced or under elevated pressure; it is preferably carried out under atmospheric pressure.

The compounds of the formula (VI) and (VIII) can be prepared in accordance with the previously described process (IV)+(V)→(I).

The compounds of the formula (VIII) can also be obtained in analogy to variant [A] of the process by palladium-catalyzed reaction of compounds of the formula (VI) with appropriate boric acid derivatives such as, for example, 4,4,4',4',5,5,5',5'-octa-methyl-2,2'-bi-1,3,2-dioxaborolane [cf., for example, A. Suzuki, Acc. Chem. Res., 15, 178 (1982); Miyaura et al., J. Am. Chem. Soc., 111, 314 (1989)].

The compounds of the formula (VII) are commercially available, known from the literature or can be prepared in analogy to processes known from the literature [see, for example, A. Suzuki, in: Metal-catalyzed cross-coupling reactions, F. Driedrich and P. J. Stang, editors, Wiley, Weinheim 1998].

The compounds of the formula (IX) are commercially available, known from the literature or can be prepared in analogy to processes known from the literature.

In a further variant of the process, the compounds of the formula (I) can also be prepared by first converting compounds of the formula (II) with a compound of the formula (V) in an inert solvent in the presence of a base into compounds of the formula (X)

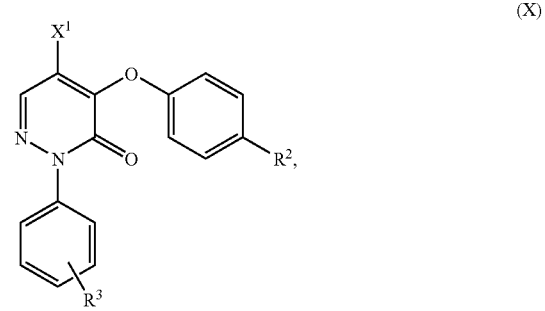

(X)

in which R², R³ and X¹ each have the meaning indicated above, and then reacting the latter with a compound of the formula (III) in an inert solvent, where appropriate in the presence of an auxiliary base and/or of an alkali metal iodide.

Inert solvents for process step (II)+(V)→(X) are advantageously ethers such as methyl tert-butyl ether, dioxane, tetrahydrofuran or ethylene glycol dimethyl ether. Dioxane is preferred.

Examples of inert solvents for process step (X)+(III)→(I) are ethers such as dioxane, tetrahydrofuran, ethylene glycol dimethyl ether or diethylene glycol dimethyl ether, or dipolar aprotic solvents such as dimethylformamide, dimethylacetamide, dimethylsulfoxide, sulfolane or N-methylpyrrolidone. Dimethylformamide is preferred. This process step can also where appropriate be carried out without solvent, i.e. undiluted or in the melt.

Examples of bases suitable for process step (II)+(V)→(X) are metal alcoholates such as sodium or potassium methanolate, sodium or potassium ethanolate, thallium methanolate or ethanolate or potassium tert-butoxide, metal hydrides such as sodium, potassium or lithium hydride, amides such as sodium or potassium amide, lithium or sodium bis(trimethylsilyl)amide or lithiumdiisopropylamide, or organometallic compounds such as methyl-, n-butyl- or phenyllithium. Sodium hydride is preferred. The base is in this case employed in a molar ratio of from 1.5:1 to 1:1.5, based on the compound (V); a molar ratio of from 1:1 to 1.1:1 is preferred. Reaction of the base with the compound (V) is carried out in a temperature range from −78° C. to +30° C.; on use of sodium hydride, this preferably takes place in a temperature range from 0° C. to +30° C.

Auxiliary bases suitable for process step (X)+(III)→(I) are alkali metal or alkaline earth metal carbonates such as sodium, potassium, cesium or calcium carbonate, or tertiary organic amines such as triethylamine, ethyldiisopropylamine, N-methylmorpholine or N-methylpiperidine; triethylamine or ethyldiisopropylamine is preferred. The base is employed in this case in a molar ratio of from 1:1 to 2:1 based on the compound (X), a molar ratio of from 1:1 to 1.5:1 is preferred.

Process step (X)+(III)→(I) can advantageously be carried out in the presence of alkali metal iodides such as lithium, sodium, potassium or cesium iodides; sodium or potassium iodide is preferred. The iodide is employed in this case in a molar ratio of from 0.1:1 to 2:1 based on the compound (X); a molar ratio of 1:1 is preferred.

The compounds (II) and (V) are employed in a molar ratio of from 0.5:1 to 2:1, preferably of 1:1. The reaction is carried out in a temperature range from 0° C. to +100° C., preferably from +10° C. to +30° C. The reaction can be carried out under atmospheric pressure, under reduced or under elevated pressure; it is preferably carried out under atmospheric pressure.

The compounds (III) and (X) are employed in a molar ratio of from 1:3 to 5:1, preferably from 1:1.5 to 2:1. The reaction is carried out in a temperature range from +50° C. to +200° C., preferably from +120° C. to +170° C. The reaction can be carried out under atmospheric pressure, under reduced or under elevated pressure; it is preferably carried out under atmospheric pressure.

In a further variant of the process, the compounds of the formula (I) can also be prepared by first converting compounds of the formula (II) with an excess of compound (V) in an inert solvent in the presence of a base and, where appropriate, in the presence of an alkali metal iodide into compounds of the formula (XI)

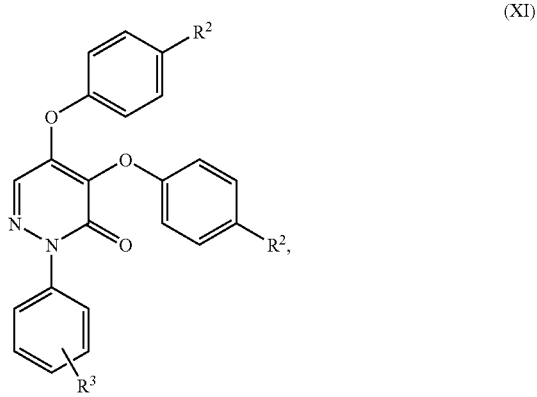

in which $R^2$ and $R^3$ each have the meaning indicated above, and then reacting the latter with a compound of the formula (III) in an inert solvent, where appropriate in the presence of an auxiliary base and/or of an alkali metal iodide.

Inert solvents for process step (II)+(V)→(XI) are advantageously aprotic solvents such as, for example, dimethylformamide, dimethylacetamide, dimethylsulfoxide or sulfolane or ethers such as methyl tert-butyl ether, dioxane, tetrahydrofuran or ethylene glycol dimethyl ether. Dimethylformamide is preferred.

Examples of inert solvents for process step (XI)+(III)→(I) are ethers such as dioxane, tetrahydrofuran, ethylene glycol dimethyl ether or diethylene glycol dimethyl ether, or dipolar aprotic solvents such as dimethylformamide, dimethylacetamide, dimethyl sulfoxide, sulfolane or N-methylpyrrolidone. Dimethylformamide is preferred. This process step can also where appropriate be carried out without solvent, i.e. undiluted or in the melt.

Examples of suitable bases for process step (II)+(V)→(XI) are metal alcoholates such as sodium or potassium methanolate, sodium or potassium ethanolate, thallium methanolate or ethanolate or potassium tert-butoxide, metal hydrides such as sodium, potassium or lithium hydride, amides such as sodium or potassium amide, lithium or sodium bis(trimethylsilyl)amide or lithium diisopropylamide, or organometallic compounds such as methyl-, n-butyl- or phenyllithium. Sodium hydride is preferred. The base is employed in this case in a molar ratio of from 1.5:1 to 1:1.5 based on the compound (V); a molar ratio of from 1:1 to 1.1:1 is preferred. Reaction of the base with the compound (V) is carried out in a temperature range from −78° C. to +30° C.; on use of sodium hydride, this preferably takes place in a temperature range from 0° C. to +30° C.

Auxiliary bases suitable for process step (XI)+(III)→(I) are alkali metal or alkaline earth metal carbonates such as sodium, potassium, cesium or calcium carbonate or tertiary organic amines such as triethylamine, ethyldiisopropylamine, N-methylmorpholine, N-methylpiperidine or 1,4-diazabicyclo[2.2.2]octane; 1,4-diazabicyclo[2.2.2]octane or ethyldiisopropylamine is preferred. The base is employed in this case in a molar ratio of from 0.75:1 to 2:1 based on the compound (III); a molar ratio of from 0.95:1 to 1.5:1 is preferred.

Process step (II)+(V)→(XI) can advantageously be carried out in the presence of alkali metal iodides such as lithium, sodium, potassium or cesium iodide; sodium or potassium iodide is preferred. The iodide is in this case employed in a molar ratio of from 0.05:1 to 2:1 based on the compound (V); a molar ratio of from 0.1:1 to 0.5:1 is preferred.

Process step (XI)+(III)→(I) can likewise advantageously be carried out in the presence of alkali metal iodides such as lithium, sodium, potassium or cesium iodide; sodium or potassium iodide is preferred. The iodide is in this case employed in a molar ratio of from 0.1:1 to 2:1 based on the compound (XI); a molar ratio of 1:1 is preferred.

The compounds (II) and (V) are employed in a molar ratio of from 0.05:1 to 0.5:1, preferably of from 0.1:1 to 0.5:1. The reaction is carried out in a temperature range from +50° C. to +200° C., preferably from +100° C. to +160° C. The reaction can be carried out under atmospheric pressure, under reduced or under elevated pressure; it is preferably carried out under atmospheric pressure.

The compounds (III) and (XI) are employed in a molar ratio of from 1:1 to 5:1, preferably of from 1:1 to 2:1. The reaction is carried out in a temperature range from +50° C. to +200° C., preferably from +100° C. to +170° C. The reaction can be carried out under atmospheric pressure, under reduced or under elevated pressure; it is preferably carried out under atmospheric pressure.

Compounds of the formula (I), in which $R^1$ is optionally substituted 1,2,3-triazol-1-yl can also be prepared by first converting compounds of the formula (X) with a metal azide in an inert solvent into compounds of the formula (XII)

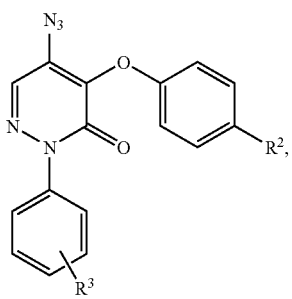

(XII)

in which $R^2$ and $R^3$ each have the meaning indicated above, and then reacting the latter with a compound of the formula (XIII)

(XIII), in which $R^8$ and $R^9$ are independently of one another hydrogen, $(C_1-C_6)$-alkoxycarbonyl or are $(C_1-C_6)$-alkyl which may in turn be substituted by hydroxy or halogen, in the presence or in the absence of an inert solvent to give compounds of the formula (XIVa) or (XIVb)

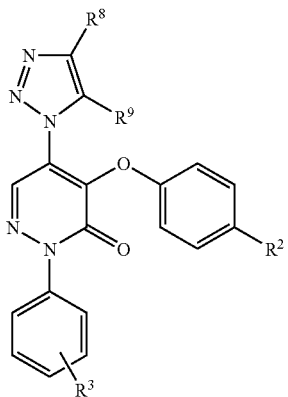

(XIVa)

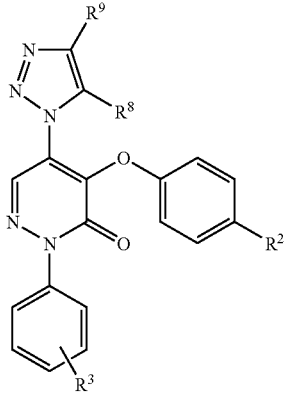

(XIVb)

in which $R^2$, $R^3$, $R^8$ and $R^9$ each have the meaning indicated above.

Examples of inert solvents for process step (X)→(XII) are advantageously aprotic solvents such as, for example, dimethylformamide, dimethylacetamide, dimethyl sulfoxide, sulfolane, acetone, acetonitrile or ethers such as dioxane, tetrahydrofuran or ethylene glycol dimethyl ether. Dimethylformamide is preferred.

Examples of inert solvents for process step (XII)+(XIII) →(XIVa) or (XIVb) are ethers such as dioxane, tetrahydrofuran, ethylene glycol dimethyl ether or diethylene glycol dimethyl ether, dipolar aprotic solvents such as dimethylformamide, dimethylacetamide, dimethyl sulfoxide, sulfolane or N-methylpyrrolidone, or aromatic hydrocarbons such as benzene, toluene or isomeric xylenes, or chlorobenzene or nitrobenzene. This process step can also where appropriate be carried out without solvent. The reaction is preferably carried out in toluene or without solvent.

The compounds (X) are reacted with the azide in a molar ratio of from 1:1 to 1:15, preferably of from 1:2 to 1:6. The azides used are alkali metal salts of hydrazoic acid; sodium azide is preferred. The reaction is carried out in a temperature range from +20° C. to +80° C., preferably from +40° C. to +60° C. The reaction can be carried out under atmospheric pressure, under reduced or under elevated pressure; it is preferably carried out under atmospheric pressure.

The compounds (XII) and (XIII) are employed in a molar ratio of from 1:1 to 1:15, preferably of from 1:2 to 1:8. The reaction is carried out in a temperature range from +20° C. to +130° C., preferably from +80° C. to +120° C. The reaction can be carried out under atmospheric pressure, under reduced or under elevated pressure; it is preferably carried out under atmospheric pressure.

The compounds of the formula (XIII) are commercially available, known from the literature or can be prepared in analogy to processes known from the literature.

The compounds of the formula (I) surprisingly showed a valuable range of pharmacological effects which could not have been predicted and are therefore suitable in particular for the prophylaxis and/or treatment of disorders in humans and animals.

The pharmaceutical activity of the compounds of the formula (I), in particular their antifibrotic effect, can be explained by their effect as lysyl oxidase inhibitors.

The compounds of the invention are, because of their pharmacological properties suitable alone or in combination with one or more other active ingredients for the prophylaxis and/or treatment of disorders in humans and warm-blooded species, in particular of disorders characterized by harmful buildup of collagen and/or by excessive lysyl oxidase enzymatic activity; irrespective of the disorder underlying this damage.

Detrimental basic disorders in this sense may be radiation damage, i.e. following radiotherapy, damage resulting from chemotherapy, e.g. with bleomycin or Adriamycin, viral disorders, e.g. hepatitis B infection, chronic intoxications such as, for example, alcohol abuse, parasitic disorders such as, for example, schistosomiasis, congenital disorders such as, for example, Wilson's syndrome, metabolic disorders such as, for example, diabetes, autoimmune diseases or else disorders of unknown origin. It is common to all of them that they induce fibrotic damage in one or more organs. Therapy with the compounds of the invention controls the fibrotic damage and the sequelae associated therewith, such as, for example, organ failure, varicosis, portal hypertension, formation of malignant tumors.

The therapeutic use of the compounds of the invention likewise includes the prophylaxis and/or treatment of fibrotic disorders of the internal organs. Examples which may be mentioned here are the lung, heart, kidney, bone marrow and, in literature or can be prepared in analogy to processes known from the literature.

The compounds of the formula (I) surprisingly showed a valuable range of pharmacological effects which could not have been predicted and are therefore suitable in particular for the prophylaxis and/or treatment of disorders in humans and animals.

The pharmaceutical activity of the compounds of the formula (I), in particular their antifibrotic effect, can be explained by their effect as lysyl oxidase inhibitors.

The compounds of the invention are, because of their pharmacological properties suitable alone or in combination with one or more other active ingredients for the prophylaxis and/or treatment of disorders in humans and warm-blooded species, in particular of disorders characterized by harmful buildup of collagen and/or by excessive lysyl oxidase enzymatic activity; irrespective of the disorder underlying this damage.

Detrimental basic disorders in this sense may be radiation damage, i.e. following radiotherapy, damage resulting from chemotherapy, e.g. with bleomycin or Adriamycin, viral disorders, e.g. hepatitis B infection, chronic intoxications such as, for example, alcohol abuse, parasitic disorders such as, for example, schistosomiasis, congenital disorders such as, for example, Wilson's syndrome, metabolic disorders such as, for example, diabetes, autoimmune diseases or else disorders of unknown origin. It is common to all of them that they induce fibrotic damage in one or more organs. Therapy with the compounds of the invention controls the fibrotic damage and the sequelae associated therewith, such as, for example, organ failure, varicosis, portal hypertension, formation of malignant tumors.

The therapeutic use of the compounds of the invention likewise includes the prophylaxis and/or treatment of fibrotic disorders of the internal organs. Examples which may be mentioned here are the lung, heart, kidney, bone marrow and, in particular, liver. The compounds of the invention can therefore be used to treat for example hepatic fibrosis, cirrhosis of the liver, pulmonary fibrosis, endomyocardial fibrosis, cardiomyopathy, nephropathy, glomerulonephritis, interstitial renal fibrosis, fibrotic damage resulting from diabetes, myelofibrosis and similar fibrotic disorders.

In a further aspect of the invention, dermatological fibroses are treated by compounds of the formula (I). Examples of such disorders which may be mentioned are scleroderma, morphea; keloids, hypertrophic scarring (also following surgical procedures) and naevi. The compounds of the invention an also be employed for aging and keratinizing skin.

It is also possible with the compounds of the invention to treat fibrotic disorders of the eye such as diabetic retinopathy and proliferative vitroretinopathy; they can also be employed advantageously for controlling postoperative scarring, e.g. following glaucoma operations.

The compounds of the invention can additionally be employed therapeutically in the control of neoplastic disorders, especially those disorders characterized by metastasis associated with neoangiogenesis.

The present invention also relates to the use of the compounds of the formula (I) for producing medicaments for the prophylaxis and/or treatment of the aforementioned pathological states.

The present invention further relates to a method for the prophylaxis and/or treatment of the aforementioned pathological states using the compounds of the formula (I).

The present invention further relates to medicaments which comprise at least one compound of the formula (I), preferably together with one or more pharmacologically acceptable excipients or carriers, and to the use thereof for the aforementioned purposes.

The active ingredients can be converted in a known manner into the usual formulations such as tablets, coated tablets, pills, granules, aerosols, syrups, creams, emulsions, suspension and solutions, using inert, nontoxic pharmaceutically suitable carriers and solvents. In each of these cases, the therapeutically active compound is to be present in a concentration of about 0.01 to 90% by weight of the complete mixture, i.e. in amounts sufficient to reach the indicated dosage range.

The formulations are produced for example by extending the active ingredients with solvents and/or carriers, where appropriate using emulsifiers and/or dispersants, it being possible where appropriate, for example when water is used as diluent, to use organic solvents as auxiliary solvents.

Administration takes place in a conventional way, preferably orally, parenterally or topically.

In the case of parenteral administration, solutions of the active ingredients can be employed using suitable liquid carrier materials.

It has generally proved advantageous on intravenous administration to administer amounts of about 0.001 to 20 mg/kg, preferably about 0.01 to 10 mg/kg, of bodyweight to achieve effective results, and on oral administration the dosage is about 0.01 to 60 mg/kg, preferably 0.1 to 30 mg/kg, of bodyweight.

In may nevertheless be necessary to deviate from the stated amounts, in particular as a function of bodyweight and the nature of the administration route, on the individual response towards the medicament, the nature of its formulation and the time or interval over which administration takes place. Thus, it may in some cases be sufficient to make do with less than the aforementioned minimum amount, whereas in other cases the stated upper limit must be exceeded. Where larger amounts are administered, it may be advisable to divide them into a plurality of single doses over the day.

The present invention is illustrated by the following, non-restrictive, preferred examples which, however, by no means limit the invention.

The percentage data in the following tests and examples are, unless indicated otherwise, percentages by weight; parts are parts by weight. Solvent ratios, dilution ratios and concentration data for liquid/liquid mixtures are in each case based on volume.

A. Assessment of the Physiological Activity

The following biological assays can be used to investigate the in vitro and in vivo effects of the compounds of the invention:

1. Test for Lysyl Oxidase-inhibitory Effect:

The enzyme was isolated from bovine aortas in a modification of a method of Kagan et al. [*Biochem. J.* 177, 203-214 (1979)] by extraction with phosphate buffer containing urea, followed by precipitation and chromatography on DEAE-Sephadex.

The test solution (total volume 200 µl) is composed of 1.5 mM homovanillinic acid, 5 mM 1,5-diaminopentane, 1 unit of horseradish peroxidase and 1.5 M urea in 50 mM sodium borate buffer of pH 8.2. The enzyme was preincubated with the compound to be tested for 15 minutes; the reaction was started by adding diaminopentane and homovanillin/horseradish peroxidase. The fluorescence of the homovanillin dimer which formed was measured with excitation at 315 nm and emission at 425 nm. This test arrangement is a modification of the method of Trackman et al. [*Anal. Biochem.* 113, 336-341 (1981)].

The $IC_{50}$ as a measure of the inhibition of lysyl oxidase is found by testing various concentrations of substance and using the concentration-effect plots. Examples of $IC_{50}$ values for the compounds of the invention are listed in Table 1 below:

TABLE 1

|  | $IC_{50}$ (µM) |
| --- | --- |
| Comparative compounds: | |
| β-Aminopropionitrile (BAPN) | 10 |
| 4-Ethoxy-2-methyl-5-morpholino-3(2H)-pyridazinone (emorfazone) | >4 |
| Exemplary embodiments: | |
| Ex. 5 | 0.017 |
| Ex. 8 | 0.007 |
| Ex. 82 | 0.011 |
| Ex. 12 | 0.003 |
| Ex. 25 | 0.005 |
| Ex. 34 | 0.009 |
| Ex. 81 | 0.007 |
| Ex. 176 | 0.010 |

The compounds of the invention show a distinctly stronger enzyme inhibitory effect on lysyl oxidase than does the reference compound BAPN or 4-ethoxy-2-methyl-5-morpholino-3(2H)-pyridazinone (emorfazone) which corresponds to the structurally closest prior art.

2. Test of Antifibrotic Effect in the Liver:

2.1 Animal Models:

a) Model of Chronic Carbon Tetrachloride Intoxication:

Chronic carbon tetrachloride ($CCl_4$) treatment is a standard method for generating hepatic fibrosis of nonviral origin and subsequent cirrhosis. It is generally accepted as a model of hepatic fibrosis and cirrhosis in humans [E. McLean, A. McLean, P. Sutton, Instant Fibrosis: An improved method for producing cirrhosis of the liver in rats by simultaneous administration of carbon tetrachloride and phenobarbitone, *Br. J. Exp. Pathol.* 50, 502-506 (1969)].

Female Sprague-Dawley rats (200-220 g) were employed. In order to achieve maximum microsomal metabolization of the $CCl_4$, the animals received isoniazid in the drinking water (1 g/l) for one week before starting the administration of carbon tetrachloride. $CCl_4$ was administered orally each fifth day in a dose of 0.2 ml/100 g of bodyweight in a 1:1 mixture with mineral oil. The compounds of the invention were given orally in the same period, as indicated in Table 3, preferably in Solutol®/ethanol/PBS mixtures. Necropsy was performed 6 weeks after starting the treatment.

b) Model of Bile Duct Ligature:

The experiments were carried out with female Sprague-Dawley rats (200-220 g). In order to generate chronic fibrosis, the bile duct (common hepatic duct) was doubly ligated in a surgical procedure. Ethibloc® occlusion emulsion (Ethicon, Norderstedt, Germany), a mixture of prolamine and ethanol, was instilled retrogradely into the biliary system [J. Kountouras, B. Billing, P. Scheuer, Prolonged bile obstruction: A new experimental model for cirrhosis in the rat, *Br. J. Exp. Pathol.* 65, 305-311 (1984); G. Boigk, L. Stroedter, H. Herbst, J. Waldschmidt, E. O. Riecken, D. Schuppan, Silymarin retards collagen accumulation in early and advanced biliary fibrosis secondary to complete bile duct obliteration in rats, *Hepatology* 26, 643-649 (1997)]. The compounds of the invention were given orally in the same period, as indicated in Table 2, preferably in Solutol®/ethanol/PBS mixtures. The animals were sacrificed and investigated three weeks after the surgical procedure.

c) Model of Serum-induced Hepatic Fibrosis:

A septal fibrosis can be induced in rats also by repeated injection of heterologous serum. For this purpose, 0.5 ml of sterile-filtered porcine serum is administered i.p. to each animal twice a week [Bhunchet and Wake, *Hepatology* 16, 1452-73 (1992)].

The experiments were carried out with female Sprague-Dawley rats (200-220 g). After 6-8 weeks, the septal fibrosis is histologically manifest and can also be detected through an increase in the liver hydroxyproline content.

2.2 Evaluation of the Animal Models:

a) Histological Assessments/Morphometry:

Standardized transverse cylinders of liver tissue (approx. 10×2 mm) were cut out of the right anterior lobe of each rat liver. Frozen sections were stained with 0.1% picrosirius red solution to detect scar collagen associated with hepatic fibrosis. The contrast was increased by counterstaining with fast green. The extent of hepatic fibrosis was found as a percentage of the part stainable with picrosirius red in each section. A Leica Quantimed 500 MC system (Leica, Germany) was used for automatic morphometry. In this case, the color detection parameters were standardized and left constant during an experiment. 64 viewing fields which by means of a standard reticle which covers 31 $mm^2$ were employed with 100× magnification for the evaluation.

b) Collagen Content:

The total collagen content was estimated by means of the tissue 4-hydroxyproline concentration. The method of Prockop and Udenfried [D. J. Prockop and S. Udenfried, A specific method for the analysis of hydroxyproline in tissues and urine, *Anal. Biochem.* 1, 228-239 (1960)] in modified form was used: liver samples with a wet weight of 60-90 mg were dried and then hydrolyzed in 6 N hydrochloric acid at 100° C. for 17 hours. The hydrolyzate was dried by evaporation and reconstituted in 5 ml of deionized water. 200 µl of this hydrolyzate were mixed with 200 µl of ethanol and oxidized with 200 µl of a 0.7% strength solution of chloramine T in citrate buffer (5.7 g of sodium acetate, 3.75 g of trisodium citrate, 0.55 g of citric acid, 38.5 ml of ethanol, made up to 100 ml with water) at room temperature for 20 minutes. Then, 400 µl of Ehrlich's reagent (12 g of p-dimethylaminobenzaldehyde and 2.7 g of sulfuric acid in 40 ml of ethanol) were added thereto. After incubation at 35° C. for 3 hours, the absorption was measured at 573 nm. The hydroxyproline content, based on the dry weight of the liver samples employed, was found from these absorption values by means of a calibration plot.

2.3 Results:

As shown in Table 2, the compounds of the invention reduce the content of scar collagen in rats with hepatic fibrosis generated by bile duct ligature. It is evident from Table 3 that fibrosis generated by carbon tetrachloride in the animal model is also inhibited by compounds of the invention, because the total liver collagen content is reduced on administration of the substance. Table 4 demonstrates the effect on total collagen in serum-induced hepatic fibrosis.

TABLE 2

Effect on the content of fibrotic tissue in hepatic fibrosis following bile duct ligature in rats

| | Animals | | |
|---|---|---|---|
| | Intact (Sham-operated) | Bile duct ligated | Bile duct ligated |
| Administration of substance | Solutol/ethanol/ PBS | Solutol/ethanol/ PBS | 15 mg/kg Ex. 82 p.o. b.i.d. in Tolutol/ethanol/PBS |
| Proportionate area stainable with picrosirius red: average in % | 0.21 | 7.4 | 4.98 |
| S.E.M. | 0.03 | 0.72 | 0.58 |
| N (number of animals) | 5 | 11 | 11 |
| P | | | <0.05 vs. vehicle |

This effect corresponds to an inhibition of approx. 34% in fibrosis.

TABLE 3

Effect on total collagen in hepatic fibrosis resulting from chronic administration of carbon tetrachloride in rats

| | Animals | | |
|---|---|---|---|
| | Intact | $CCl_4$ | $CCl_4$ |
| Administration of substance | Solutol/ethanol/ PBS | Solutol/ethanol/ PBS | 30 mg/kg Ex. 82 p.o. o.d. in Solutol/ethanol/ PBS |
| 4-Hydroxyproline content: average in mg/g dry weight | 0.504 | 1.921 | 1.260 |
| S.E.M. | 0.019 | 0.308 | 0.121 |
| N (number of animals) | 5 | 11 | 11 |
| P | | | =0.059 vs. vehicle |

TABLE 4

Effect on total collagen in serum-induced hepatic fibrosis in rats

| | Animals | | |
|---|---|---|---|
| | Intact | Serum-treated | Serum-treated |
| Administration of substance | Solutol/ethanol/ PBS | Solutol/ethanol/ PBS | 3 mg/kg Ex. 34 p.o. o.d. in Solutol/ ethanol/PBS |
| 4-Hydroxyproline content: average in mg/g dry weight | 0.577 | 2.070 | 1.293 |
| S.E.M. | 0.038 | 0.188 | 0.180 |
| N (number of animals) | 5 | 15 | 15 |
| P | | <0.001 | <0.01 |

B. Examples

| Abbreviations: | |
|---|---|
| APCI | Atmospheric pressure - chemical ionization (in MS) |
| Boc | tert-Butoxycarbonyl |
| DCI | Direct chemical ionization (in MS) |
| Decomp. | Decomposition |
| DMAP | 4-N,N-Dimethylaminopyridine |
| DMF | N,N-Dimethylformamide |
| DMSO | Dimethyl sulfoxide |
| EDC | N'-(3-Dimethylaminopropyl)-N-ethylcarbodiimide × HCl |
| EI | Electron impact ionization (in MS) |
| eq | Equivalent(s) |
| ESI | Elektrospray ionization (in MS) |
| HOBt | 1-Hydroxy-1H-benzotriazole × $H_2O$ |
| HPLC | High pressure, high performance liquid chromatography |
| LC-MS | Coupled liquid chromatography-mass spectroscopy |
| MOM | Methoxymethyl |
| m.p. | Melting point |
| NMR | Nuclear magnetic resonance spectroscopy |
| $R_f$ | Retention index (in TLC) |
| $R_t$ | Retention time (in HPLC) |
| TLC | Thin-layer chromatography |

Analytical Methods:

Mass Spectroscopic Methods:
A: DCI, $NH_3$;
B: ESI;
C: ESIpos;
D: LC-MS/ESIpos;
E: APCI;
F: LC-MS Standard HPLC Method:
Column: Kromasil C-18 125×2 mm; flow rate: 0.5 ml/min; wavelength: 210 nm; temp.: 30° C.; eluent: gradient of $CH_3CN/0.01$ M $H_3PO_4$ General Preparation Processes:

General Method (1)

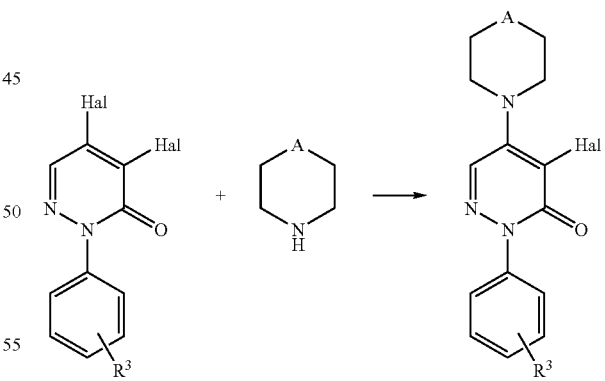

Variant (1a):

Amine (1.8-2.0 eq.) and triethylamine (1.5 eq) as auxiliary base are added to a suspension of 4,5-dihalopyridazin-3-one derivative (1 eq.) in 1,2-dichloroethane (0.4-0.5 mol/l). The mixture is heated to reflux for 15-20 h and, after cooling, diluted with dichloromethane. It is washed with 0.5 N hydrochloric acid solution and saturated sodium chloride solution, dried over magnesium sulfate and concentrated. The crude product is purified by crystallization from dichloromethane/diethyl ether mixtures or by chromatography on silica gel (dichloromethane/methanol mixtures).

Variant (1b):

Amine (1-3 eq.) and sodium iodide (8-10 mol %; catalytic amount) are added to a solution of 4,5-dihalopyrazin-3-one derivative (1 eq.) in N-methyl-2-pyrrolidine (NMP) and stirred at 65° C. for 4-8 h. After cooling, water is added, and the precipitate product is filtered off with suction. The residue on the filter is stirred in diethyl ether, filtered off with suction and dried under high vacuum.

Variant (1c): Dichloromethane or Dioxane Process

The amine (1-7 eq.) is slowly added to a suspension of 4,5-dichloropyrazin-3-one derivative (1 eq.) in dichloromethane or dioxane (in the case of dioxane, catalytic amounts of sodium iodide are added) and heated to reflux for 20 h. Cooling is followed by washing with 1 molar sodium hydroxide solution, and the dichloromethane phase is dried with sodium sulfate and concentrated. In the case of dioxane, the solvent is distilled off and the residue is partitioned in dichloromethane/water, and the organic phase is separated off and concentrated. Crystallization is effected by stirring the residue with ether.

General Method (2)

(Method for Acylation of Amine/Aniline Fragments in $R^1$, $R^2$ and $R^3$)

Example:

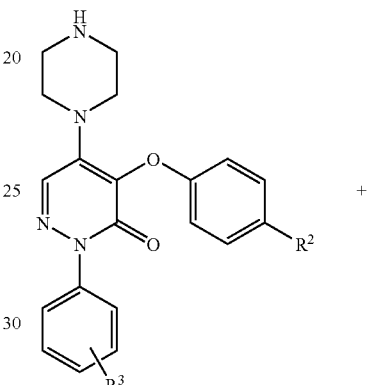

in ice. After conversion is complete (a catalytic amount of 4-DMAP is added where appropriate), the reaction mixture is warmed to room temperature and diluted with dichloromethane. It is washed with 1 N hydrochloric acid solution, saturated sodium bicarbonate solution and saturated sodium chloride solution, dried over magnesium sulfate and concentrated. The crude product is purified by crystallization from dichloromethane/diethyl ether mixture or by chromatography on silica gel (dichloromethane/methanol mixtures).

General Method (3)

(Method for Formylation of Amine/Aniline Fragments in $R^1$, $R^2$ and $R^3$)

Example:

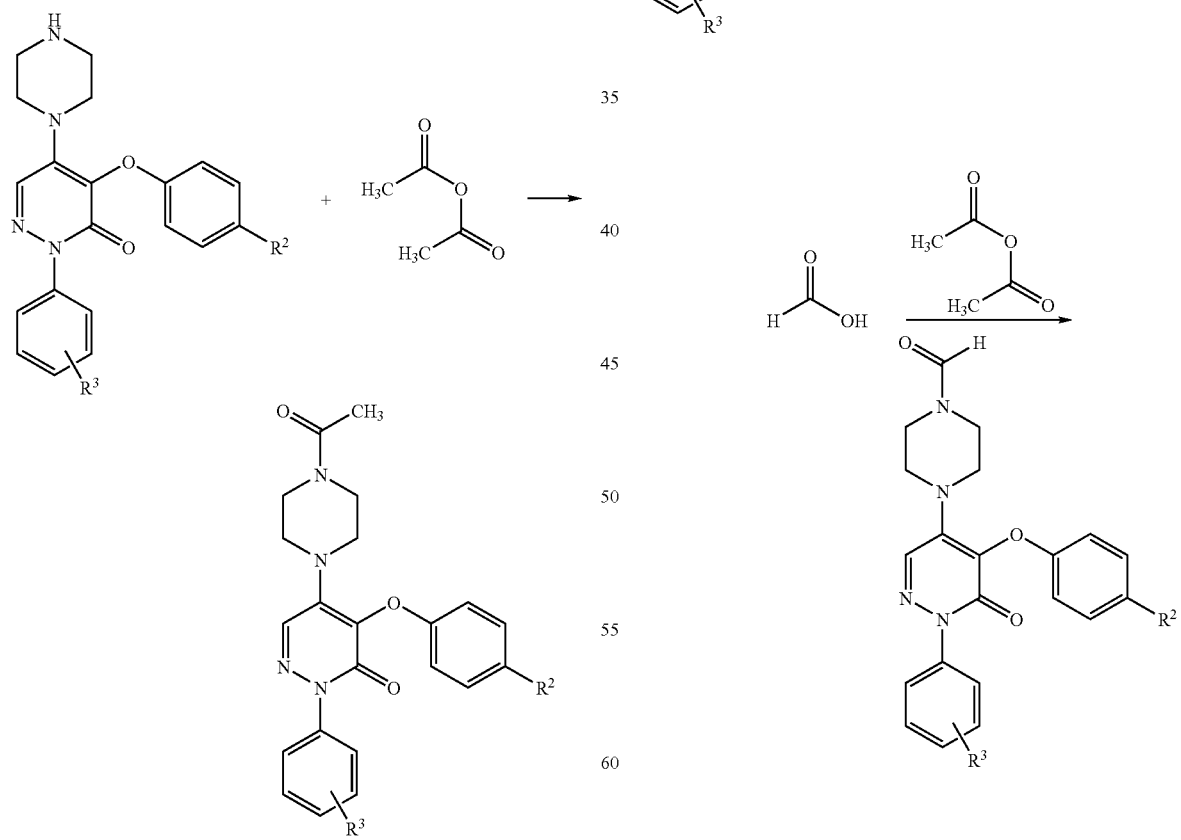

Acylating reagent (anhydride or acid chloride, 1.2-2.0 eq.) is added to a solution of an amine or aniline derivative (1 eq.) in absolute 1,2-dichloroethane (0.25-0.5 mol/l) cooled A mixture of formic acid (2.5 eq.) and acetic anhydride (2.0 eq.) is heated at 50° C. for 1 h and, after cooling, diluted with absolute dichloromethane (0.5 mol/l) and added to a mixture of amine or aniline derivative (1.0 eq.) and pyridine (3.0 eq.) in dichloromethane (0.5 mol/l). The reaction mixture is stirred at room temperature for several hours before being diluted with dichloromethane, washed with water and saturated sodium bicarbonate solution, dried over magnesium sulfate and concentrated. The crude product is purified where appropriate by crystallization from dichloromethane/diethyl ether mixtures.

General Method (4)

(Method for Mesylation of Amine/Aniline Fragments in $R^1$, $R^2$ and $R^3$)

Example:

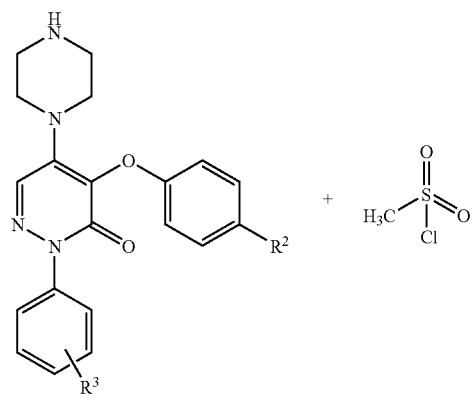

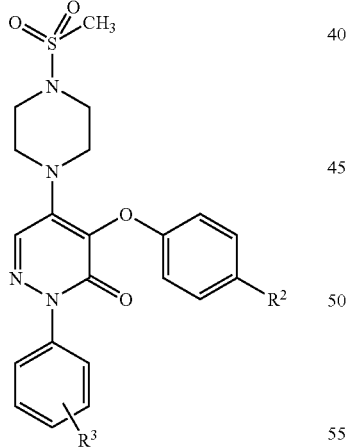

Methanesulfonyl chloride (1.2-2.0 eq.) is added dropwise to a solution of an amine or aniline derivative (1 eq.) and an auxiliary base (pyridine or triethylamine, 2.0-3.0 eq.) in absolute dichloromethane (0.25-0.5 mol/l) cooled in ice. After conversion is complete, the reaction solution is warmed to room temperature and diluted with dichloromethane. It is washed with 1 N hydrochloric acid solution, saturated sodium bicarbonate solution and saturated sodium chloride solution, dried over magnesium sulfate and concentrated. The crude product is purified by crystallization from dichloromethane/diethyl ether mixtures or by chromatography on silica gel (dichloromethane/methanol mixtures).

General Method (5)

(Method for Carbamoylation of Amine/Aniline Fragments in $R^1$, $R^2$ and $R^3$)

Example:

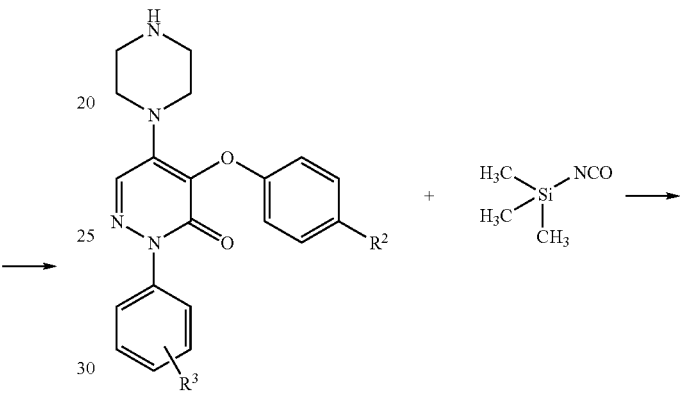

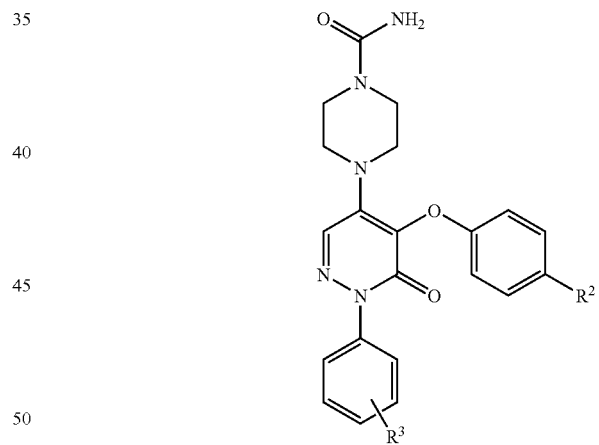

Trimethylsilyl isocyanate (8.0 eq.) is added dropwise to a mixture of an amine or aniline derivative (1 eq.) in absolute dichloromethane. The reaction mixture is stirred at room temperature over night and then concentrated and dried under high vacuum, and the residue is taken up in dichloromethane. The solution is washed with water, 2 N potassium carbonate solution and saturated sodium chloride solution, dried over magnesium sulfate and concentrated. The residue is purified by chromatography on silica gel or preparative thin-layer chromatography (dichloromethane/methanol mixtures).

General Method (6)

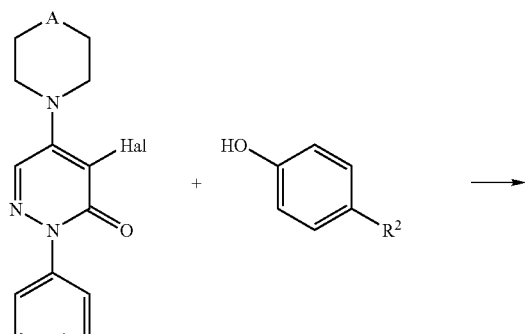

Hal = Br, Cl

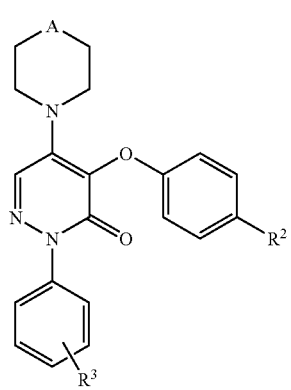

Variant (6-a), Potassium Salt Method:

A phenol derivative (3.0 eq.) is introduced in portions into a solution of potassium tert-butoxide (3.0 eq.) in absolute tetrahydrofuran (0.5 mol/l). After 30 min at room temperature, the solution is concentrated and the residue is dried under high vacuum. 4-Halopyridazin-3-one derivative (1.0 eq.), potassium iodide (0.1 eq.) and absolute dimethylformamide (0.5 ml/l) are added to the dried potassium phenolate. The mixture is stirred vigorously in an oil bath at 170° C. for 20-30 min before being cooled and the solvent being removed under high vacuum. The residue is taken up in dichloromethane and washed with 1 N sodium hydroxide solution (twice) and saturated sodium chloride solution, dried over magnesium sulfate and concentrated. The crude product is purified by crystallization from dichloromethane/diethyl ether mixtures or by chromatography on silica gel (dichloromethane/methanol mixtures).

Variant (6-b), Cesium Salt Method:

A phenol derivative (3.0 eq.), is introduced in portions into a suspension of cesium carbonate (1.5 eq.) in absolute methanol (0.5 mol/l). After 1 h at room temperature, the clear solution is concentrated and the residue is dried under high vacuum. 4-Halopyridazin-3-one derivative (1.0 eq) and absolute dimethylformamide (approx. 0.3 mol/l) are added to the dried cesium phenolate. The mixture is stirred vigorously at 120° C. overnight before being cooled and the solvent being removed under high vacuum. The residue is taken up in dichloromethane and washed with water, 1 N sodium hydroxide solution and saturated sodium chloride solution, dried over magnesium sulfate and concentrated. The crude product is purified by crystallization from dichloromethane/diethyl ether mixtures or by chromatography on silica gel (dichloromethane/methanol mixtures).

Variant (6-c), via 4-aryloxy-5-halopyridazin-3-one derivatives:

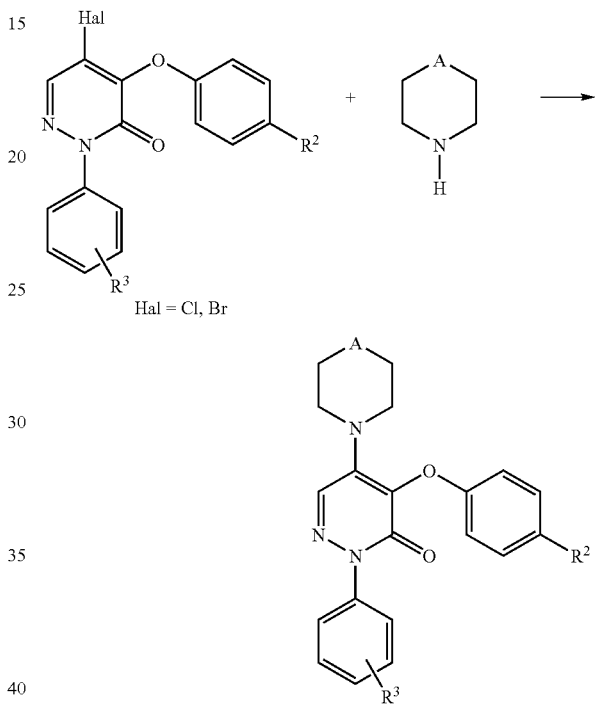

A mixture of a 4-aryloxy-5-halopyridazin-3-one derivative (1.0 eq., see method 12 for preparation) and a cyclic amine derivative (1.2 to 1.5 eq.), potassium iodide (1.0 eq.) and ethyldiisopropylamine (2.0 eq.) in absolute dimethylformamide is heated at 120° C. to 140° C. for 8 to 18 h. Cooling is followed by concentration under high vacuum, and the residue is taken up in dichloromethane. The solution is washed with dilute hydrochloric acid solution and saturated sodium chloride solution, dried over magnesium sulfate and concentrated in vacuo. The product is obtained from the crude mixture by chromatography on silica gel (dichloromethane/methanol mixtures) or by crystallization from diethyl ether or diethyl ether/dichloromethane mixtures.

Variant (6-d), Reaction in the Melt [Variant of Method (6a)]:

The potassium salt of a phenol is stirred with 4-halopyrazin-3-one derivatives (1 eq.) in DMF in an oil bath preheated to 175° C. for 30 min. Cooling to room temperature is followed by dilution with dichloromethane and washing with 1 molar sodium hydroxide solution. The organic phase is dried with sodium sulfate and concentrated. The crude product is purified by crystallization or by chromatography on silica gel (toluene/acetonitrile mixtures).

General Method (7)

(Method for Liberating Amine/Aniline Fragments in $R^1$, $R^2$ and $R^3$ from Boc-protected Precursors)

Example:

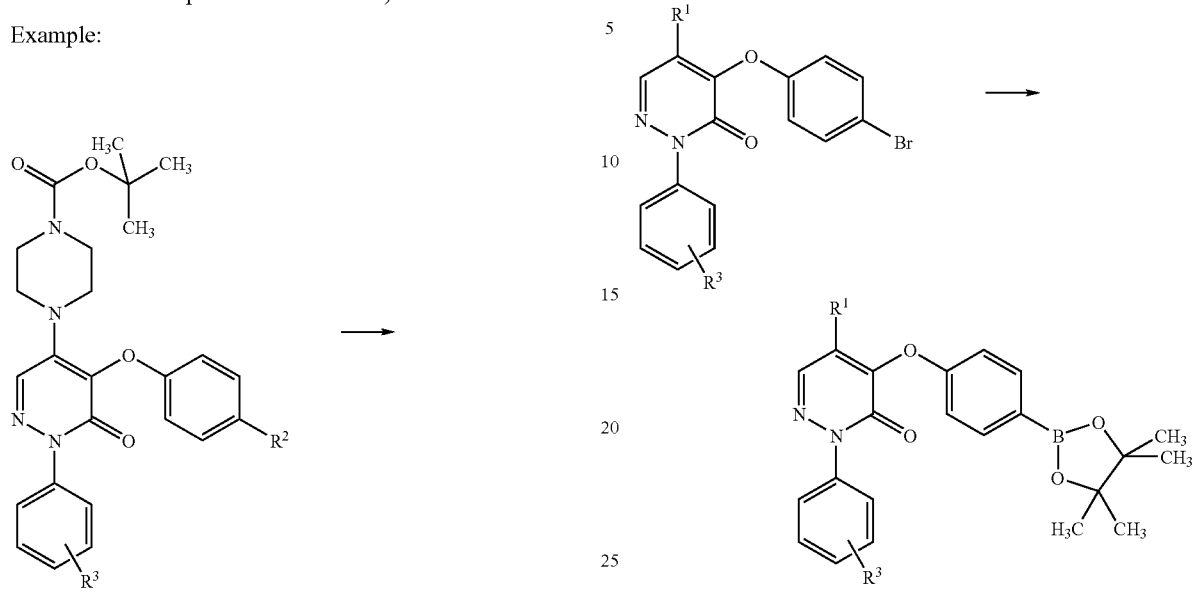

An ice-cooled mixture of tert-butyloxycarbonate (Boc)-protected amine (1.0 eq.) in dichloromethane (approx. 0.15 mol/l, addition of 2% water) is mixed with trifluoroacetic acid (60% of the amount of dichloromethane). The mixture is stirred vigorously at room temperature for about 3 h before being concentrated and dried under high vacuum. The residue is taken up in dichloromethane, washed with saturated sodium bicarbonate solution and saturated sodium chloride solution, dried over magnesium sulfate and concentrated. The crude product is purified by crystallization from dichloromethane/diethyl ether mixtures or by chromatography on silica gel (dichloromethane/methanol mixtures).

General method (8)

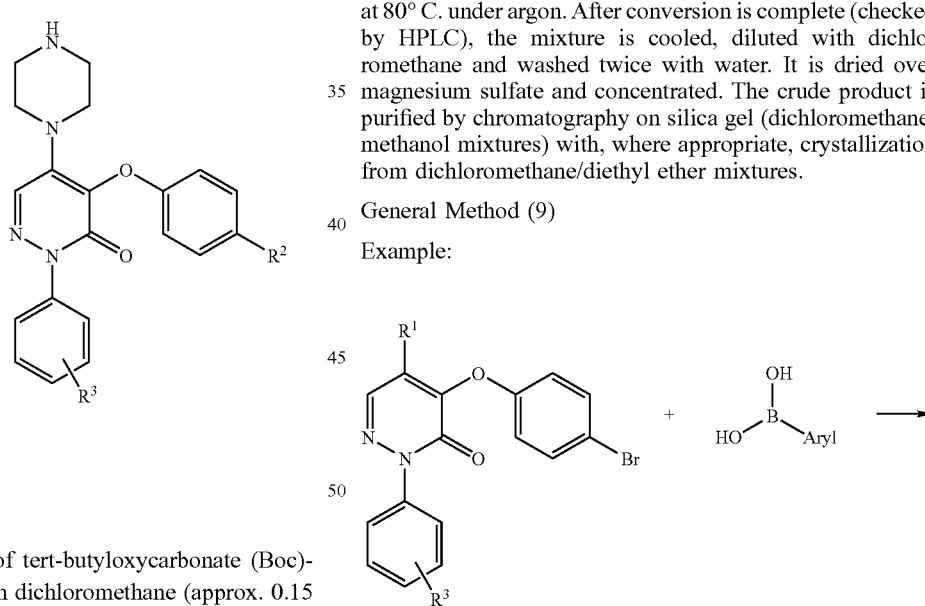

Aryl bromide (1.0 eq., see method 6 for preparation), bis(pinacolato)diboron (1.1 eq.), potassium acetate (3.0 eq.), DMSO and $PdCl_2(dppf)$ (0.04 eq.) are successively put into a flask flushed with argon. The mixture is stirred vigorously at 80° C. under argon. After conversion is complete (checked by HPLC), the mixture is cooled, diluted with dichloromethane and washed twice with water. It is dried over magnesium sulfate and concentrated. The crude product is purified by chromatography on silica gel (dichloromethane/methanol mixtures) with, where appropriate, crystallization from dichloromethane/diethyl ether mixtures.

General Method (9)

Example:

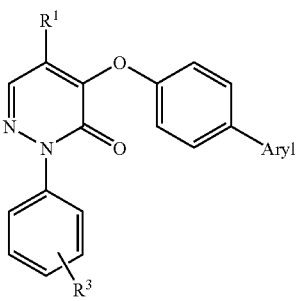

Variant (9-a), Via Boronic Acid Derivatives:

Aryl bromide (1.0 eq., see method 6 for preparation), arylboronic acid derivative (1.2-2.0 eq.), PdCl$_2$(dppf) (0.05 eq.), dimethylformamide (approx. 0.15 mol/l) and sodium carbonate (2.5 to 5.0 eq., as 2 N aqueous solution) are successively put into a flask flushed with argon. The mixture is vigorously stirred at 80° C. under argon (usually overnight) before being cooled and then concentrated under high vacuum. The residue either undergoes aqueous workup or is filtered through a silica gel column (dichloromethane/methanol mixtures). The crude product is purified by crystallization from dichloromethane/diethyl ether mixtures, by chromatography on silica gel (dichloromethane/methanol mixtures) or by preparative thin-layer chromatography (dichloromethane/methanol mixtures).

Variant (9-b), Via Borinate Ester Derivatives:

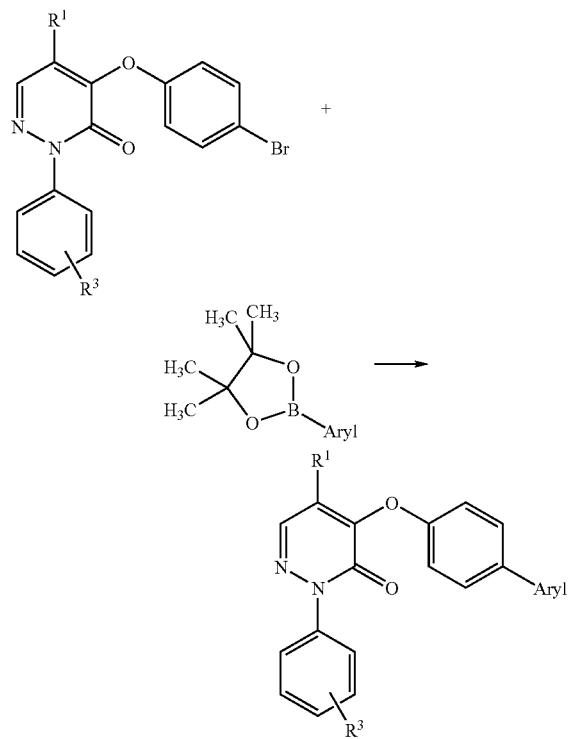

Aryl bromide or iodide (2.0 eq.), arylborinate ester derivative (1.0 eq., see method 8 for preparation), PdCl$_2$(dppf) (0.05 eq.), dimethylformamide (approx. 0.15 mol/l) and sodium carbonate (5.0 eq., as 2 N aqueous solution) are successively put into a flask flushed with argon. The mixture is stirred vigorously at 80° C. under argon (usually overnight) before being cooled and then concentrated under high vacuum. The residue either undergoes aqueous workup or is filtered through a silica gel column (dichloromethane/methanol mixtures). The crude product is purified by crystallization from dichloromethane/diethyl ether mixtures, by chromatography on silica gel (dichloromethane/methanol mixtures) or by preparative thin-layer chromatography (dichloromethane/methanol mixtures).

Variant (9-c), Via Borinate Ester Derivatives Generated In Situ:

Aryl bromide (1.0 eq., see method 6 for preparation), bis(pinacolato)diboron (1.1 eq.), potassium acetate (3.0 eq.), DMSO and PdCl$_2$(dppf) (0.04 eq.) are put successively into a flask flushed with argon. The mixture is stirred vigorously at 80° C. under argon. After conversion is complete (checked by HPLC), the mixture is cooled and filtered (aliquots can be taken at this point from parallel synthetic batches). Aryl bromide or iodide (2.0 eq.), PdCl$_2$(dppf) (0.05 eq.) and sodium carbonate (5.0 eq., as 2 N aqueous solution) are added successively to the resulting solution under argon. The reaction mixture is stirred vigorously at 80° C. under argon (usually overnight) before being cooled and then the crude products being obtained either by aqueous workup (addition of water and dichloromethane with subsequent phase separation through Chromaphil filter) or by precipitation after addition of water. Further purification takes place by chromatography on silica gel (dichloromethane/methanol mixtures), preparative thin-layer chromatography (dichloromethane/methanol mixtures) or preparative RP-HPLC; crystallization from dichloromethane/diethyl ether mixtures takes place where appropriate.

General Method (10)

(Method for Liberation of Phenol Fragments in R$^2$ and R$^3$ from MOM-protected Precursors)

Example:

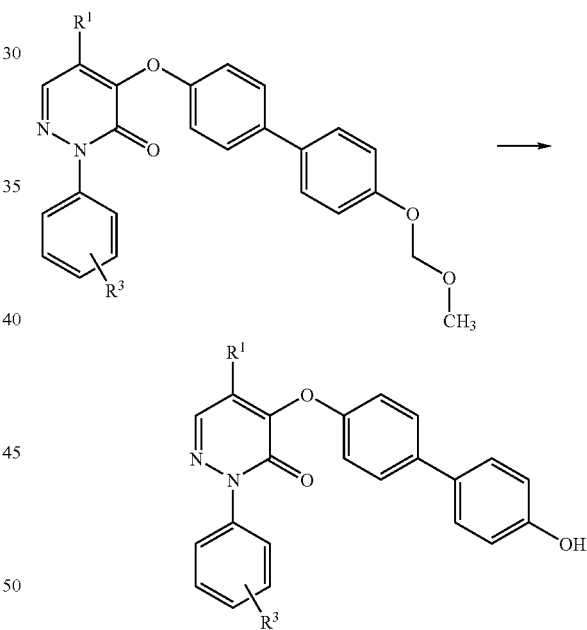

A mixture of a methoxymethyl (MOM)-protected phenol derivative in a mixture of acetic acid, water and trifluoroacetic acid (3:1:1, approx. 0.1 to 0.2 mol/l) is stirred vigorously at room temperature until conversion is complete. The reaction mixture is concentrated and dried under high vacuum. The residue is washed with saturated sodium bicarbonate solution and sodium chloride solution, dried over magnesium sulfate and concentrated. The product is purified if necessary by crystallization from dichloromethane/diethyl ether mixtures, by chromatography on silica gel (dichloromethane/methanol mixtures) or by preparative thin-layer chromatography (dichloromethane/methanol mixtures).

General Method (11)

(Method for Etherification of Phenol Fragments in R² and R³)

Example:

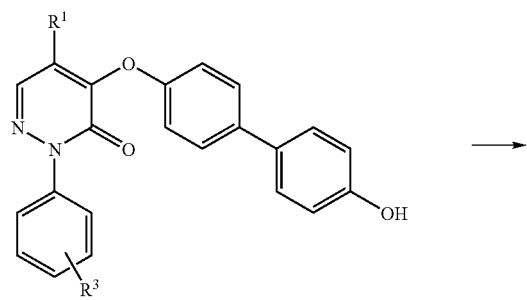

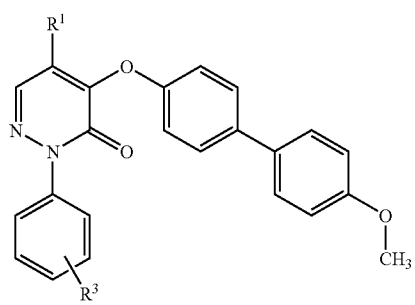

An excess of methyl iodide (approx. 5.0 to 10 eq.), is added dropwise to a mixture of a phenol derivative (1.0 eq.) and potassium carbonate (2.0 eq.) in absolute tetrahydrofuran (approx. 0.1 mol/l). The reaction mixture is heated to reflux (usually overnight) and, after cooling, evaporated to dryness and mixed with water. The product obtained after filtration and drying under high vacuum is further purified where appropriate by crystallization from dichloromethane/diethyl ether mixtures or by preparative thin-layer chromatography (dichloromethane/methanol mixtures).

General Method (12)

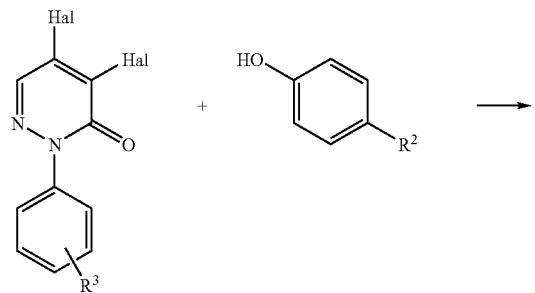

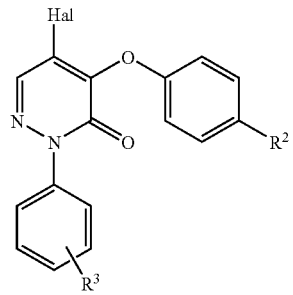

Sodium hydride (1.0 eq., 60% in mineral oil) is introduced in portions into a water-cooled solution of a phenol derivative (1.0 eq.) in absolute 1,4-dioxane (0.4 mol/l) while stirring vigorously (an inverse procedure is advisable for larger batches). After 1 h the solution is added at room temperature to a suspension of a 4,5-dihalopyridazin-3-one derivative (1.0 eq.) in absolute 1,4-dioxane (0.4 mol/l). The reaction mixture is stirred vigorously at room temperature for 15-20 h before the dioxane is almost completely removed in vacuo. The residue is taken up in dichloromethane, washed with water and saturated sodium chloride solution, dried over magnesium sulfate and concentrated. The product is obtained from the mixture by crystallization from dichloromethane or by chromatography on silica gel (dichloromethane/cyclohexane mixtures).

General Method (13)

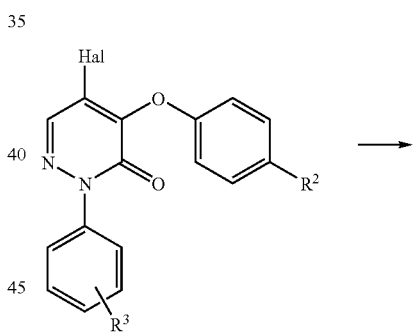

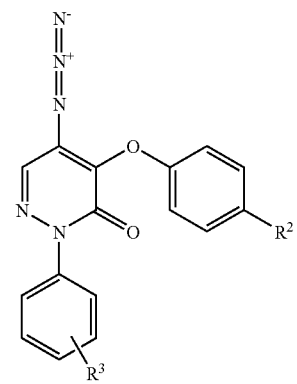

A suspension of a 5-halopyridazin-3-one derivative (1.0 eq., see method 12 for preparation) and sodium azide (5.0 eq.) in dimethylformamide (0.5 mol/l) is heated at 50-55° C. for 30 to 45 min. Cooling is followed by dilution with dichloromethane, washing with water and saturated sodium chloride solution, drying over magnesium sulfate and cautiously concentrating. The residue dried under high vacuum is crystallized using dichloromethane/diethyl ether.

General Method (14)

(Method for 1,2,3-triazole synthesis)

Example:

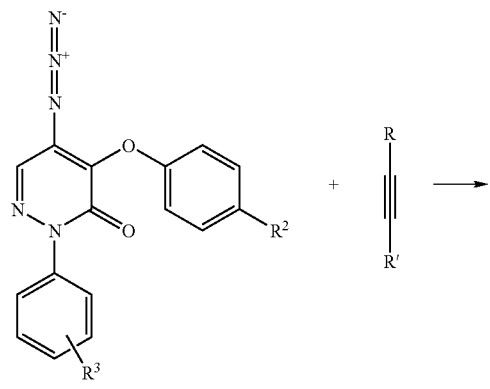

General Method (15)

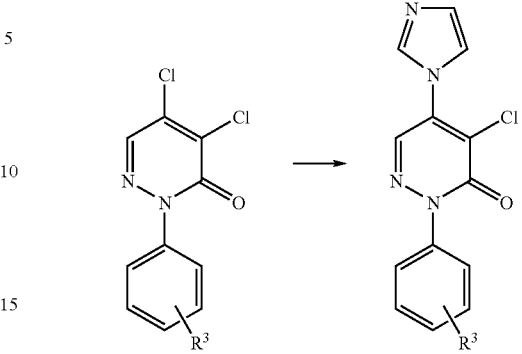

Variant (15a), 4-chloro-5-(1H-imidazol-1yl)-2-aryl-3(2H)-pyridazinones:

25 mmol of 4,5-dichloro-2-aryl-2(3H)-pyridazinone, 75 mmol of imidazole and 0.7 mmol of sodium iodide in 100-150 ml of dimethylformamide are stirred at 90° C. for 8 h (TLC check). Cooling to room temperature is followed by dilution with water and extraction several times with dichloromethane. The organic phase is washed with water and dried over sodium sulfate. The crude product remaining after concentration in a rotary evaporator is chromatographed on silica gel (0.063-0.2 mm). Excess precursor is initially eluted with dichloromethane; the desired product is obtained by elution with petroleum ether/ethyl acetate 1:1. Evaporation results in the appropriate 4-chloro-5-(1H-imidazol-1-yl)-2-aryl-3(2H)-pyridazinones.

Variant (15b), 4-bromo-5-(1H-imidazol-1-yl)-2-aryl-3(2H)-pyridazinones:

On use of 4,5-dibromo-2-aryl-2(3H)-pyridazinones, the corresponding 4-bromo derivatives are obtained in analogy to method (19a).

The appropriate 4,5-dibromo- and 4,5-dichloro-2-aryl-2(3H)-pyridazinones are known or can be prepared by known processes from commercially available arylhydrazines and mucobromic or mucochloric acid under acidic conditions [H. R. Hensel and G. Lützel, Angewandte Chemie 77, 303 (1965)].

General Method (16)

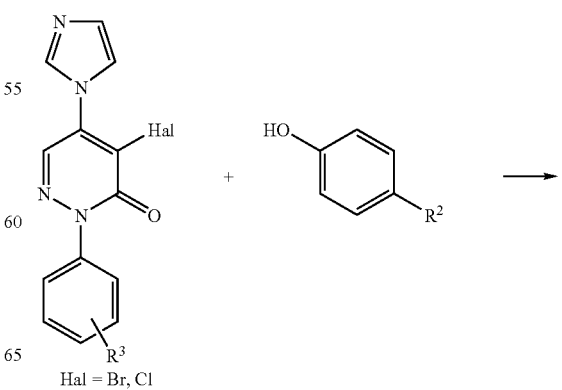

Hal = Br, Cl

A suspension of 5-azidopyridazin-3-one derivative (1.0 eq., see method 13 for preparation) and of a mono- or disubstituted alkyne derivative (2.0 to 8.0 eq.) in toluene (0.1 to 0.4 mol/l) is heated to reflux (2 to 24 h). After cooling, the reaction mixture is concentrated and the product mixture is separated into the regioisomers which have been produced where appropriate, and purified, by crystallization from diethyl ether or diethyl ether/dichloromethane mixtures and chromatography on silica gel (dichloromethane/methanol mixtures).

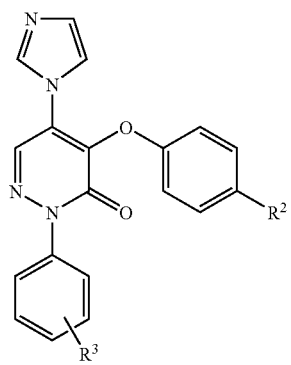

Variant (16a):

10 mmol of 4-chloro- or 4-bromo-5-(1H-imidazol-1-yl)-2-aryl-3(2H)-pyridazinone, 15.0 mmol of phenol, 0.1 g of sodium iodide and 12 mmol of 1,4-diazabicyclo[2.2.2]octane are taken up in 4-10 ml of dimethylformamide and heated at 100° C. overnight. Cooling is followed by dilution with dichloromethane. The organic phase is washed with dilute hydrochloric acid (pH 3), water, 1 N sodium hydroxide solution and water. The residue remaining after drying over sodium sulfate and concentrating is stirred with diethyl ether/methanol 95:5. Purification by chromatography (silica gel 0.063-0.2 mm, dichloromethane/methanol 40:1) of the mother liquor results in further target compound.

Variant (16b):

1,4-Diazabicyclo[2.2.2]octane can be replaced by sodium hydride.

Variant (16c):

1,4-Diazabicyclo[2.2.2]octane can be replaced by sodium methoxide. The sodium salt is formed in analogy to method (6a) beforehand, and the solvent is concentrated.

General Method (17)

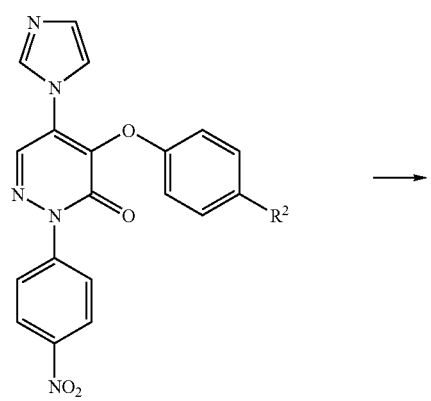 

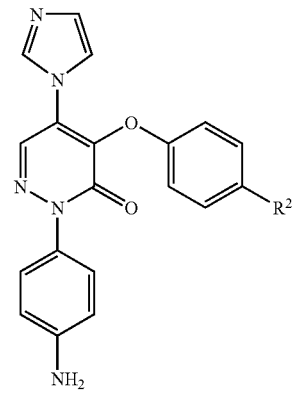

1.1 mmol of 2-(4-nitrophenyl)-5-(1H-imidazol-1-yl)-4-aryloxy-3(2H)-pyridazinone in 50 ml of glacial acetic acid are hydrogenated in the presence of 0.05 g of palladium on activated carbon (10%) at room temperature under 3 bar. After 4 hours, the catalyst is filtered off, and the filtrate is concentrated and taken up in dichloromethane. The organic phase is washed with 1 N sodium bicarbonate solution and water. After drying and concentration, the desired 2-(4-aminophenyl)-3(2H)-pyridazinone is obtained by chromatography on silica gel (0.063-0.2 mm, ethyl acetate).

The products obtained from the general preparation processes can be treated with solutions of hydrogen chloride in inert solvents to obtain the corresponding hydrochlorides.

STARTING COMPOUND AND INTERMEDIATES

Example 1A tert-Butyl 4-[5-chloro-1-(4-chlorophenyl)-6-oxo-1,6-dihydro-4-pyridazinyl]-1-piperazine carboxylate

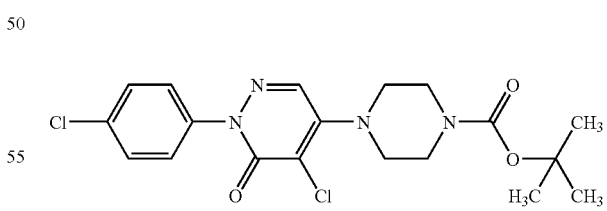

By general method 1 from 20.66 g (75 mmol) of 2-(4-chlorophenyl)-4,5-dichloropyridazin-3-one with 25.14 g (135 mmol) of Boc-piperazine.

Yield: 25.22 g (79.1% of theory) MS (Method A): m/z=442 (M+NH$_4$)$^+$, 425 (M+H)$^+$ HPLC: R$_t$=9.51 min.

Example 2A

4-Chloro-2-(4-chlorophenyl)-5-(1-piperazinyl)-3(2H)-pyridazinone

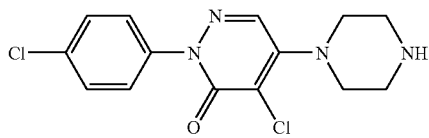

55.1 g (200 mmol) of 2-(4-chlorophenyl)-4,5-dichlorpyridazin-3-one are introduced with 41.6 ml (300 mmol) of triethylamine in 400 ml of dimethylformamide. 137.82 g (1600 mmol) of piperazine are added, and the mixture is stirred at 80° C. overnight. The reaction mixture is cooled and then concentrated under high vacuum. The residue is taken up in dichloromethane and washed twice with water, dried over magnesium sulfate and concentrated. The product is isolated by chromatography (gradient: dichloromethane/methanol from 95:5 to 9:1) on silica gel and subsequent crystallization with ether.

Yield: 40.9 g (62.9% of theory) MS (Method A): m/z=325 (M+H)$^+$ HPLC: R$_t$=5.38 min.

Example 3A 5-(4-Acetyl-1-piperazinyl)-4-chloro-2-(4-chlorophenyl)-3(2H-pyridazinone

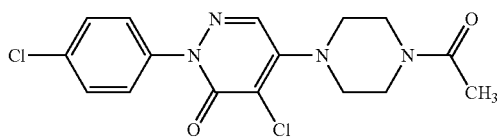

Obtainable by general method 2 from 9.76 g (30 mmol) of the compound from Example 2A with 5.7 ml (60 mmol) of acetic anhydride.

Yield: 10.6 g (96.2% of theory) MS (Method B): m/z=367 (M+H)$^+$ HPLC: R$_t$=7.01 min.

Example 4A 5-(4-Acetyl-1-piperazinyl)-4-chloro-2-(4-methylphenyl)-3(2H)-pyridazinone

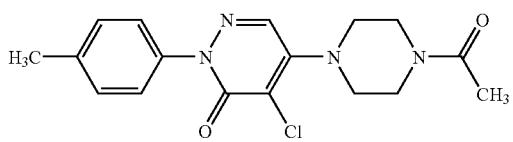

Obtainable by general method 1 from 10.0 g (39.2 mmol) of 2-(4-chlorophenyl)-4,5-dichloropyridazin-3-one with 8.2 g (64 mmol) of N-acetylpiperazine.

Yield: 7.86 g (57.8% of theory) MS (Method F): m/z=347 (M+H)$^+$ HPLC: R$_t$=6.67 min.

Example 5A

4-Chloro-2-(4-chlorophenyl)-5-[4-(cyclopropylcarbonyl)-1-piperazinyl]-3(2H)-pyridazinone

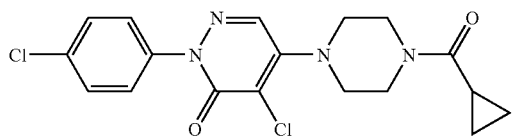

Obtainable by general method 2 from 9.76 g (30.0 mmol) of the compound from Example 2A with 3.3 ml (36 mmol) of cyclopropylcarbonyl chloride.

Yield: 11.22 g (95.1% of theory) MS (Method F): m/z=393 (M$^+$) HPLC: R$_t$=7.72 min.

Example 6A

4-Chloro-2-(4-chlorophenyl)-5-[4-(methylsulfonyl)-1-piperazinyl]-3(2H)-pyridazinone

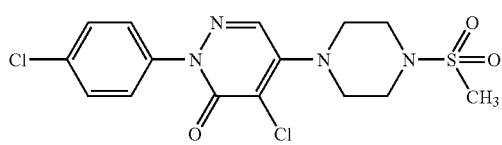

Obtainable by general method 4 from 10.0 g (30.75 mmol) of the compound from Example 2A with 3.6 ml (46.1 mmol) of methanesulfonyl chloride.

Yield: 11.1 g (89.5% of theory) MS (APCI): m/z=403 (M+H)$^+$ HPLC: R$_t$=7.81 min.

Example 7A

4-Chloro-2-(4-chlorophenyl)-5-(3-oxo-1-piperazinyl)-3(2H)-pyridazinone

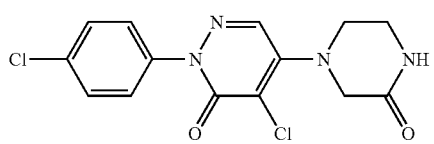

Obtainable by general method 1 from 4.68 g (17 mmol) of 2-(4-chlorophenyl)-4,5-dichloropyridazin-3-one with 3.06 g (30.6 mmol).

Yield: 3.51 g (60.9% of theory) MS (EI-POS): m/z=338 (M$^+$) HPLC: R$_t$=6.42 min.

Example 8A 4,5-Bis(1,1'-biphenyl-4-yloxy)-2-(4-chlorophenyl)-3 (2H)-pyridazinone

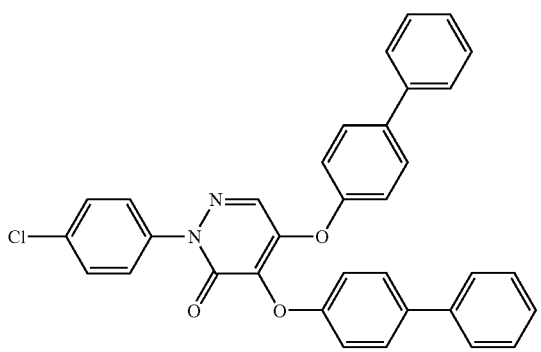

68.09 g (400 mmol) of biphen-4-ol are added in portions to a solution of 44.9 g (400 mmol) of potassium tert-butoxide in 680 ml of absolute tetrahydrofuran. After 15 min, the solution is concentrated and thoroughly dried under high vacuum. 27.3 g (100 mmol) of 2-(4-chlorophenyl)-4,5-dichlorpyridazin-3-one, 8.30 g (50 mmol) of potassium iodide and 300 ml of absolute dimethylformamide are added, and the mixture is heated at 140° C. while stirring vigorously for 4 h. Cooling is followed by concentration under high vacuum, and the residue is taken up in dichloromethane. The suspension is filtered through Celite and the filtrate is washed twice with 1 N sodium hydroxide solution. The organic phase is dried over magnesium sulfate and concentrated. The product is isolated by filtration through a silica gel column (dichloromethane/cyclohexane 3:1).

Yield: 10.20 g (18.8% of theory)

MS (Method B): m/z=543 (M+H)$^+$ HPLC: R$_t$=11.85 min.

Example 9A 4-(1,1'-Biphenyl-4-yloxy)-5-chloro-2-(4-chlorophenyl)-3(2H)-pyridazinone

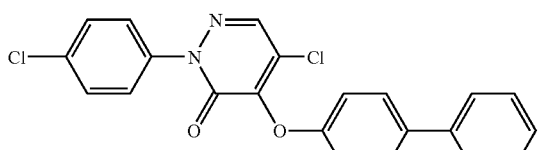

Obtainable by general method 12 from 22.04 g (80.0 mmol) of 2-(4-chlorophenyl)-4,5-dichloropyridazin-3-one.

Yield: 19.54 g (59.7% of theory) MS (Method B): m/z=409 (M+H)$^+$ HPLC: R$_t$=10.95 min.

Example 10A 4-(4-Bromophenoxy)-5-chloro-2-(4-chlorophenyl)-3 (2H)-pyridazinone

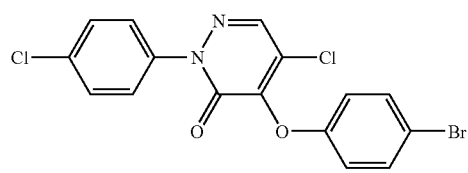

Obtainable by general method 12 from 27.55 g (100.0 mmol) of 2-(4-chlorophenyl)-4,5-dichloropyridazin-3-one.

MS (Method B): m/z=428/430 (M+NH$_4$)$^+$ HPLC: R$_t$=10.48 min.

Example 11A

5-Bromo-2-(4-chlorophenyl)-4-[(4'-fluoro-1,1'-biphenyl-4-yl)oxy]-3(2H)-pyridazinone

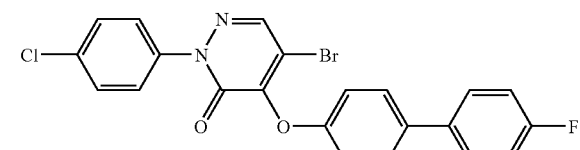

Obtainable by general method 12 from 2-(4-chlorophenyl)-4,5-dibromopyridazin-3-one.

HPLC: R$_t$=10.96 min.

Example 12A

5-Chloro-2-(4-chlorophenyl)-4-{[4'-fluoro-2'-(methoxymethoxy)-1,1'-biphenyl-4-yl]-oxy}-3(2H)-pyridazinone

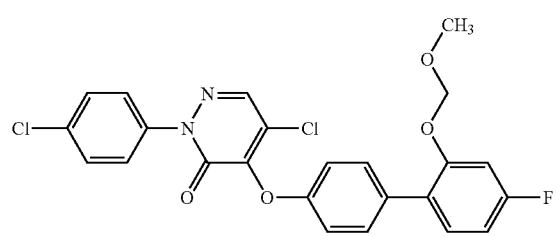

Obtainable by general method 12 from 1.82 g (6.6 mmol) of 2-(4-chlorophenyl)-4,5-dichloropyridazin-3-one.

Yield: 1.84 g (57.3% of theory) MS (Method A): m/z=487/489 (M+H)$^+$ HPLC: R$_t$=10.91 min.

Example 13A

5-Chloro-2-(4-chlorophenyl)-4-[(2',4'-difluoro-1,1'-biphenyl-4-yl)oxy]-3(2H)-pyridazinone

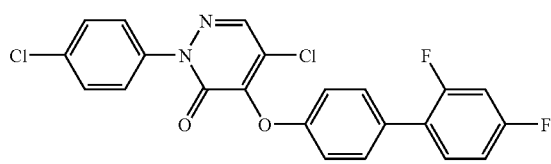

Obtainable by general method 12 from 5.51 g (20.0 mmol) of 2-(4-chlorophenyl)-4,5-dichloropyridazin-3-one.

Yield: 5.07 g (56.9% of theory) MS (Method A): m/z=462 (M+N)$^+$ HPLC: R$_t$=10.97 min.

Example 14A

5-Azido-4-(1,1'-biphenyl-4-yloxy)-2-(4-chlorophenyl)-3(2H)-pyridazinone

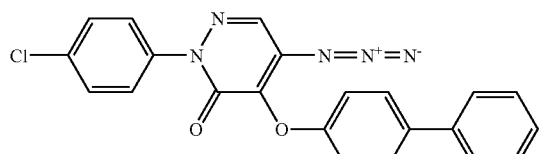

Obtainable by general method 13 from 2.05 g (5.0 mmol) of the compound from Example 9A with 1.63 g (25.0 mmol) of sodium azide.

Yield: 0.998 g (48.0% of theory) MS (Method B): m/z=416 (M+H)$^+$ HPLC: R$_t$=10.74 min.

Example 15A

5-Azido-4-(4-bromophenoxy)-2-(4-chlorophenyl)-3(2H)-pyridazinone

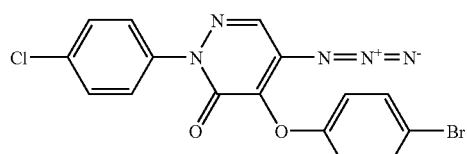

Obtainable by general method 13 from 7.55 g (18.3 mmol) of the compound from Example 10A with 5.96 g (91.6 mmol) of sodium azide.

Yield: 3.73 g (48.6% of theory) MS (Method A): m/z=435/437 (M+H)$^+$ HPLC: R$_t$=10.25 min.

Example 16A

5-Azido-2-(4-chlorophenyl)-4-[(4'-fluoro-1,1'-biphenyl-4-yl)oxy]-3(2H)-pyridazinone

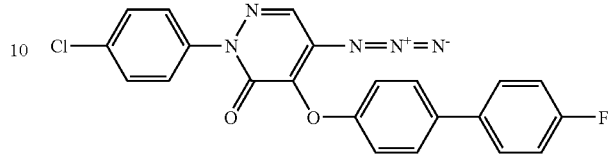

Obtainable by general method 13 from 800 mg (1.70 mmol) of the compound from Example 11A.

Yield: 455 mg (55.7% of theory) MS (Method A): m/z=451 (M+NH$_4$)$^+$, 434 (M+H)$^+$ HPLC: R$_t$=10.70 min.

Example 17A

5-Azido-2-(4-chlorophenyl)-4-{[4'-fluoro-2'-(methoxymethoxy)-1,1'-biphenyl-4-yl]-oxy}-3(2H)-pyridazinone

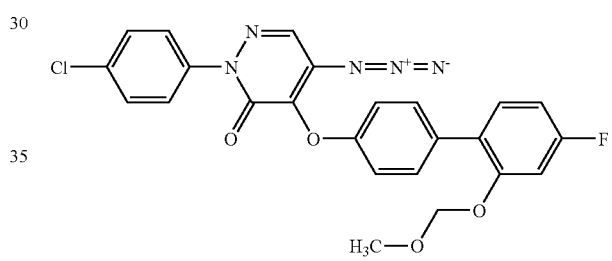

Obtainable by general method 13 from 305 mg (0.626 mmol) of the compound from Example 12A.

Yield: 118 mg (38.2% of theory) MS (Method D): m/z=494 (M+H)$^+$ HPLC: R$_t$=10.74 min.

Example 18A

5-Azido-2-(4-chlorophenyl)-4-[(2',4'-difluoro-1,1'-biphenyl-4-yl)oxy]-3(2H)-pyridazinone

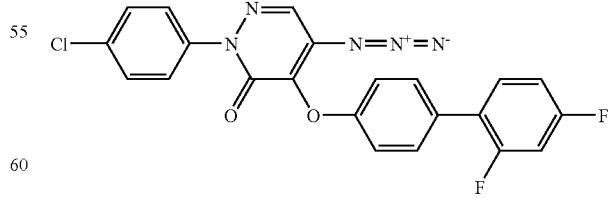

Obtainable by general method 13 from 890.5 mg (2.0 mmol) of the compound from Example 13A.

Yield: 379 mg (37.7% of theory) MS (Method D): m/z=452 (M+H)$^+$ HPLC: R$_t$=10.77 min.

Example 19A 4-(tert-Butoxycarbonyl)-R-(−)-2-methylpiperazine

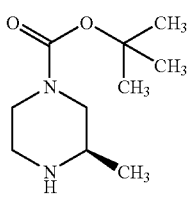

8.49 g (37.74 mmol) of di-tert-butyl pyrocarbonate and catalytic amounts of 4-dimethylaminopyridine are added to a solution of 3.6 g (35.94 mmol) of R-(−)-2-methylpiperazine in 50 ml of tetrahydrofuran, and the mixture is stirred at room temperature for 24 h. It is evaporated to dryness, taken up in dichloromethane and washed three times with water and once with sodium chloride solution, and the organic phase is concentrated.

Yield: 4.62 g (64.2% of theory) MS (Method A): m/z=318 $(M_2+H)^+$ DC: $R_f$=0.29 (dichoromethane/methanol 9:1)

Example 20A 4-(tert-Butoxycarbonylamino)-1-carboethoxypiperidine

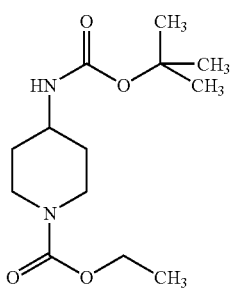

26.13 g (119.72 mmol) of di-tert-butyl pyrocarbonate and catalytic amounts of 4-dimethylaminopyridine are added to a solution of 10.2 g (58.06 mmol) of 4-amino-1-carbethoxypiperidine in 250 ml of tetrahydrofuran at 0° C. The mixture is allowed to reach room temperature and then stirred for 2 h. The reaction solution is concentrated, and the residue is dissolved in dichloromethane and washed with water and sodium chloride solution. The organic phase is concentrated and dried under high vacuum.

Yield: 20.2 g (127.7% d of theory, product contains solvent) MS (Method A): m/z=290 $(M+NH_4)^+$, 273 $(M+H)^+$

Example 21A 4-(tert-Butoxycarbonylamino)piperidine

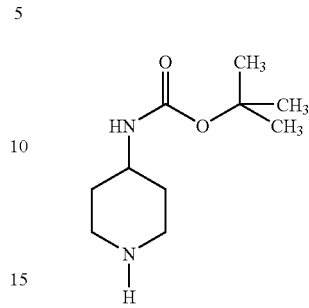

19.91 g (0.073 mol) of the compound from Example 20A are added to a mixture of 32.33 g (0.576 mol) of KOH in 175 ml of water and 175 ml of ethanol and heated to reflux for 4 h. The reaction solution is then stirred at room temperature overnight, diluted with 350 ml of conc. sodium chloride solution and extracted four times with a total of 1500 ml of ethyl acetate. The organic extract is washed four times with 100 ml of sodium chloride solution each time, dried over sodium acetate, concentrated and dried under-high vacuum.

Yield: 11.49 g (89.2% of theory) MS (Method A): m/z=201 $(M+H)^+$

Example 22A

2-Chloro-2-(4-chlorophenyl)-5-(1,4-dioxa-8-azaspiro[4.5]dec-8-yl)-2H-pyridazin-3-one

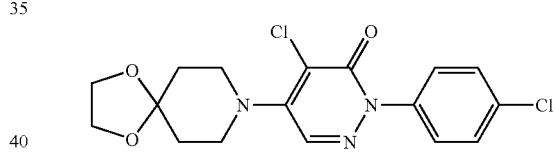

25.98 g (0.181 mol) of piperidinone 4-ethylene ketal 1.023 g (6.82 mmol) of sodium iodide are successively added to a solution of 20.0 g (72.59 mmol) of 4,5-dichloro-2-(4-chlorophenyl)-2-(3H)-pyridazinone in 200 ml of N-methyl-2-pyrrolidine and stirred at 65° C. for 4 h and at room temperature overnight. The reaction mixture is stirred into a large amount of water, and the precipitated product is filtered off with suction. The residue on the filter is stirred in ether, filtered off with suction and dried in vacuo.

Yield: 25.36 g (91.4% of theory) MS (Method B): m/z=382 $(M+H)^+$ HPLC: $R_t$=8.49 min.

Example 23A tert-Butyl 4-[5-chloro-1-(4-chlorophenyl)-6-oxo-1,6-dihydropyridazin-4-yl]-3-methylpiperazine-1-carboxylate

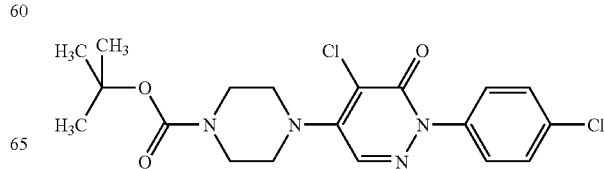

By general method 1c, 15.47 g (80.6 mmol) of tert-butyl piperazine-1-carboxylate and 0.22 g (1.49 mmol) of sodium iodide are added to a suspension of 10.09 g (30.3 mmol) of 2-(4-chlorophenyl)-4,5-dichloro-2(3H)-pyridazinone in 1000 ml of dioxane and stirred at 100° C. overnight. Dioxane is distilled off, and the residue is dissolved in dissolved in 200 ml of dichloromethane and 150 ml of water. The organic phase is dried, concentrated and stirred with 200 ml of ether for 1 h. The crystals are filtered off with suction, washed with ether and dried in vacuo.

Yield: 9.6 g (62.2% of theory) MS (EI): m/z=424(M$^+$) HPLC: R$_t$=9.54 min.

Example 24A 4-(4-Bromophenoxy)-2-(4-chlorophenyl)-5-[4-(2-hydroxyethyl)-1-piperazinyl]-3(2H)-pyridazinone

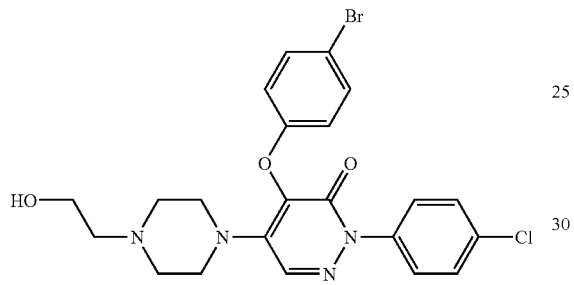

1.35 ml (18.11 mmol) of 2-bromoethanol are added dropwise to a mixture of 4.18 (9.05 mmol) of 4-(4-bromophenoxy)-2-(4-chlorophenyl)-5-(1-piperazinyl)-3(2H)-pyridazinone (Example 57A), 0.15 g of potassium iodide 3.75 g (27.2 mmol) of potassium carbonate in 25 ml of 1,4-dioxane. Stirring under reflux overnight is followed by dilution with dichloromethane and washing twice with water, drying and concentration. Purification is by flash chromatography on silica gel (gradient: dichloromethane/methanol from 99:1 to 97:3).

Yield: 3.5 g (76.4% of theory) MS (Method A): m/z=505/507 (M+H)$^+$ HPLC: R$_t$=6.87 min.

The following intermediates are obtained by general method 8:

Example 25A 2-(4-Chlorophenyl)-5-(1H-imidazol-1-yl)-4-[4-(4,4,5,5-tetramethyl-1,3,2-dioxaborolan-2-yl)phenoxy]-3(2H)-pyridazinone

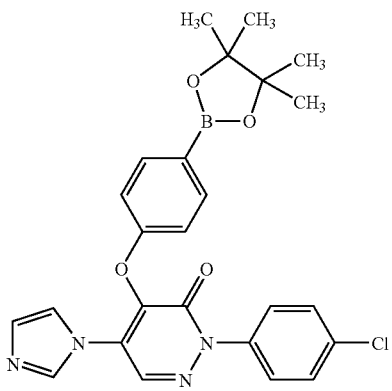

MS (Method C): m/z=490 (M$^+$) HPLC: R$_t$=6.31 min.

Example 26A 2-(4-Chlorophenyl)-5-[4-(2-hydroxyethyl)-1-piperazinyl]-4-[4-(4,4,5,5-tetramethyl-1,3,2-dioxaborolan-2-yl)phenoxy]-3(2H)-pyridazinone

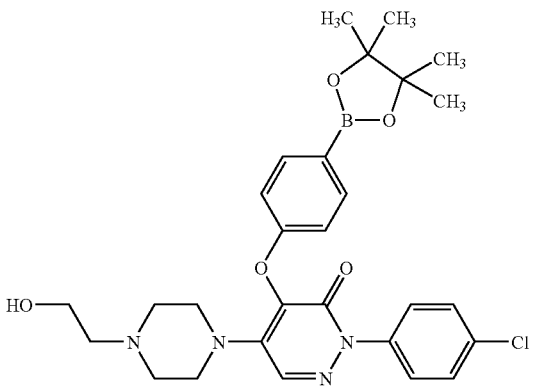

MS (Method B): m/z=553 (M+H)$^+$ HPLC: R$_t$=7.42 min.

The intermediates Example 27A-Example 37A listed in Table 5 were prepared by general process 15a:

| Example No. | Structure | Physical data | Precursor |
|---|---|---|---|
| 27A | 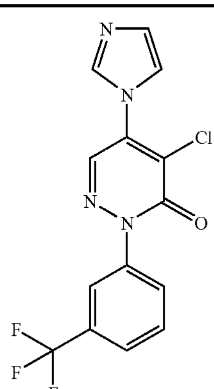 | m.p.: 101° C. | 4,5-Dichloro-2-(3-trifluoromethylphenyl)-(3H)-pyridazinone |

-continued
| Example No. | Structure | Physical data | Precursor |
|---|---|---|---|
| 28A | 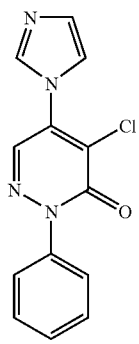 | m.p.: 162° C. | 4,5-Dichloro-2-phenyl-(3H)-pyridazinone |
| 29A | 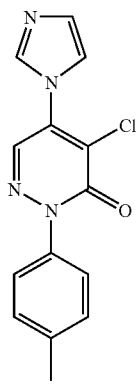 | m.p.: 157° C. | 4,5-Dichloro-2-(4-methylphenyl)-(3H)-pyridazinone |
| 30A | 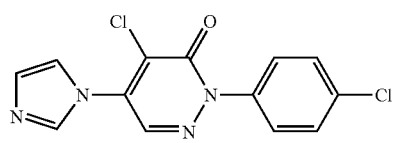 | m.p.: 175° C. | 4,5-Dichloro-2-(4-chlorophenyl)-(3H)-pyridazinone |
| 31A | 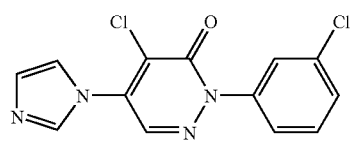 | m.p.: 176° C. | 4,5-Dichloro-2-(3-chlorophenyl)-(3H)-pyridazinone |
| 32A | 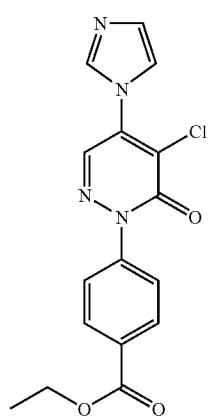 | m.p.: 149° C. | 4,5-Dichloro-2-(4-ethoxycarbonylphenyl)-(3H)-pyridazinone |

-continued

| Example No. | Structure | Physical data | Precursor |
|---|---|---|---|
| 33A | 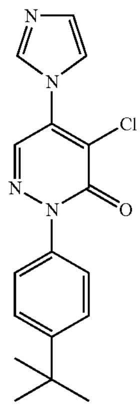 | m.p.: 170–3° C. | 2-[4-(tert-Butyl)phenyl]-4,5-dichloro-3(2H)-pyridazinone |
| 34A | 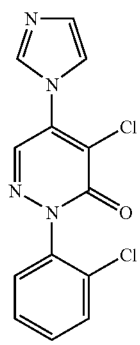 | m.p.: 139–41° C. | 4,5-Dichloro-2-(2-chlorophenyl)-(3H)-pyridazinone |
| 35A | 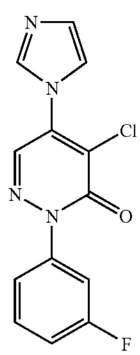 | m.p.: 122° C. | 4,5-Dichloro-2-(3-fluorophenyl)-(3H)-pyridazinone |
| 36A | 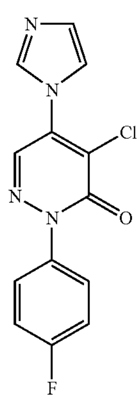 | m.p.: 181° C. | 4,5-Dichloro-2-(4-fluorophenyl)-(3H)-pyridazinone |

-continued

| Example No. | Structure | Physical data | Precursor |
|---|---|---|---|
| 37A | (structure) | | 4,5-Dichloro-2-(4-nitrophenyl)-(3H)-pyridazinone |

The intermediates Example 38A-Example 63A listed in Table 6 were obtained general process 6a:

| Example No. | Structure | Physical data (data in °C. relate to the melting point) | General process | Starting material |
|---|---|---|---|---|
| 38A | (structure) | 182° C. | 16a | Example No. 30A; 4-Bromophenol |
| 39A | (structure) | MS (A): 423 (M + H) (100) | 16a | Example No. 29A; 4-Bromophenol |

-continued

| Example No. | Structure | Physical data (data in ° C. relate to the melting point) | General process | Starting material |
|---|---|---|---|---|
| 40A | 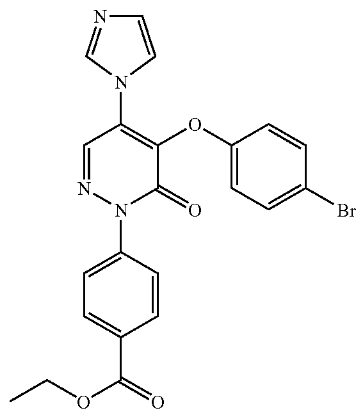 | 155–7° C. | 16a | Example No. 32A; 4-Bromophenol |
| 41A | 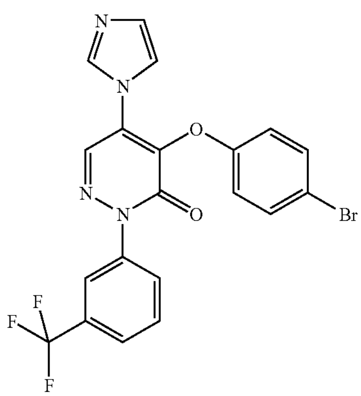 | 168–70° C. | 16a | Example No. 27A; 4-Bromophenol |
| 42A | 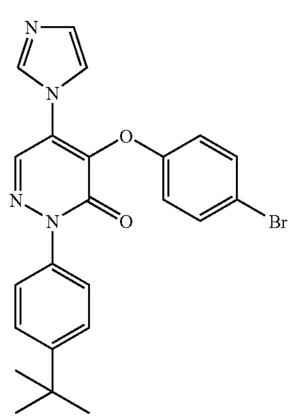 | 225° C. | 16a | Example No. 33A; 4-Bromophenol |

-continued

| Example No. | Structure | Physical data (data in ° C. relate to the melting point) | General process | Starting material |
|---|---|---|---|---|
| 43A | 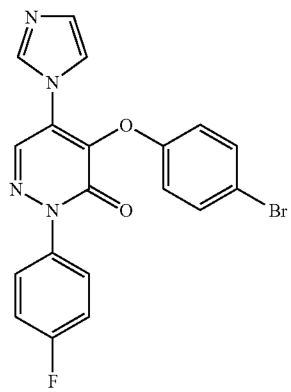 | 185–190° C. | 16a | Example No. 36A; 4-Bromophenol |
| 44A | 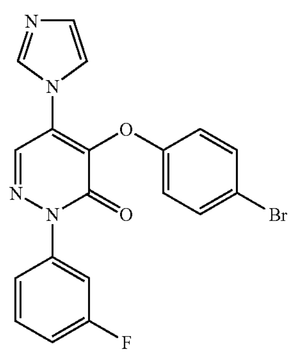 | 180–185° C. | 16a | Example No. 35A; 4-Bromophenol |
| 45A | 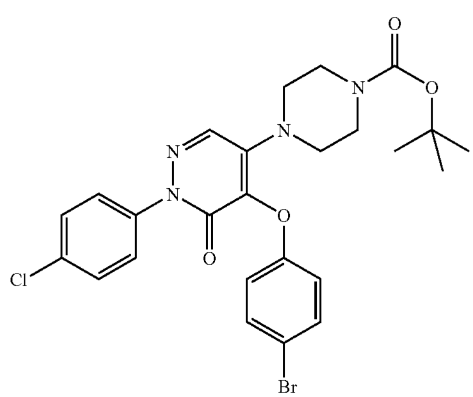 | MS (A): 561/563 (M + H) (100); HPLC: 10.64 (94) | 6-a | Example No. 23A; 4-Bromophenol |
| 46A | 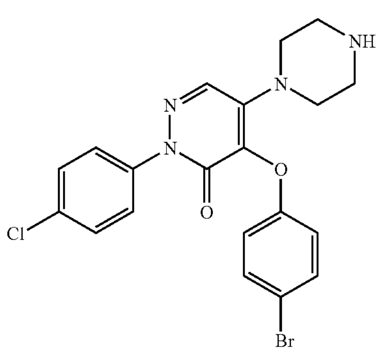 | MS (B): 462/463 (M + H) (100); HPLC: 6.72 (98) | 7 | Example No. 45A |

-continued

| Example No. | Structure | Physical data (data in °C. relate to the melting point) | General process | Starting material |
|---|---|---|---|---|
| 47A | 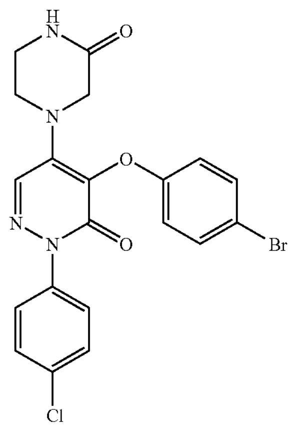 | MS (B): 475/477 (M + H) (100); HPLC: 7.98 (100) | 6-a | Example No. 7A; 4-Bromophenol |
| 48A | 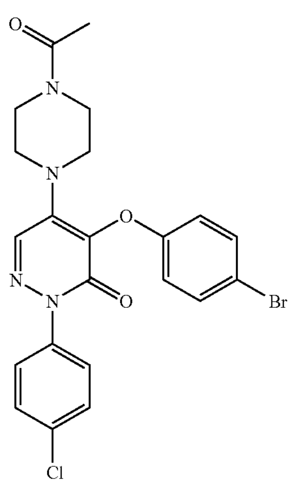 | MS (B): 503/505 (M + H); HPLC: 8.48 (91) | 6-b | Example No. 3A; 4-Bromophenol |
| 49A | 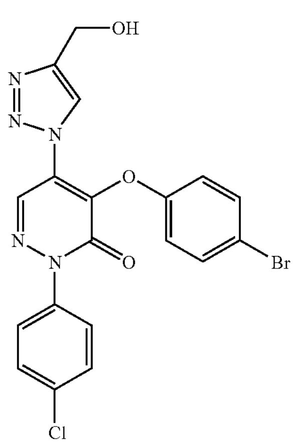 | MS (B): 474/476 (M + H) (100); HPLC: 8.78 (100) | 14 | Example No. 15A; Propargyl alcohol |

-continued
| Example No. | Structure | Physical data (data in ° C. relate to the melting point) | General process | Starting material |
|---|---|---|---|---|
| 50A | 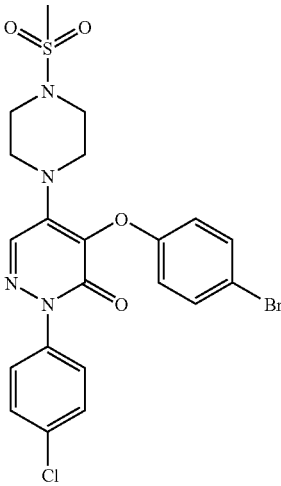 | MS (B): 539/541 (M + H) (100); HPLC: 9.16 (98) | 6-b | Example No. 6A; 4-Bromophenol |
| 51A | 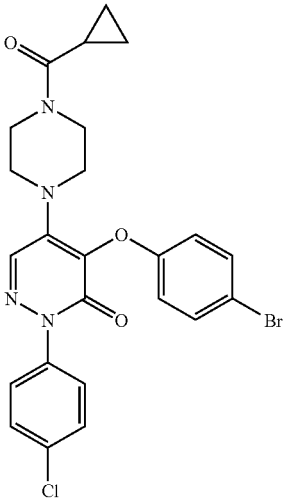 | MS (D): 529/531 (M + H) (100); HPLC: 9.12 (93) | 6-b | Example No. 5A; 4-Bromophenol |
| 52A | 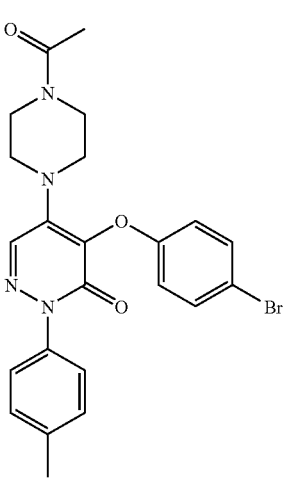 | MS (A): 483/485 (M + H) (100); HPLC: 8.16 (94) | 6-b | Example No. 4A; 4-Bromophenol |

-continued

| Example No. | Structure | Physical data (data in ° C. relate to the melting point) | General process | Starting material |
|---|---|---|---|---|
| 53A | 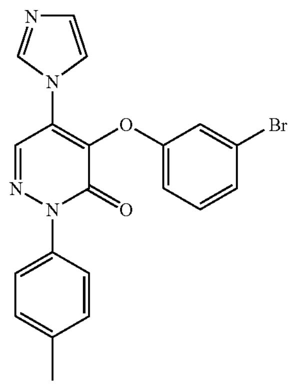 | MS (A): 423 (M + H) (100) | 16a | Example No. 29A; 3-Bromophenol |
| 54A | 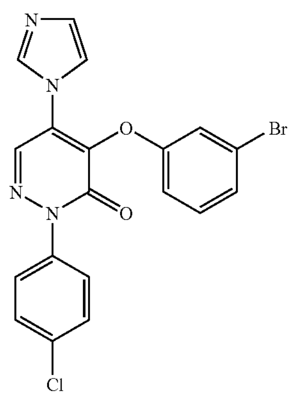 | 83–86° C. | 16a | Example No. 30A; 3-Bromophenol |
| 55A | 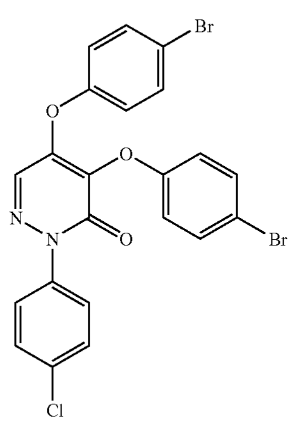 | MS (A): 566 (M + NH$_4$) (100); HPLC: 8.98 (100) | 12 | 2-(4-Chlorophenyl)-4,5-dichloro-pyridazinone; 4-bromophenol |

-continued

| Example No. | Structure | Physical data (data in °C. relate to the melting point) | General process | Starting material |
|---|---|---|---|---|
| 56A | 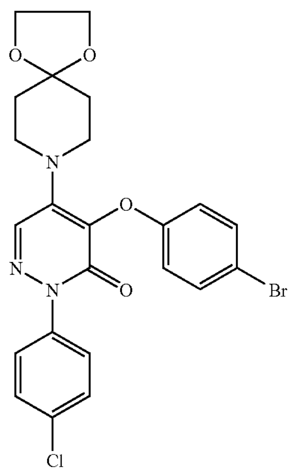 | MS (D): 382 (M + H) (87); HPLC: 9.16 (92) | 16a | Example No. 22A; 4-Bromophenol |
| 57A | 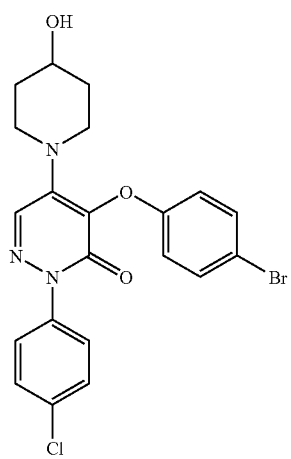 | MS (A): 478 (M + H) (100); HPLC: 8.65 (93) | 1; 16a | 2-(4-Chlorophenyl)-4,5-dichloro-pyridazinone; 4-hydroxy-piperidine; 4-bromophenol |
| 58A | 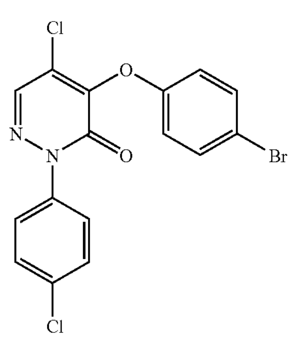 | MS (A): 428 (M + NH$_4$) (100); HPLC: 10.48 (99) | 12 | 2-(4-Chlorophenyl)-4,5-dichloro-pyridazinone; 4-bromophenol |

-continued

| Example No. | Structure | Physical data (data in °C. relate to the melting point) | General process | Starting material |
|---|---|---|---|---|
| 59A | 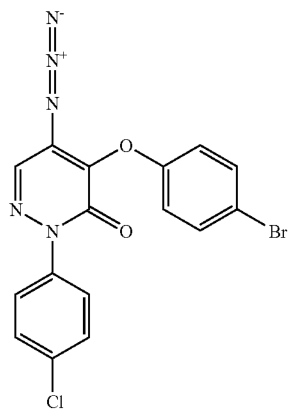 | MS (A): 435 (M + NH$_4$) (100); HPLC: 10.25 (95) | 13 | Example No. 10A |
| 60A | 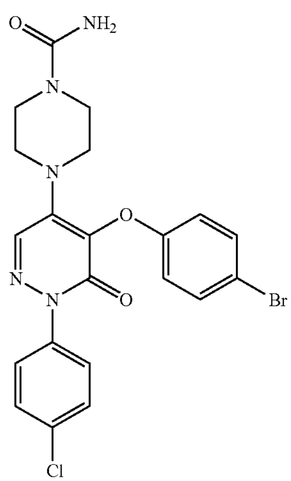 | MS (C): 506 (M + H) (100); HPLC: 7.93 (92) | 5 | Example No. 46A |
| 61A | 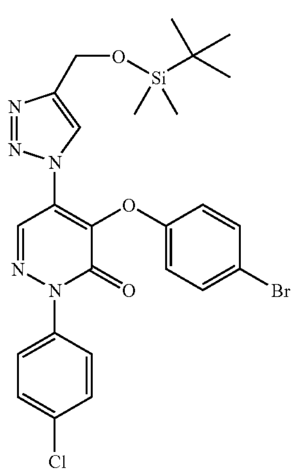 | MS (C): 590 (M + H) (100); HPLC: 12.25 (95) | 14 | Example No. 59A; 1-(tert-Butyl-dimethylsilyloxy)-prop-2-yne |

| Example No. | Structure | Physical data (data in °C. relate to the melting point) | General process | Starting material |
|---|---|---|---|---|
| 62A | 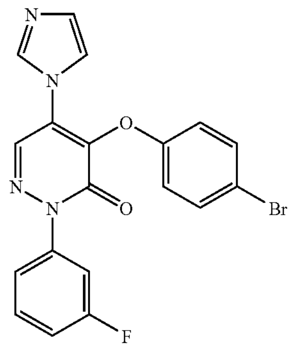 | crude reacted further | 16a | Example No. 35A; 4-Bromophenol |
| 63A | 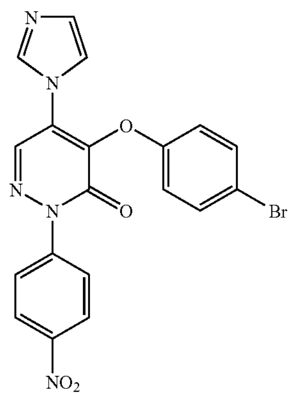 | crude reacted further | 16a | Example No. 37A; 4-Bromophenol |

EXEMPLARY EMBODIMENTS

Example 1

N-(4'-{[2-(4-Chlorophenyl)-5-(1H-imidazol-1-yl)-3-oxo-2,3-dihydro-4-pyridazinyl]-oxy}-1,1'-biphenyl-2-yl)-N-(methylsulfonyl)methanesulfonamide

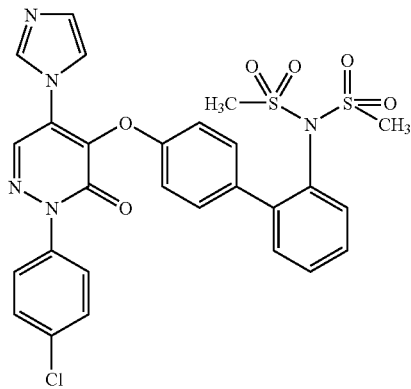

0.06 ml (0.072 mmol) of methanesulfonyl chloride are added dropwise to a mixture of 16.5 mg (0.036 mmol) of 4-[(2'-amino-1,1'-biphenyl-4-yl)oxy]-2-(4-chlorophenyl)-5-(1H-imidazol-1-yl)-3(2H)-pyridazinone (Example 156), 0.02 ml of triethylamine and a catalytic amount of 4-DMAP in 0.2 ml of absolute dichloromethane at room temperature. After 30 min, the reaction is stopped by adding a little water, and the reaction mixture is filtered directly on a silica gel column (mobile phase: dichloromethane/methanol gradient from 99:1 to 98:2).

Yield: 15.3 mg (69.1% of theory) MS (ESI): m/z=612 (M+H)$^+$ HPLC: $R_t$=8.17 min.

Example 2 tert-Butyl 4-[5-({4'-[(2,2-dimethylpropanoyl)oxy]-1,1'-biphenyl-4-yl}oxy)-1-(4-methylphenyl)-6-oxo-1,6-dihydro-4-pyridazinyl]-1-piperazinecarboxylate

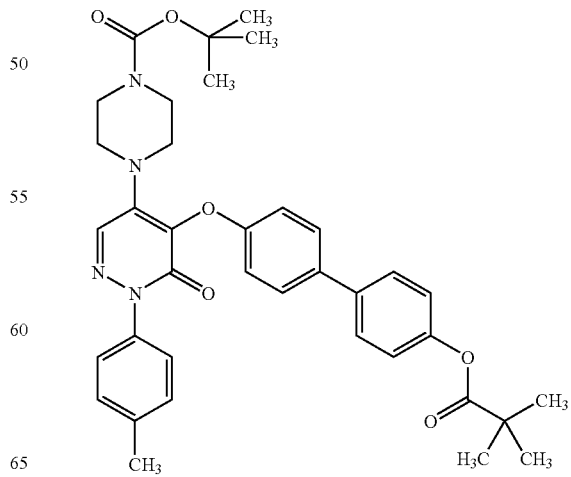

0.66 ml of pivaloyl chloride are added dropwise to a suspension of 728 mg (1.18 mmol) of tert-butyl 4-[5-[(4'-hydroxy-1,1'-biphenyl-4-yl)oxy]-1-(4-methyl-phenyl)-6-oxo-1,6-dihydro-4-pyridazinyl]-1-piperazinecarboxylate (Example 46) and a catalytic amount of 4-DMAP in a mixture of dichloromethane (4.0 ml) and pyridine (0.4 ml) at room temperature. The heterogeneous reaction mixture is stirred at about 40° C. overnight. The slightly cloudy suspension is diluted with dichloromethane and washed with 0.2 N hydrochloric acid solution and saturated sodium chloride solution, dried over magnesium sulfate and concentrated. The crude product is purified by chromatography on silica gel.

Yield: 568 mg (75.3% of theory) MS (ESI): m/z=639 (M+H)+ HPLC: $R_t$=10.21 min.

Example 3

4'-{[2-(4-Methylphenyl)-3-oxo-5-(1-piperazinyl)-2,3-dihydro-4-pyridazinyl]oxy}-1,1'-biphenyl-4-yl pivalate trifluoroacetic acisalt

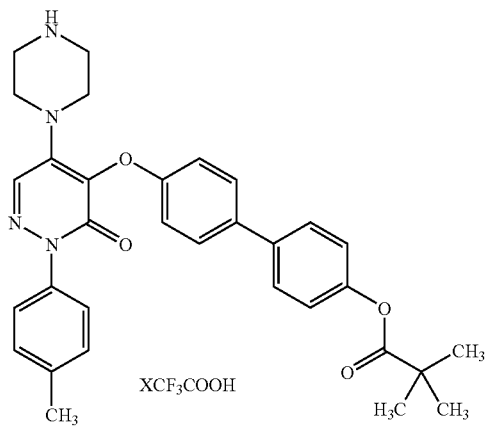

0.2 ml of water and 2.2 ml of trifluoroacetic acid are added dropwise to a solution of 568 mg (0.889 mmol) of the compound from Example 2 in 4.5 ml of dichloromethane at room temperature. After 45 min, the reaction mixture is concentrated and thoroughly dried under high vacuum.

Yield: 702 mg (96.5% of theory) MS (ESI): m/z=539 (M+H)+ (free base).

Example 4

4'-{[5-(4-Ethyl-1-piperazinyl)-2-(4-methylphenyl)-3-oxo-2,3-dihydro-4-pyridazinyl]-oxy}-1,1'-biphenyl-4-yl pivalate

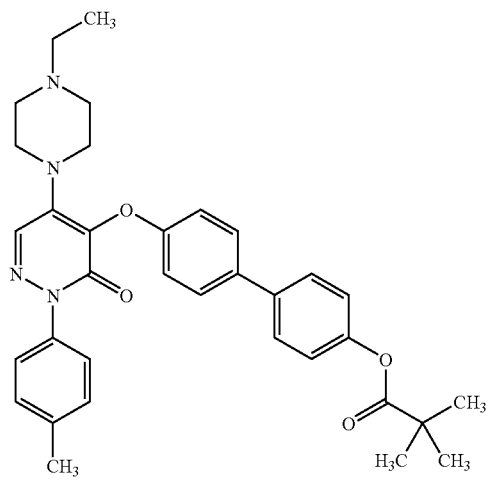

360 mg (0.44 mmol) of the compound from Example 3 are introduced into 2.0 ml of acetone, and 0.046 ml (0.57 mmol) of ethyl iodide and 0.18 ml (1.32 mmol) of triethylamine are successively added. The mixture is stirred at room temperature overnight before being diluted with dichloromethane, washed with saturated sodium bicarbonate solution, dried over magnesium sulfate and concentrated. The crude product is purified by filtration through a silica gel column (mobile phase: dichloromethane/methanol 95:5).

Yield: 211 mg (84.4% of theory) MS (ESI): m/z=567 (M+H)+ HPLC: $R_t$=7.00 min.

Example 5

5-(4-Ethyl-1-piperazinyl)-4-[(4'-hydroxy-1,1'-biphenyl-4-yl)oxy]-2-(4-methylphenyl)-3(2H)-pyridazinone

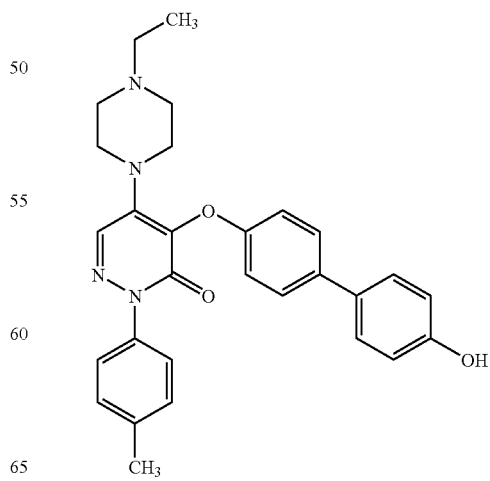

210 mg (0.37 mmol) of the compound from Example 4 are introduced into 4.5 ml of dry methanol. Addition of 0.9 ml of triethylamine is followed by heating to reflux for 24 h. The suspension is concentrated and the resulting colorless solid is dried under high vacuum.

Yield: 134 mg (74.9% of theory) MS (DCI/NH$_3$): m/z=483 (M+H)$^+$ HPLC: R$_t$=6.59 min.

Example 6

4-[(4'-Hydroxy-1,1'-biphenyl-4-yl)oxy]-2-(4-methylphenyl)-5-(4-methyl-1-piperazinyl)-3(2H)-pyridazinone

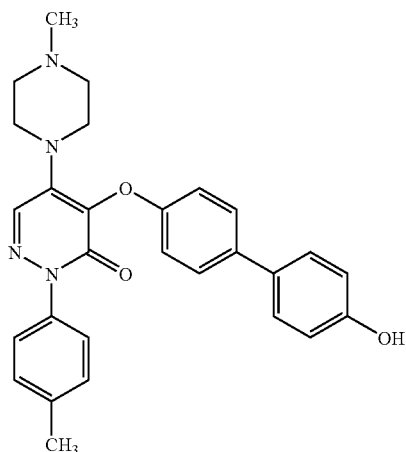

360 mg (0.44 mmol) of the compound from Example 3 are introduced into 2.0 ml of acetone, and an excess of methyl iodide and 0.18 ml of triethylamine are successively added. After the reaction has subsided, the mixture is stirred at room temperature for 1 h before being diluted with dichloromethane. The precipitated solid is filtered off and the filtrate is washed with water, dried over magnesium sulfate and concentrated. The crude product is purified by chromatography on silica gel (mobile phase: dichloromethane/methanol 95:5). The product (23 mg) is dissolved in absolute methanol and, after addition of 0.3 ml of triethylamine, stirred under reflux for 36 h. Cooling is followed by concentration, and the resulting product is thoroughly dried under high vacuum.

Yield: 19 mg (9.1% of theory) MS (DCI/NH$_3$): m/z=486 (M+NH$_4$)$^+$, 469 (M+H)$^+$ HPLC: R$_t$=6.51 min.

Example 7

5-(4-Ethyl-1-piperazinyl)-4-[(4'-hydroxy-1,1'-biphenyl-4-yl)oxy]-2-(4-methylphenyl)-3(2H)-pyridazinone hydrochloride

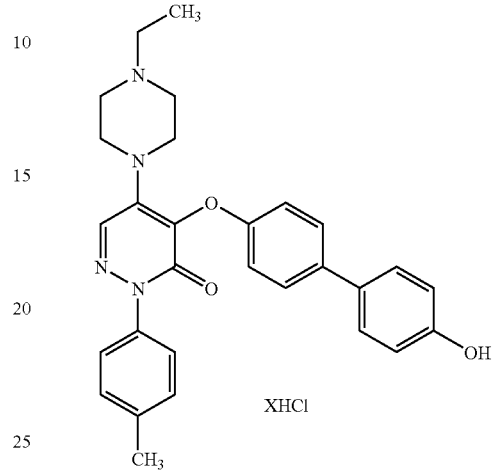

Hydrochloric acid (0.1 ml of a 1 molar solution in 1,4-dioxane) is added to a mixture of 48.3 mg (0.1 mmol) of the compound from Example 5 in 4.0 ml of 1,4-dioxane. After 30 minutes, the white suspension is concentrated and thoroughly dried under high vacuum.

Yield: 51 mg (98.3% of theory) MS (DCI/NH$_3$): m/z=500 (M+NH$_4$)$^+$, 483 (M+H)$^+$ HPLC: R$_t$=6.44 min.

Example 8

4-{[3'-(Aminomethyl)-4'-fluoro-1,1'-biphenyl-4-yl]oxy}-2-(4-chlorophenyl)-5-[4-(methylsulfonyl)-1-piperazinyl]-3(2H)-pyridazinone

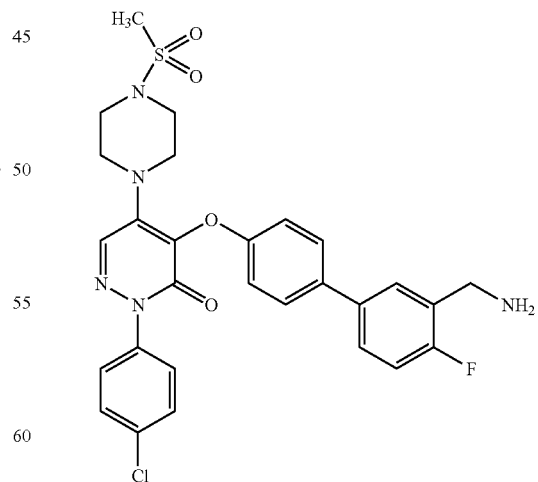

The compound from Example 50A is reacted with 2-fluoro-5-bromo-(N-tert-butyloxycarbonyl)benzylamine by general method 9-c. The coupled product is derivatized by general method 4 to give the corresponding sulfonamide.

The target product is obtained after elimination of the Boc protective group (general method 7).

MS (ESIpos): m/z=584 (M+H)⁺ HPLC: $R_t$=6.88 min.

Example 9

2-(4-Chlorophenyl)-4-{[4'-fluoro-3'-(hydroxymethyl)-1,1'-biphenyl-4-yl]oxy}-5-[4-(methylsulfonyl)-1-piperazinyl]-3(2H)-pyridazinone

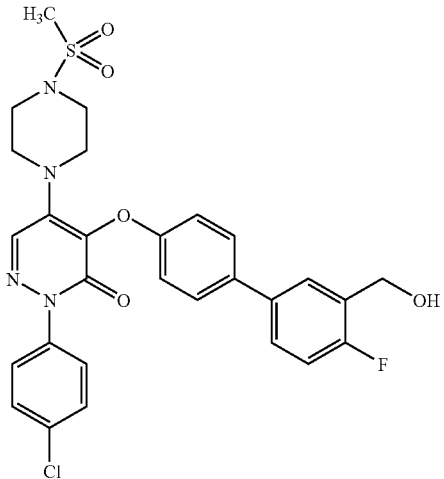

The compound from Example 50A is reacted with 2-fluoro-5-bromo-(O-tert-butyldimethylsilyl)benzyl alcohol by general method 9-c. The coupled product is derivatized by general method 4 to give the corresponding sulfonamide. The resulting intermediate is treated in acetonitrile at 0° C. with HF solution (5% of a 48% strength solution) and vigorously stirred at room temperature for 2 h. The reaction mixture is neutralized with saturated sodium bicarbonate solution and extracted with dichloromethane. The organic phase is dried over magnesium sulfate and concentrated. The product is thoroughly dried under high vacuum.

LC-MS (ESIpos): m/z=585/587 (M+H)⁺ HPLC: $R_t$=8.63 min.

Example 10

2-(4-Chlorophenyl)-5-(1H-imidazol-1-yl)-4-[4-(4-pyridinyl)phenoxy]-3(2H)-pyridazinone

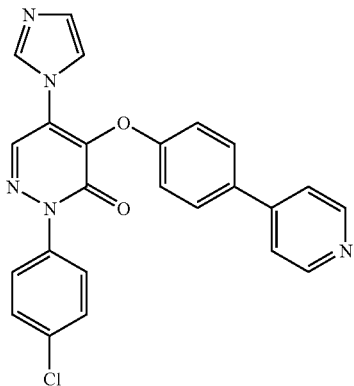

1.5 mmol of 4-(4-bromophenyl)oxy-2-(4-chlorophenyl)-5-(1H-imidazol-1-yl)-3(2H)-pyridazinone, 2.1 mmol of 4-trimethylstannylpyridine, 0.1 mmol of bis(triphenyl-phosphine)palladium dichloride and 1.3 mmol of ethyldiisopropylamine in 5 ml of dimethylformamide are heated at 100° C. for 5 hours. The solvent is removed in a rotary evaporator, and the residue is purified by chromatography on silica gel (elution with ethyl, acetate/methanol mixtures). 0.3 g (45% of theory) is obtained of m.p. 188° C.

Example 11 tert-Butyl 4-[5-(1,1'-biphenyl-4-yloxy)-1-(4-chlorophenyl)-6-oxo-1,6-dihydro-4-pyridazinyl]-1-piperazine carboxylate

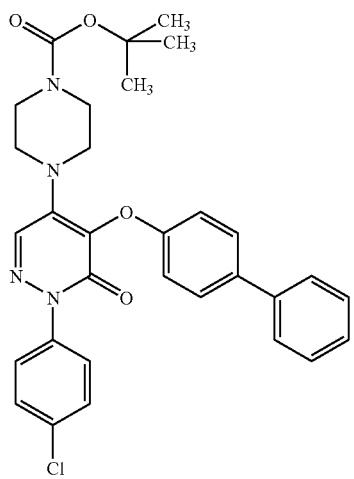

Obtainable by general method 6-d from 9.60 g (22.6 mmol) of the compound from Example 23A and 14.1 g (67.68 mmol) of potassium 4-phenylphenolate.

Yield: 7.37 g (37.6% of theory) MS (DCI/NH₃): m/z=559 (M+H)⁺ HPLC: $R_t$=11.11 min.

Example 12

4-(1,1'-Biphenyl-4-yloxy)-2-(4-chlorophenyl)-5-(1-piperazinyl)-3(2H)-pyridazinone

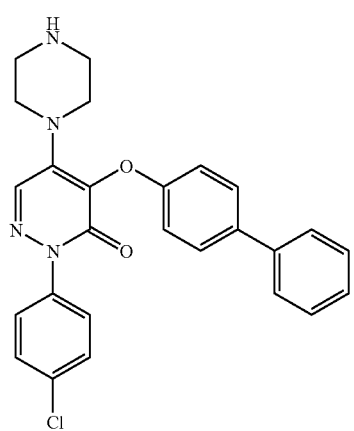

Obtainable by general method 7 from 4.23 g (7.56 mmol) of the compound from Example 11.

Yield: 3.44 g (99.2% of theory) MS (DCI/NH$_3$): m/z=459 (M+H)$^+$ HPLC: R$_t$=7.19 min.

Example 13

4-(Biphenyl-4-yloxy)-2-(4-chlorophenyl)-5-(1,4-dioxa-8-aza-spiro[4.5]dec-8-yl)-2H-pyridazin-3-one

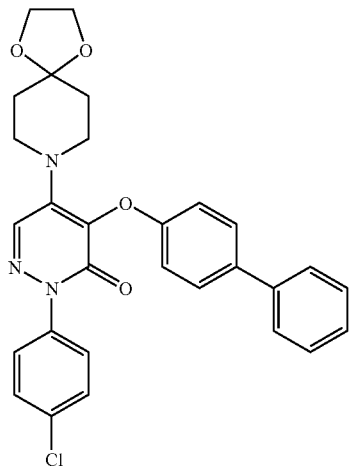

Obtainable method by 6-d from 6.0 g (15.7 mmol) of the compound from Example 22A.

Yield: 1.42 g (17.5% of theory) MS (ESI): m/z=516 (M+H)$^+$ HPLC: R$_t$=10.45 min.

Example 14

4-(Biphenyl-4-yloxy)-2-(4-chlorophenyl)-5-(4-oxo-piperidin-1-yl)-2H-pyridazin-3-one

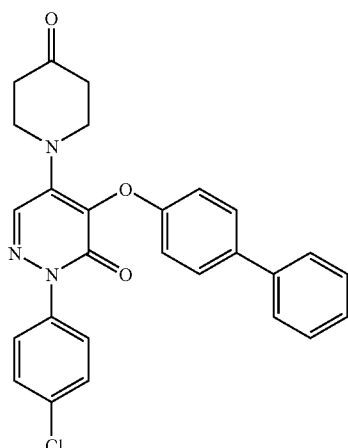

1.4 g (2.71 mmol) of the compound from Example 13 are stirred in 170 ml of acetone and 85 ml of 6 N hydrochloric acid under reflux for 2 h. After cooling, the solvent is distilled off, ethyl acetate is added, the solution is washed with saturated sodium carbonate solution and water. The organic phase is dried and concentrated. The residue is stirred with ether and filtered off with suction.

Yield: 705 mg (55.1% of theory) MS (EI): m/z=472 (M+H)$^+$ HPLC: R$_t$=9.69 min.

Example 15

4-(Biphenyl-4-yloxy)-2-(4-chlorophenyl)-5-(4-hydroxypiperidin-1-yl)-2H-pyridazin-3-one

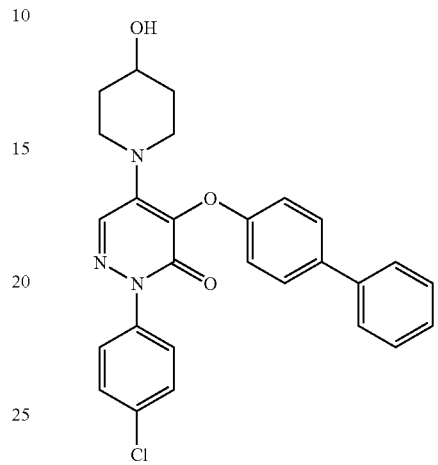

0.2 g (0.424 mmol) of the compound from Example 14 are dissolved in 7 ml of methanol and, at room temperature, 50 mg (1.3 mmol) of sodium borohydride are added in portions. Stirring for 2 h is followed by dilution with dichloromethane, washing with saturated ammonium chloride solution, drying over sodium sulfate and concentration. The crude product is stirred with 25 ml of boiling methanol and then cooled and filtered off with suction.

Yield: 78 mg (39% of theory) MS (ESI): m/z=474 (M+H)$^+$ HPLC: R$_t$=9.27 min.

A 2nd fraction is obtained by concentrating the mother liquor and stirring with dichloromethane:

Yield: 56 mg (27.9% of theory)

Example 16

4-(Biphenyl-4-yloxy)-2-(4-chlorophenyl)-5-(4-fluoropiperidin-1-yl)-2H-pyridazin-3-one

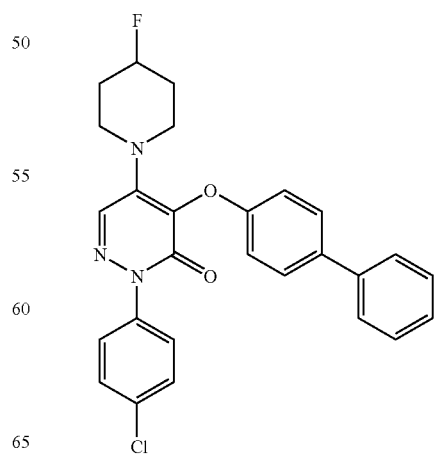

0.122 g (0.757 mmol) of diethylaminosulfur trifluoride are added to a solution of 15 mg (0.03 mmol) of the compound from Example 15 in 3 ml of dichloromethane under argon and were cooled in ice. After 4 h, the reaction solution is poured into ammonium chloride solution and extracted three times with dichloromethane. The organic phase is dried, concentrated and purified by chromatography on silica gel (mobile phase gradient from toluene to toluene/acetonitrile 18:1).

Yield: 5.6 mg (37.2% of theory) MS (ESI): m/z=476 (M+H)$^+$ DC: R$_f$=0.37 (toluene/acetonitrile 9:1)

Example 17

4-(Biphenyl-4-yloxy)-2-(4-chlorophenyl)-5-(4,4-difluoropiperidin-1-yl)-2H-pyridazin-3-one

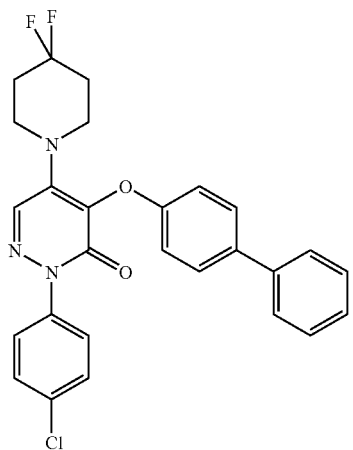

170 mg (1.06 mmol) of diethylamine-sulfur trifluoride are added dropwise to a solution of 60 mg (0.127 mmol) of the compound from Example 14 in 5 ml of dichloromethane at 0° C. under argon, and the mixture is stirred at 0° C. for 30 min. Stirring is then continued without cooling bath for 1.5 h, and the mixture is diluted with dichloromethane and ammonium chloride solution is added. The organic phase is separated off, dried over sodium sulfate and concentrated. The product is obtained by chromatography on silica gel (mobile phase: 180 ml of toluene/5 ml of acetonitrile to 180 ml of toluene/15 ml of acetonitrile).

Yield: 31 mg (49.4% of theory) MS (DCI/NH$_3$): m/z=494 (M+H)$^+$ DC: R$_f$=0.49 (toluene/acetonitrile 8:2)

Example 18

2-(4-Chlorophenyl)-4-(4'-fluorobiphenyl-4-yloxy)-5-(4-chloropiperidin-1-yl)-2H-pyridazin-3-one

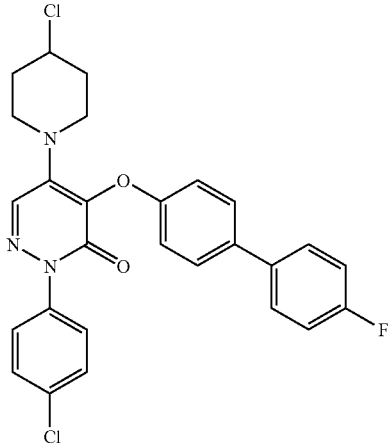

A suspension of 150 mg (0.305 mmol) of 2-(4-chlorophenyl)-4-(4'-fluorobiphenyl-4-yloxy)-5-(4-hydroxypiperidin-1-yl)-2H-pyridazin-3-one (obtainable in analogy to Example 15) is heated under reflux with 4 ml of thionyl chloride for 60 min. After cooling, the reaction solution is concentrated under high vacuum, the residue is partitioned between 50 ml of ethyl acetate and 20 ml of saturated sodium bicarbonate solution, the organic phase is separated off, and the aqueous phase is extracted three times with ethyl acetate. The combined organic phases are dried over sodium sulfate, and the solvent is removed in vacuo. The product is purified by chromatography on silica gel with toluene/ethyl acetate from 9:1 to 8:2 as mobile phase.

Yield: 30.9 mg (18.2% of theory) MS (ESI): m/z=512 (M+H)$^+$ HPLC: R$_t$=11.02 min.

Example 19

Tert-butyl (2-{4-[5-(biphenyl-4-yloxy)-1-(4-chlorophenyl)-6-oxo-1,6-dihydropyridazin-4-yl]piperazin-1-yl}-1-methyl-2-oxo-ethyl)carboxylate

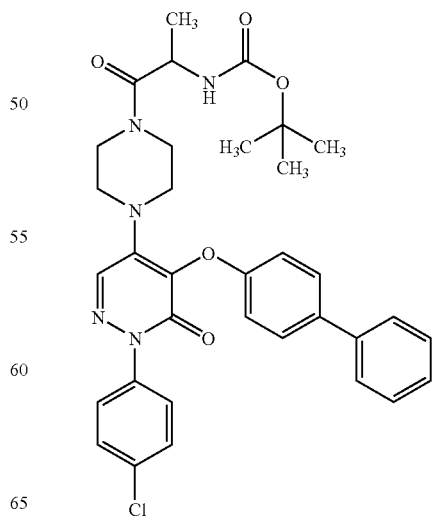

160 mg (0.348 mmol) of the compound from Example 12, dissolved in 1 ml of dichloromethane, are added dropwise to a solution of 92 mg (0.487 mmol) of Boc-L-alanine, 93.4 mg (0.487 mmol) of EDC, 65.8 mg (0.487 mmol) of HOBt and 0.1 ml (0.717 mmol) of triethylamine in 2 ml of tetrahydrofuran and 10 ml of dichloromethane while stirring under argon at 0° C. The mixture is stirred at room temperature overnight. The reaction solution is diluted with 100 ml of dichloromethane, washed with saturated sodium bicarbonate solution and brine, dried over sodium sulfate and concentrated. The residue is stirred with ether and filtered off with suction.

Yield: 195.5 mg (89.0% of theory) MS (ESI): m/z=630 (M+H)$^+$ HPLC: R$_t$=10.15 min.

Example 20

4-(Biphenyl-4-yloxy)-2-(chlorophenyl)-5-(4-L-alanylpiperazin-1-yl)-2H-pyridazin-3-one

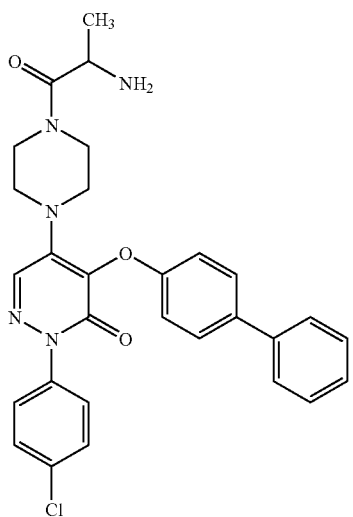

Obtainable from 180 mg (0.286 mmol) of the compound from Example 19 by general method 7.

Yield: 80 mg (52.9% of theory) MS (ESD: m/z=530 (M+H)$^+$ HPLC: R$_t$=7.33 min.

Example 21

4-[5-(4'-Fluorobiphenyl-4-yloxy)-6-oxo-1-(4-trifluoromethylphenyl)-1,6-dihydropyridazin-4-yl]piperazine-1-carbaldehyde

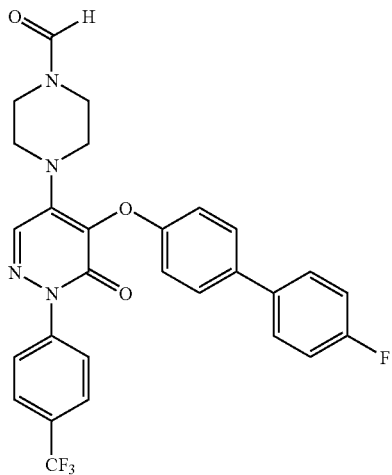

First, 613.1 mg (3.13 mmol) of EDC are added to a solution of 288.5 mg (6.27 mmol) of formic acid in 4 ml of dichloromethane, and the mixture is stirred at 0° C. for 20 minutes. Subsequently, 80 mg (0.157 mmol) of 4-(4'-fluorobiphenyl-4-oxy)-2-(4-trifluoromethylphenyl)-5-(piperazin-1-yl)-3(2H)-pyridazinone (obtainable in analogy to Example 12) and 0.1 ml (0.717 mmol) of triethylamine are added to this reaction solution at 0° C., and the mixture is stirred at 0° C. overnight. Aqueous work-up with dilute hydrochloric acid and then saturated sodium bicarbonate solution results in a crude product, which is chromatographed on silica gel with dichloromethane/methanol 10:1 as mobile phase.

Yield: 24.6 mg (7.3% of theory) MS (ESI): m/z=539 (M+H)$^+$ HPLC: R$_t$=9.40 min.

Example 22

4-(Biphenyl-4-yloxy)-2-(4-chlorophenyl)-5(4-cyclopropylpiperazin-1-yl)-2H-pyridazin-3-one

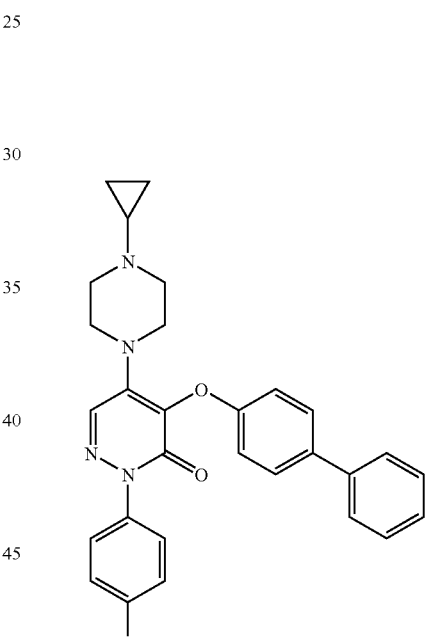

1.77 ml (22.1 mmol) of cyclopropyl bromide are added dropwise to a solution of 150 mg (0.327 mmol) of the compound from Example 40 in 5 ml of DMF and 0.34 ml (2.45 mmol) of triethylamine, and the mixture is then stirred at 120° C. overnight. The reaction mixture is poured into 150 ml of water and extracted twice with ethyl acetate. The organic phase is dried over sodium sulfate and concentrated. The product is purified by chromatography on silica gel (mobile phase: toluene/acetonitrile gradient from 40:1 to 4:1).

Yield: 41 mg(21.1% of theory) MS (DCI/NH$_3$): m/z=499 (M+H)$^+$ HPLC: R$_t$=7.71 min.

Example 23

2-(4-Chlorophenyl)-5-(3,5-dihydro-2H-pyridin-1-yl)-4-(4'-fluorobiphenyl-4-yloxy)-2H-pyridazin-3-one

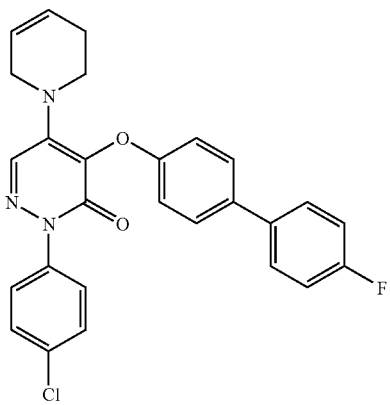

Obtainable by general method 6-c from 90 mg (1.1 mmol) of 1,2,5,6-tetrahydropyridine and 300 mg (0.702-mmol) of 5-chloro-4-(4-fluorophenylphenyloxy)-2-(4-chlorophenyl)-2(3H)-pyridazinone.

Yield: 196 mg (58.8% of theory) MS (DCI/NH$_3$): m/z=474 (M+H)$^+$ HPLC: R$_t$=10.87 min.

Example 24

2-(4-Chlorophenyl)-5-(3,4-dihydroxy-1-piperidinyl)-4-[(4'-fluoro-1,1'-biphenyl-4-yl)oxy]-3(2H)-pyridazinoe

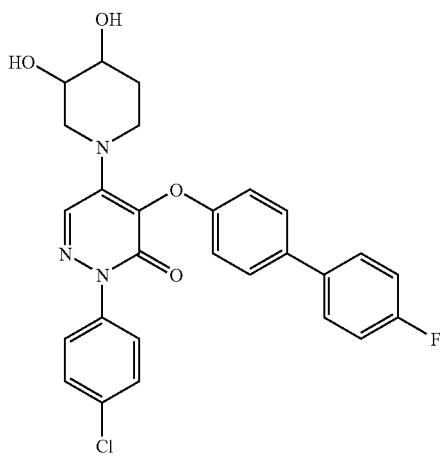

90 mg (0.753 mmol) of N-methylmorpholine N-oxide and 0.64 ml (0.949 mmol) of osmiumtetroxide as 2.5% by weight solution in tert-butanol are added to a solution of 100 mg (0.211 mmol) of the compound from Example 23 in 8 ml of THF, and the mixture is stirred in the dark at room temperature overnight. 80 mg of sodium sulfite in 0.5 ml of water are then added to the reaction mixture, which is diluted with 80 ml of dichloromethane and 20 ml of sodium chloride solution and stirred for 1 h. The organic phase is dried over sodium sulfate and concentrated, and the residue is purified by chromatography on silica gel using toluene/acetonitrile 9:1 as mobile phase. The residue is then stirred in ether, filtered off with suction and dried under high vacuum.

Yield: 23 mg (21.5% of theory) MS (ESI): m/z=508 (M+H)$^+$ HPLC: R$_t$=8.71 min.

Example 25

2-(4-Chlorophenyl)-4-[(4'-fluoro-1,1'-biphenyl-4-yl)oxy]-5-[4-(hydroxymethyl)-1-piperidinyl]-3(2H)-pyridazinone

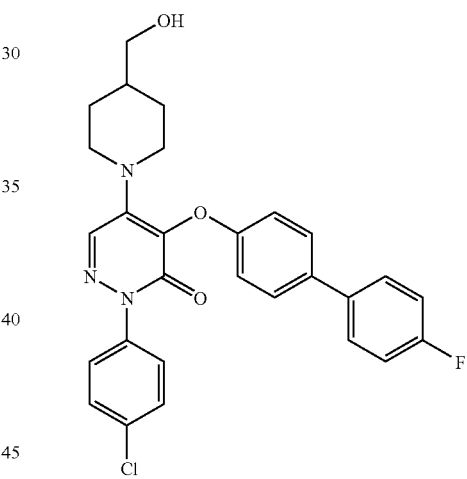

20.0 g (46.8 mmol) of 5-chloro-4-(4-fluorophenylphenyloxy)-2-(4-chlorophenyl)-2(3H)-pyridazinone, 6.47 g (56.17 mmol) of 4-hydroxymethylpiperidine, 7.77 g (46.81 mol) of potassium iodide and 16.31 ml (93.62 mmol) of ethyldiisopropylamine are stirred in 200 ml of DMF under argon at 12° C. overnight. The reaction mixture is cooled to room temperature, diluted with dichloromethane and washed three times with water. The organic phase is dried and concentrated, and the resulting residue is stirred with ether and filtered off with suction. The crude product is purified by chromatography on silica gel in a gradient process with toluene and toluene/acetonitrile (from 20:1 via 10:1 to 5:1) as mobile phase.

Yield: 13.2 g (55.7% of theory) MS (ESI): m/z=506 (M+H)$^+$ HPLC: R$_t$=9.50 min.

Example 26

4-(1,1'-Biphenyl-4-yloxy)-2-(4-chlorophenyl)-5-(1-oxido-4-thiomorpholinyl)-3(2H)-pyridazinone

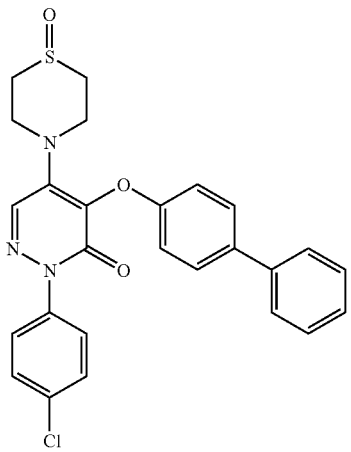

110 mg (0.308 mmol) of 3-chloroperoxybenzoic acid (57-86% pure) are added in, portions over the course of 5 min to a solution of 150 mg (0.308 mmol) of 2-(4-chlorophenyl)-4-(4-phenylphenyloxy)-5-(thiomorpholinyl-1-)-2(3H)-pyridazinone in 15 ml of dichloromethane, and the mixture is stirred at room temperature for 3 h. The reaction solution is then loaded onto about 100 ml of dry silica gel and chromatographed with ethyl acetate and ethyl acetate/acetone mixtures in the ratio 4:1, 1:1 and 1:4 as mobile phase.

Yield: 56 mg (36.6% of theory) MS (DCI/NH$_3$): m/z=492 (M+H)$^+$ HPLC: R$_t$=8.68 min.

Example 27

4-(1,1'-Biphenyl-4-yloxy)-2-(4-chlorophenyl)-5-(1,1-dioxido-4-thiomorpholinyl)-3(2H)-pyridazinone

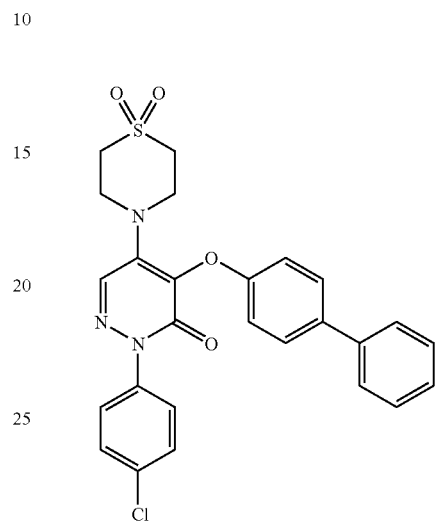

This compound was obtained as further product in the preparation of Example 26 and crystallized by trituration with diisopropyl ether.

Yield: 95 mg (52.7% of theory) MS (ESI): m/z=508 (M+H)$^+$ HPLC: R$_t$=9.38 min.

Exemplary embodiments 28-223 listed in table 7 were prepared by general processes 1-17:

| Example No. | Structure | Analysis (data in ° C. relate to the melting point) | General process |
|---|---|---|---|
| 28 | 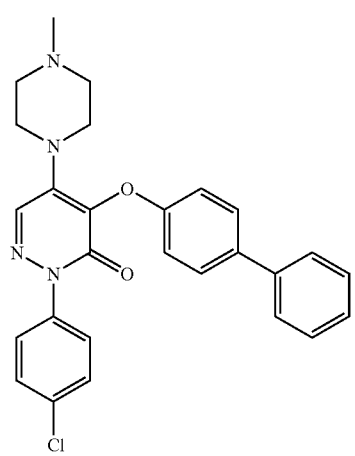 | DCI/NH$_3$: 490 (M + NH$_4$, 100%)<br>HPLC: rt (%) = 7.38 (99.4) | 6a |

| Example No. | Structure | Analysis (data in ° C. relate to the melting point) | General process |
|---|---|---|---|
| 29 | 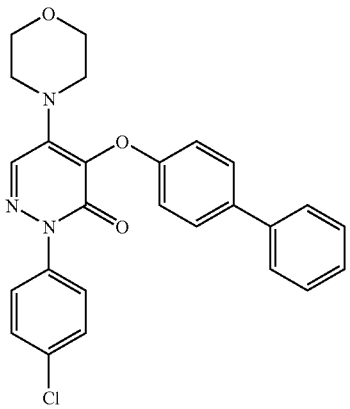 | DCI/NH$_3$: 460 (M + H, 100%)<br>HPLC: rt (%) = 7.88 (98.3) | 6a |
| 30 | 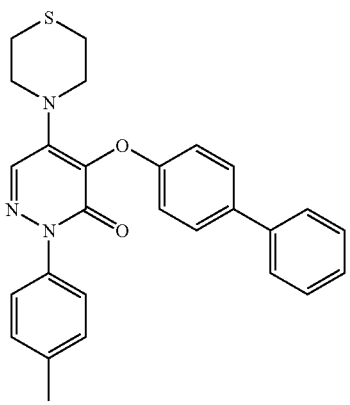 | DCI/NH$_3$: 456 (M + H, 100%)<br>HPLC: rt (%) = 8.34 (78.7) | 6a |
| 31 | 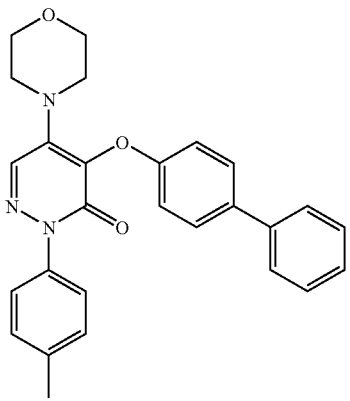 | DCI/NH$_3$: 440 (M + H, 100%)<br>HPLC: rt (%) = 7.64 (98.1) | 6a |

-continued

| Example No. | Structure | Analysis (data in ° C. relate to the melting point) | General process |
|---|---|---|---|
| 32 | 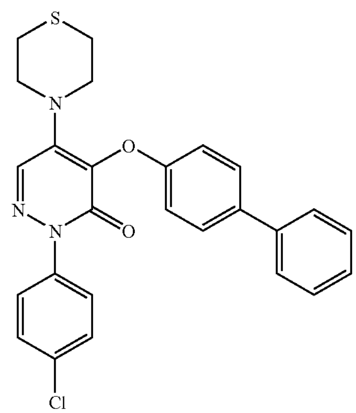 | DCI/NH₃: 476 (M + H, 100%)<br>HPLC: rt (%) = 8.50 (97.9) | 6a |
| 33 | 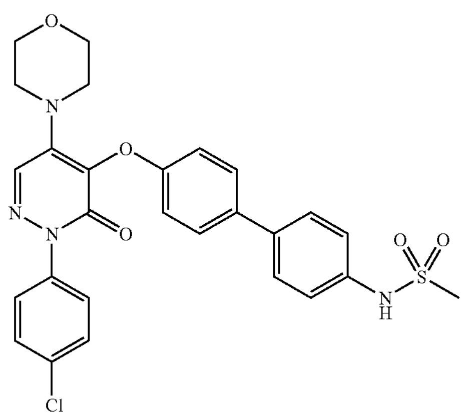 | DCI/NH₃: 553 (M + H, 100%)<br>HPLC: rt (%) = 6.72 (94.0) | 6a |
| 34 | 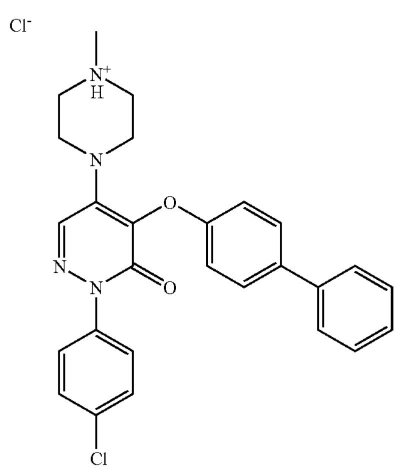 | m.p.: 162° C.<br>ESI: 473 (M + H, 100)<br>HPLC: rt (%) 7.42 (99.6)<br>¹H-NMR (300 MHz, DMSO-d₆):<br>δ = 2.7 (s, 3H), 3.0–4.2 (several broad m, 8H), 7.1 (m, 2H),<br>7.3–7.7 (m, 11H), 8.3 (s, 1H) | 6a |

-continued

| Example No. | Structure | Analysis (data in ° C. relate to the melting point) | General process |
|---|---|---|---|
| 35 | 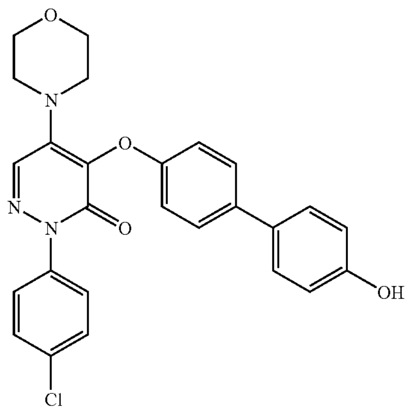 | DCI/NH₃: 476 (M + H, 100%)<br>HPLC: rt (%) = 6.72 (96.7) | 6a |
| 36 | 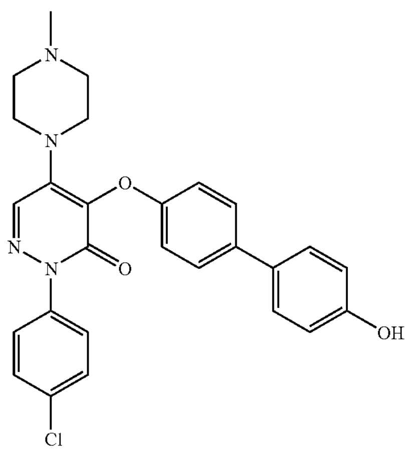 | DCI/NH₃: 489 (M + H, 100%)<br>HPLC: rt (%) = 5.40 (93.3) | 6a |
| 37 | 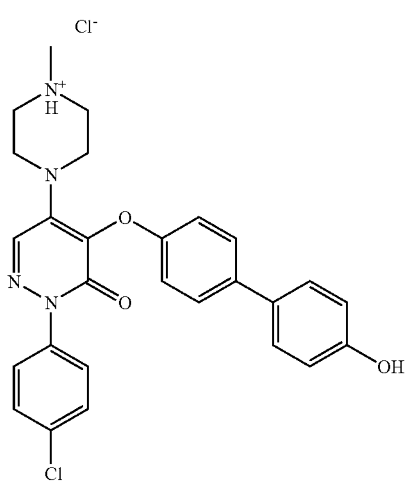 | DCI/NH₃: 489 (M + H, 100%)<br>HPLC: rt (%) = 6.74 (100) | 6a |

-continued

| Example No. | Structure | Analysis (data in ° C. relate to the melting point) | General process |
|---|---|---|---|
| 38 | 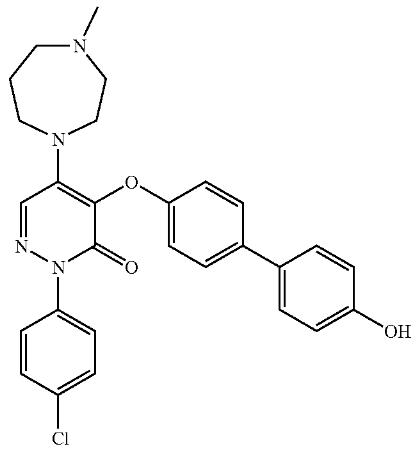 | DCI/NH$_3$: 503 (M + H, 100%)<br>HPLC: rt (%) = 6.80 (94.1) | 6a |
| 39 | 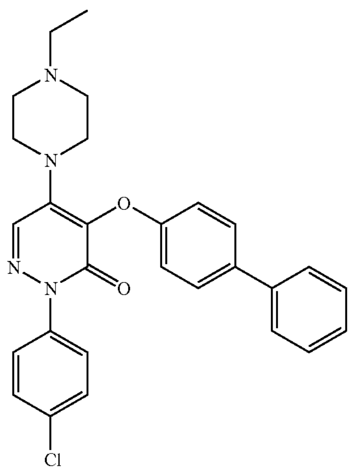 | DCI/NH$_3$: 487 (M + H, 100%)<br>HPLC: rt (%) = 7.44 (94.7) | 6a |
| 40 | 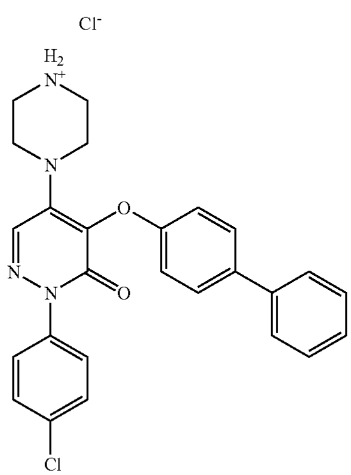 | MS (ESI): 459 (M + H)<br>(free base)<br>HPLC: rt (%) = 7.22 (99.9) | 7 |

-continued

| Example No. | Structure | Analysis (data in ° C. relate to the melting point) | General process |
|---|---|---|---|
| 41 | 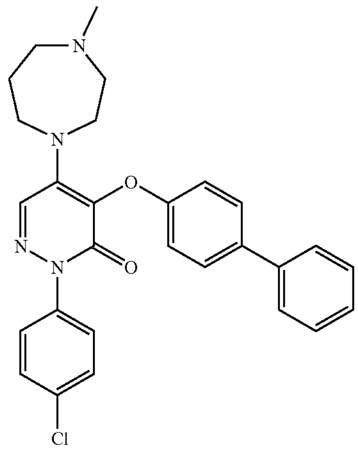 | ESI: 487 (M + H, 100%)<br>HPLC: rt (%) = 7.47 (100) | 6a |
| 42 | 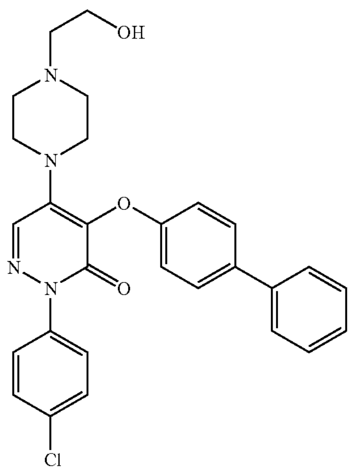 | ESI: 503 (M + H, 100%)<br>HPLC: rt (%) = 7.20 (91.2) | 6a |
| 43 | 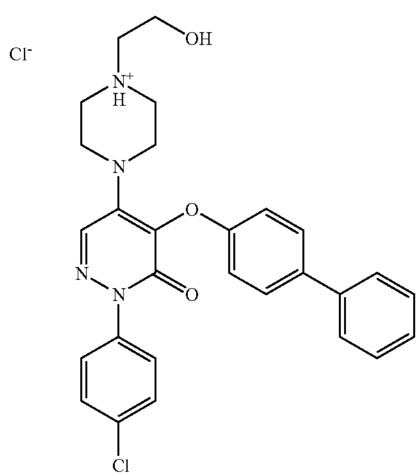 | ESI (CH₃CN/H₂O; 0.1% CH₃COOH): 503 (100%)<br>HPLC: rt (%) = 6.07 (99.6) | 6a |

-continued
| Example No. | Structure | Analysis (data in ° C. relate to the melting point) | General process |
|---|---|---|---|
| 44 | 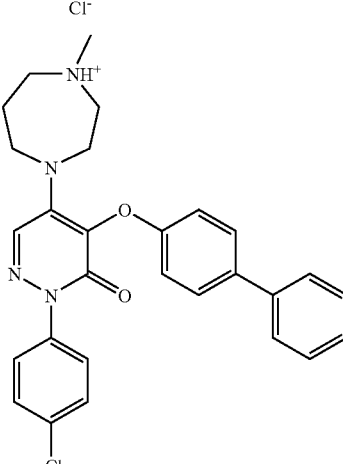 | ESI (CH$_3$CN/H$_2$O; 0.1% CH$_3$COOH): 487 (100%) HPLC: rt (%) = 7.42 (95.3) | 6a |
| 45 | 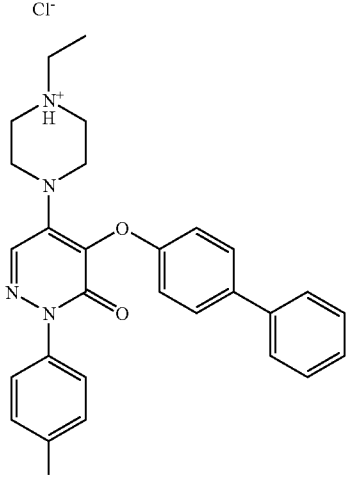 | ESI (CH$_3$CN/H$_2$O; 0.1% CH$_3$COOH): 487 (100%) HPLC: rt (%) = 6.27 (99.0) | 6a |
| 46 | 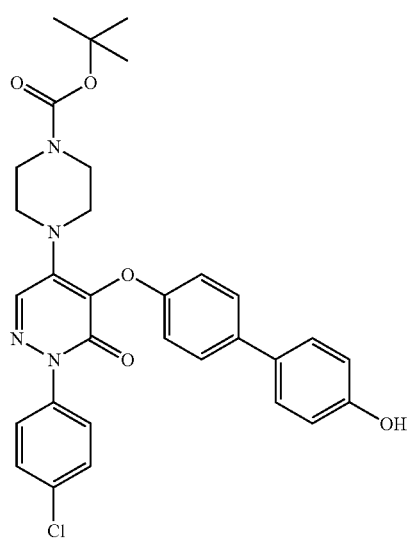 | DCI/NH$_3$: 592 (M + NH$_4$, 100%) HPLC: rt (%) = 9.86 (50.8) | 6a |

-continued

| Example No. | Structure | Analysis (data in ° C. relate to the melting point) | General process |
|---|---|---|---|
| 47 | 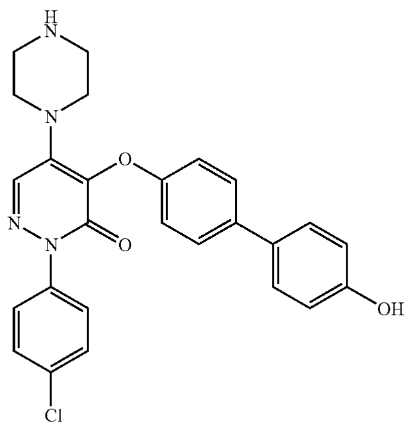 | DCI/NH₃: 492 (M + NH₄, 100%), 475 (M + H, 51%) HPLC: rt (%) = 6.58 (88.8) | 7 |
| 48 | 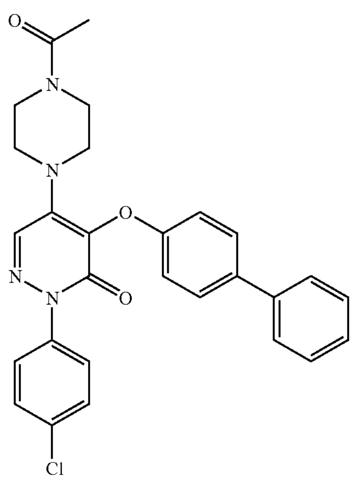 | ESI (CH₃CN/H₂O; 0.1% CH₃COOH): 501 (M + H, 100%) HPLC: rt (%) = 9.15 (91.6) | 2 |
| 49 | 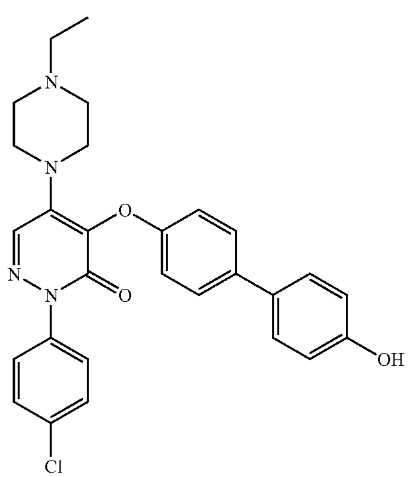 | DCI/NH₃: 503 (M + H, 100%) HPLC: rt (%) = 6.74 (99.6) | 6a |

-continued
| Example No. | Structure | Analysis (data in ° C. relate to the melting point) | General process |
|---|---|---|---|
| 50 | 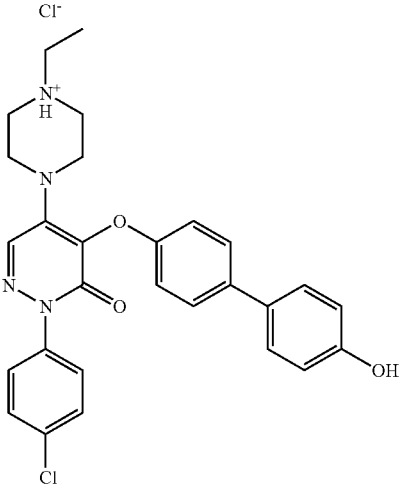 | DCI/NH$_3$: 502 (M + NH$_4$, 100%), 503 (M + H, 67%)<br>HPLC: rt (%) = 6.69 (100) | 6a |
| 51 | 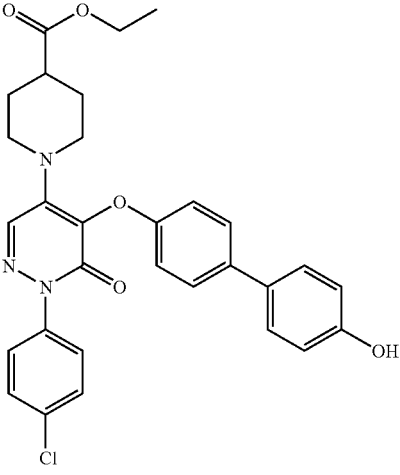 | DCI/NH$_3$: 563 (M + NH$_4$, 100%)<br>HPLC: rt (%) = 9.69 (96.9) | 6a |
| 52 | 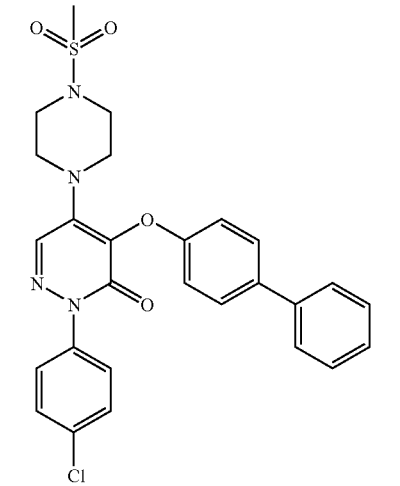 | ESI (CH$_3$CN/H$_2$O; ammonium acetate): 537 (100%)<br>HPLC: rt (%) = 9.75 (98.0) | 4 |

-continued

| Example No. | Structure | Analysis (data in ° C. relate to the melting point) | General process |
|---|---|---|---|
| 53 | *(structure)* | ESI: 547 (M + H, 100%)<br>HPLC: rt (%) = 9.08 (100) | 6a |
| 54 | *(structure)* | ESI: 517 (100%)<br>HPLC: rt (%) = 7.58 (97.0) | 6a |
| 55 | *(structure)* | DCI/NH$_3$: 473 (M + H, 100%)<br>HPLC: rt (%) = 7.40 (92.4) | 7 |

-continued
| Example No. | Structure | Analysis (data in ° C. relate to the melting point) | General process |
|---|---|---|---|
| 56 | 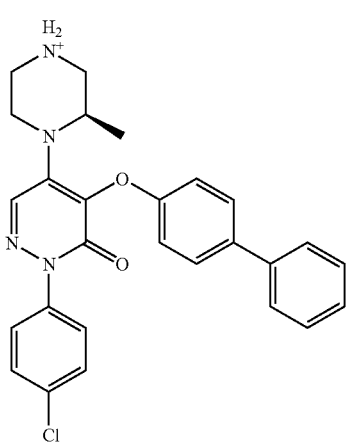 | DCI/NH$_3$: 473 (M + H) | 7 |
| 57 | 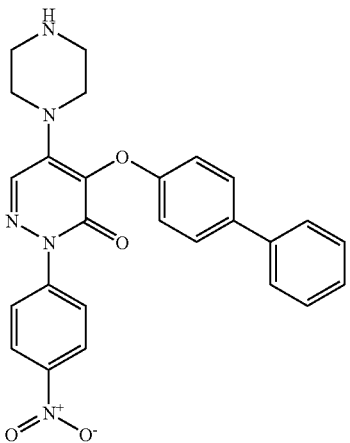 | DCI/NH$_3$: 470 (M + H, 100%)<br>HPLC: rt (%) = 7.27 (100) | 7 |
| 58 | 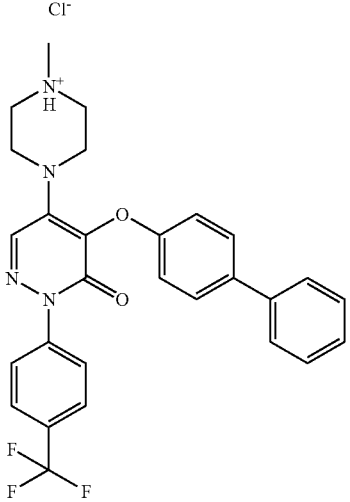 | HPLC: rt (%) = 7.65 (98.4) | 6a |

-continued

| Example No. | Structure | Analysis (data in ° C. relate to the melting point) | General process |
|---|---|---|---|
| 59 | 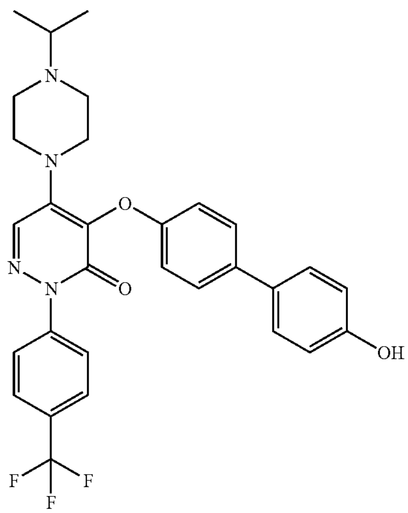 | ESI: 551 (M + H, 100%)<br>HPLC: rt (%) = 6.96 (98.9) | 6a |
| 60 | 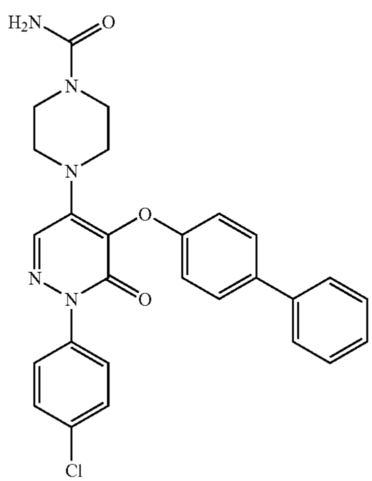 | ESI: 502 (M + H, 100%)<br>HPLC: rt (%) = 8.51 (97.5) | 5 |
| 61 | 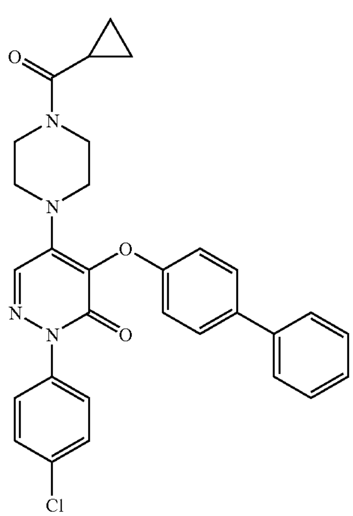 | ESI: 527 (M + H, 100%)<br>HPLC: rt (%) = 9.65 (95.9) | 2 |

-continued

| Example No. | Structure | Analysis (data in ° C. relate to the melting point) | General process |
|---|---|---|---|
| 62 | 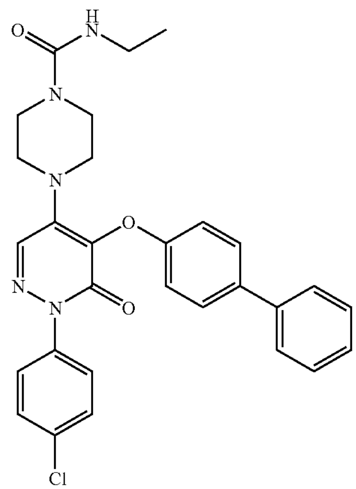 | ESI: 530 (M + H, 100%)<br>HPLC: rt (%) = 9.22 (96.6) | 6a |
| 63 | 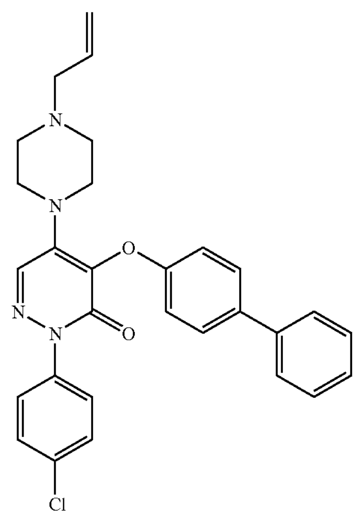 | ESI: 499 (M + H, 100%)<br>HPLC: rt (%) = 7.66 (94.7) | 6a |
| 64 | 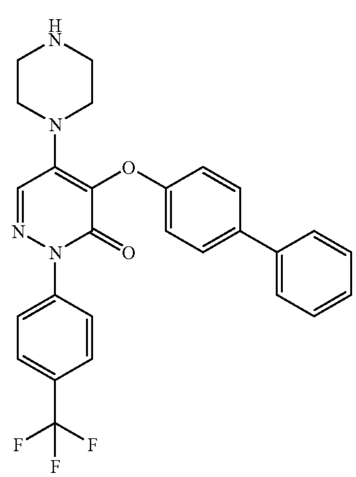 | ESI: 493 (M + H 100%)<br>HPLC: rt (%) = 7.64 (100) | 7 |

-continued

| Example No. | Structure | Analysis (data in ° C. relate to the melting point) | General process |
|---|---|---|---|
| 65 | 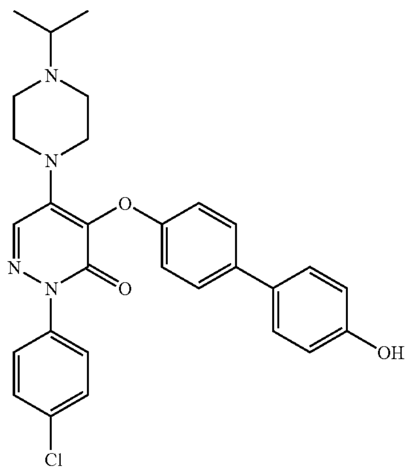 | ESI: 517 (M + H, 100%)<br>$R_f$: 0.30 (toluene/acetonitrile 4:1) | 6a |
| 66 | 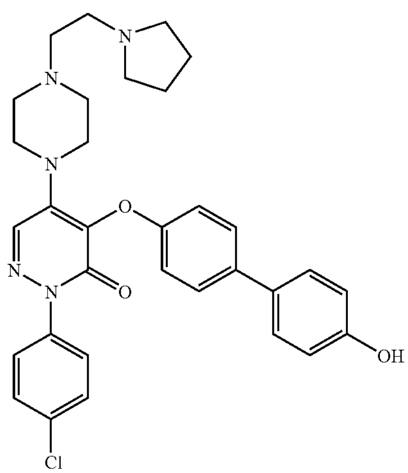 | DCI/NH$_3$: 572 (M + H, 100%)<br>HPLC: rt (%) = 6.69 (100) | 6a |
| 67 | 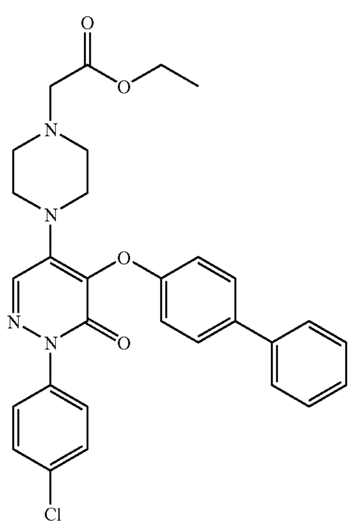 | DCI/NH$_3$: 545 (M + H, 100%)<br>HPLC: rt (%) = 8.24 (99.3) | 6a |

-continued

| Example No. | Structure | Analysis (data in ° C. relate to the melting point) | General process |
|---|---|---|---|
| 68 | 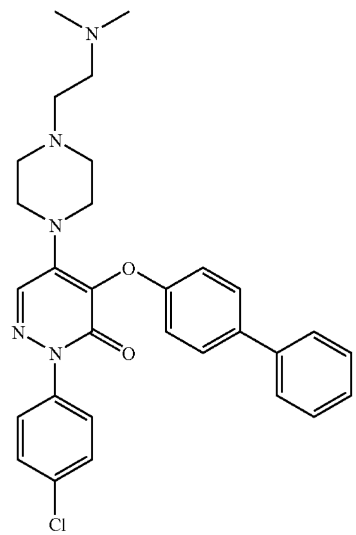 | DCI/NH₃: 530 (M + H, 100%)<br>HPLC: rt (%) = 7.28 (73.6) | 6a |
| 69 | 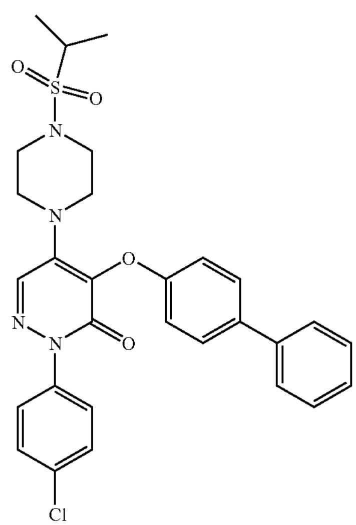 | DCI/NH₃: 565 (M + H, 100%)<br>HPLC: rt (%) = 10.12 (76.6) | 4 |
| 70 | 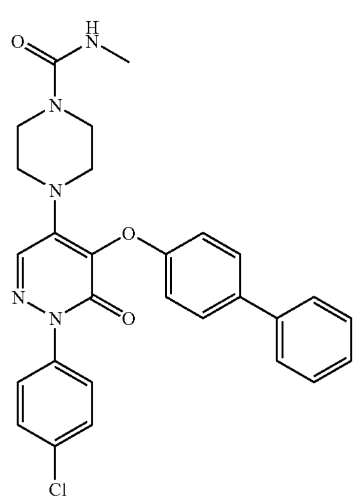 | ESI: 516 (M + H, 60%)<br>HPLC: rt (%) = 8.90 (99.7) | 6a |

-continued

| Example No. | Structure | Analysis (data in ° C. relate to the melting point) | General process |
|---|---|---|---|
| 71 | 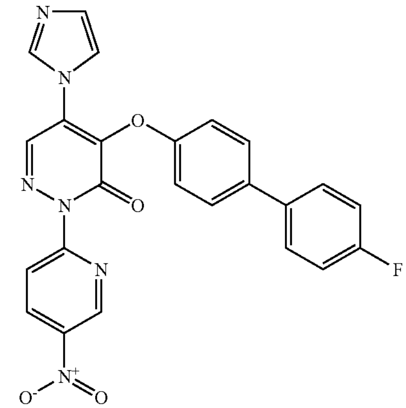 | 186° C. | 16a |
| 72 | 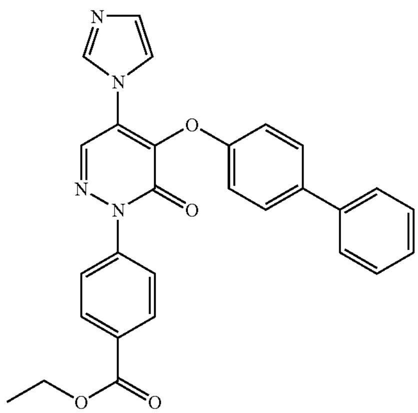 | 151° C. | 16a |
| 73 | 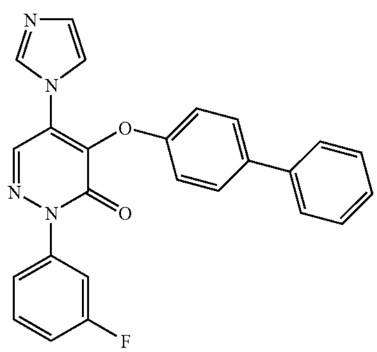 | 148° C. | 16a |
| 74 | 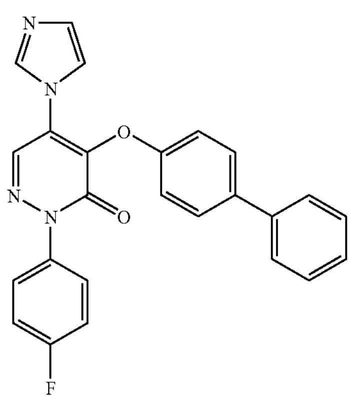 | 119° C. | 16a |

-continued
| Example No. | Structure | Analysis (data in ° C. relate to the melting point) | General process |
|---|---|---|---|
| 75 | 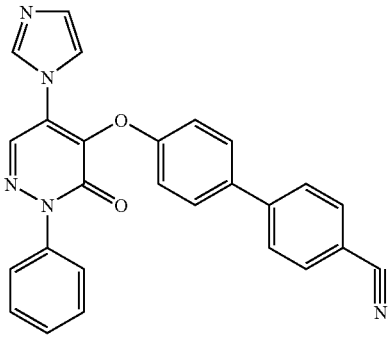 | | 16a |
| 76 | 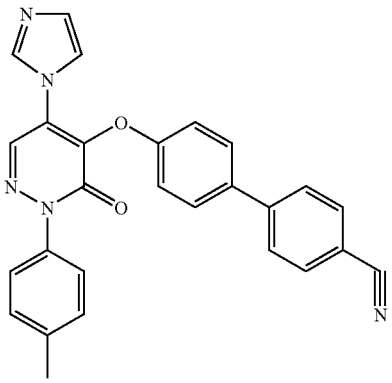 | 220° C. | 16a |
| 77 | 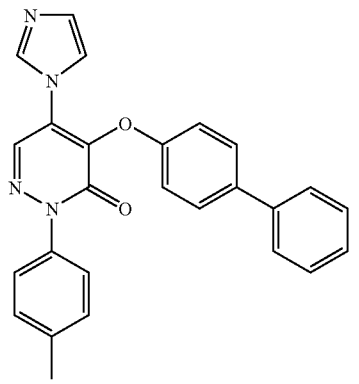 | 177° C. | 16a |
| 78 | 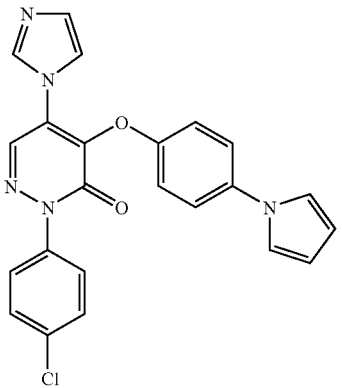 | 188° C. | 16a |

| Example No. | Structure | Analysis (data in ° C. relate to the melting point) | General process |
|---|---|---|---|
| 79 | 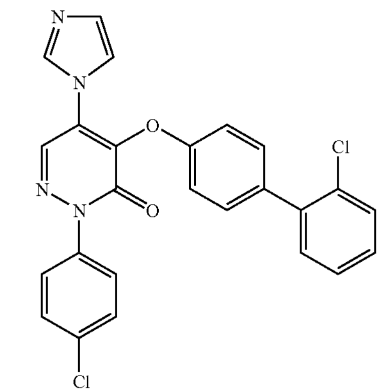 | | |
| 80 | 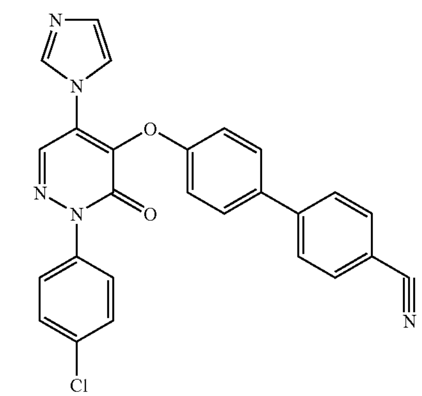 | 276° C. | 16a |
| 81 | 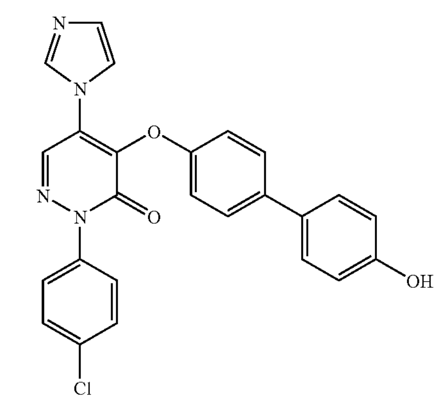 | 216° C.<br>¹H-NMR (200 MHz, DMSO-d₆):<br>δ= 6.7 (m, 2H), 7.2–7.3 (m, 3H),<br>7.4–7.8 (m, 9H), 8.25 (s, 1H), 8.70 (s, 1H), 9.5 (s, 1H) | 16a |
| 82 | 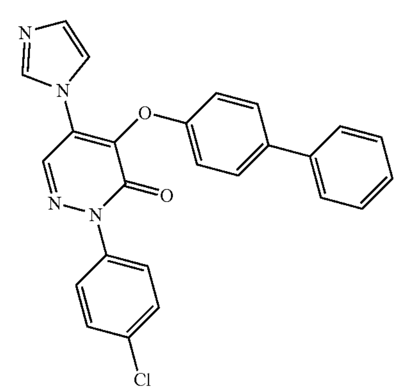 | 188° C.<br>¹H-NMR (400 MHz, CDCl₃):<br>δ= 7.15 (m, 2H, AA' of a AA'BB' system), 7.2–7.6 (several m, 11H),<br>7.65 (m, 2H, BB' of a AA'BB' system), 8.1 (s, 1H), 8.2 (s, 1H) | 16c |

-continued
| Example No. | Structure | Analysis (data in ° C. relate to the melting point) | General process |
|---|---|---|---|
| 83 | 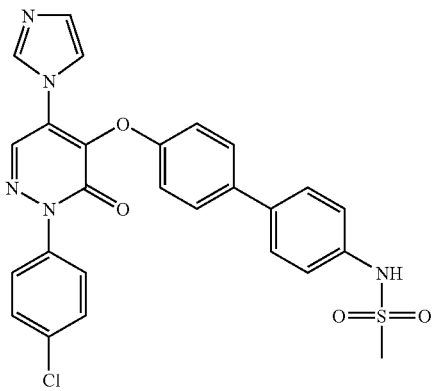 | 180° C. | 16a |
| 84 | 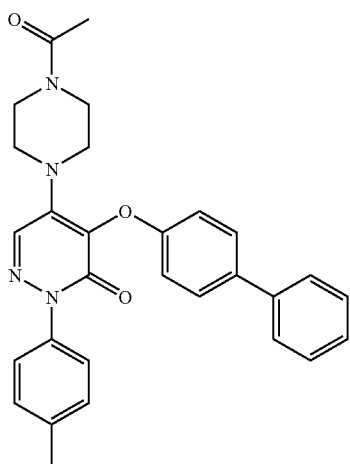 | MS (B): 481 (M + H) (100)<br>HPLC: 8.77 (99) | 2 |
| 85 | 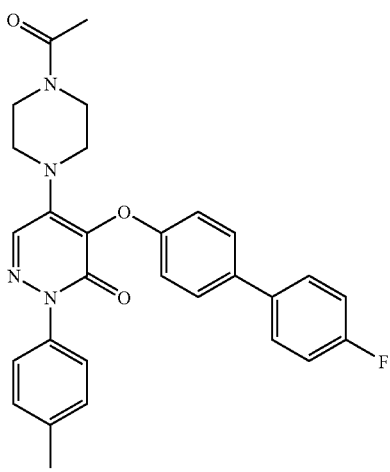 | MS (B): 499 (M + H) (100)<br>HPLC: 8.84 (100) | 2 |

-continued

| Example No. | Structure | Analysis (data in ° C. relate to the melting point) | General process |
|---|---|---|---|
| 86 | 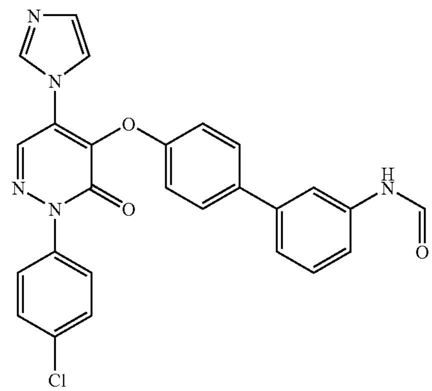 | MS (A): 484 (M + H) (100)<br>HPLC: 7.45 (98) | 3 |
| 87 | 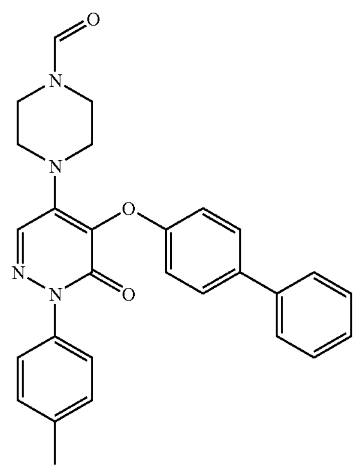 | MS (B): 467 (M + H) (100)<br>HPLC: 8.73 (99) | 3 |
| 88 | 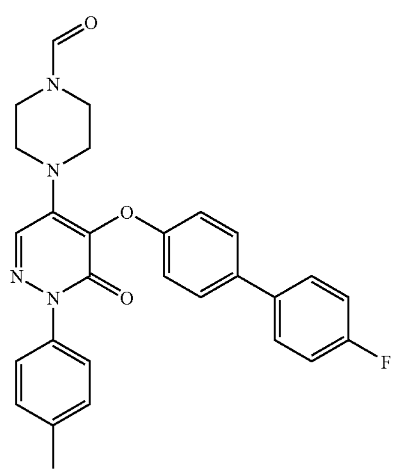 | MS (B): 485 (M + H) (100)<br>HPLC: 8.80 (86) | 3 |

-continued

| Example No. | Structure | Analysis (data in ° C. relate to the melting point) | General process |
|---|---|---|---|
| 89 | 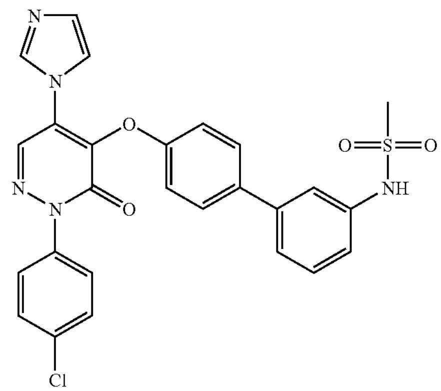 | MS (B): 534 (M + H) (100)<br>HPLC: 7.83 (100) | 4 |
| 90 | 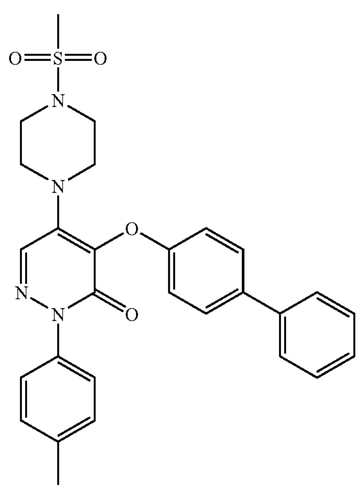 | MS (B): 517 (M + H) (100)<br>HPLC: 9.38 (97) | 4 |
| 91 | 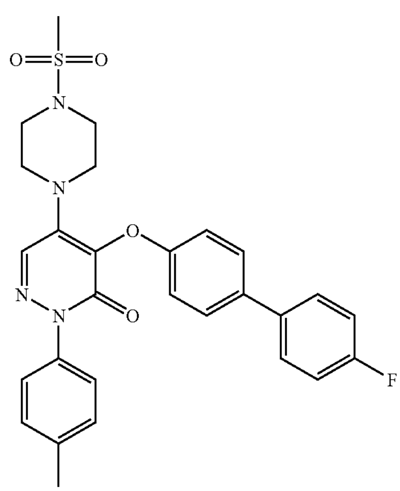 | MS (B): 535 (M + H) (100)<br>HPLC: 9.44 (94) | 4 |

-continued

| Example No. | Structure | Analysis (data in ° C. relate to the melting point) | General process |
|---|---|---|---|
| 92 | (structure) | MS (D): 615 (M + H) (100)<br>HPLC: 9.75 (86) | 4 |
| 93 | (structure) | MS (E): 612 (M + H) (100)<br>HPLC: 8.47 (92) | 4 |
| 94 | (structure) | MS (E): 608 (M + H) (100)<br>HPLC: 8.30 (92) | 4 |

-continued

| Example No. | Structure | Analysis (data in ° C. relate to the melting point) | General process |
|---|---|---|---|
| 95 | 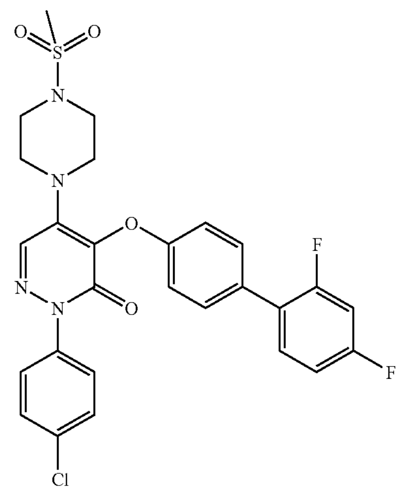 | MS (D): 573 (M + H) (100)<br>HPLC: 9.75 (98) | 4 |
| 96 | 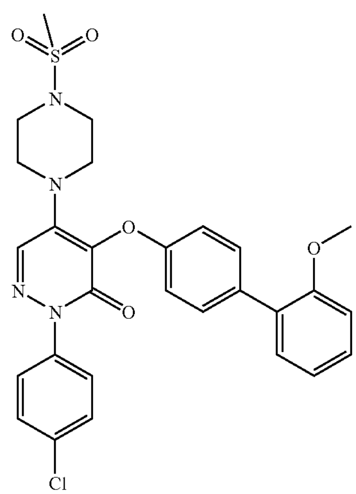 | MS (D): 567 (M + H) (100)<br>HPLC: 9.62 (96) | 4 |
| 97 | 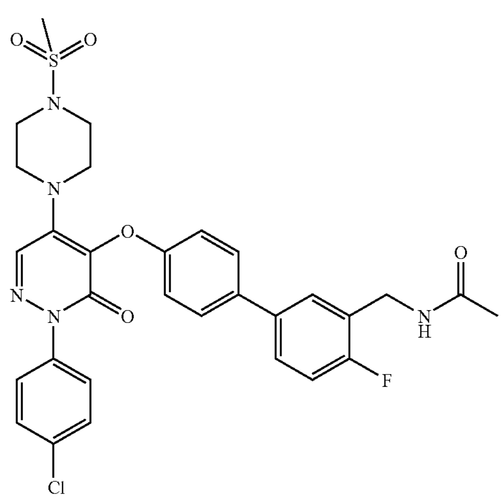 | MS (D): 626 (M + H) (100)<br>HPLC: 8.34 (100) | 4 |

-continued

| Example No. | Structure | Analysis (data in ° C. relate to the melting point) | General process |
|---|---|---|---|
| 98 | 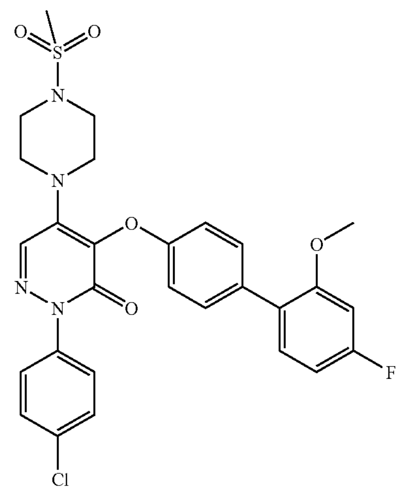 | MS (D): 585 (M + H) (100)<br>HPLC: 9.71 (95) | 4 |
| 99 | 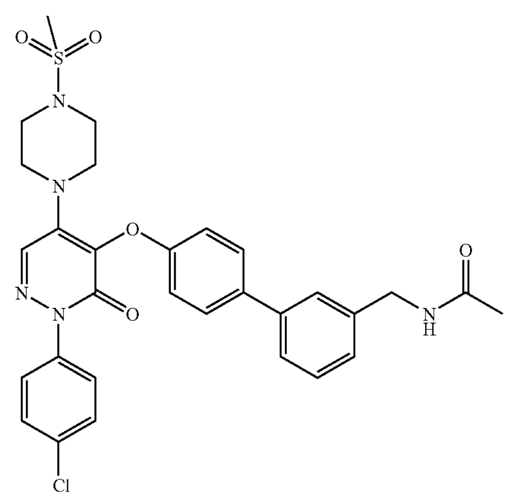 | MS (D): 608 (M + H) (100)<br>HPLC: 8.19 (100) | 4 |
| 100 | 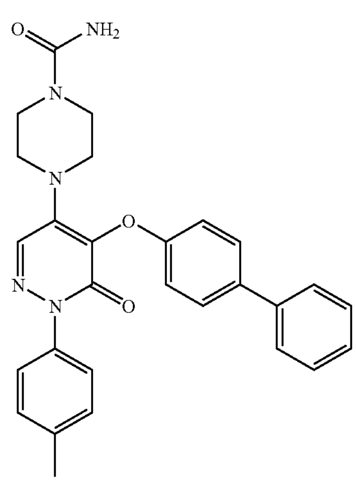 | MS (B): 482 (M + H) (100)<br>HPLC: 8.21 (98) | 5 |

-continued

| Example No. | Structure | Analysis (data in ° C. relate to the melting point) | General process |
|---|---|---|---|
| 101 | 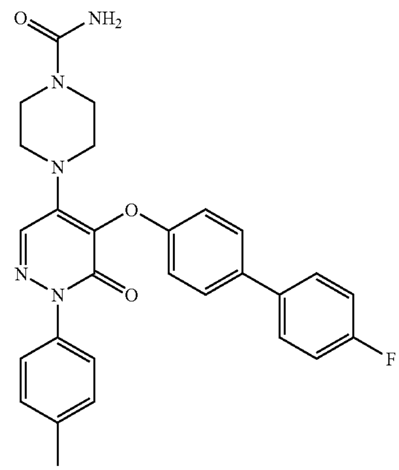 | MS (B): 500 (M + H) (100)<br>HPLC: 8.28 (89) | 5 |
| 102 | 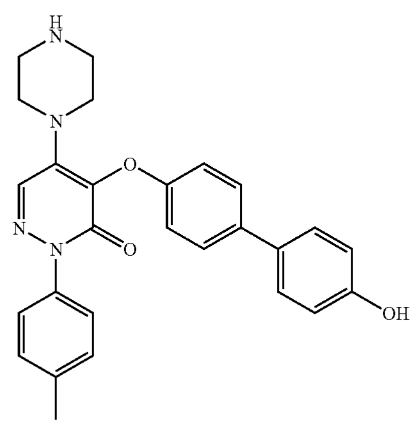 | MS (B): 455 (M + H) (100)<br>HPLC: 4.98 (96) | 7 |
| 103 | 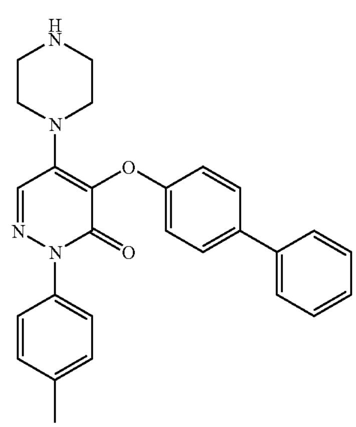 | MS (B): 439 (M + H) (100)<br>HPLC: 6.89 (95) | 7 |

-continued

| Example No. | Structure | Analysis (data in ° C. relate to the melting point) | General process |
|---|---|---|---|
| 104 | 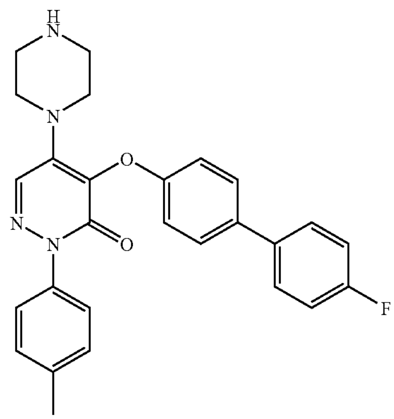 | MS (B): 457 (M + H) (100)<br>HPLC: 7.12 (95) | 7 |
| 105 | 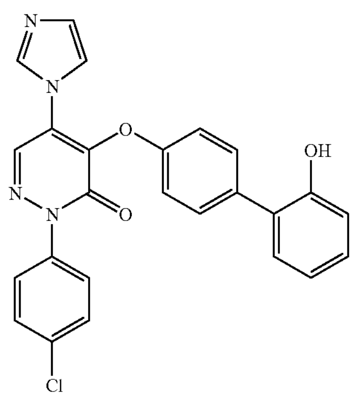 | MS (B): 457 (M + H) (100)<br>HPLC: 7.90 (93) | 10 |
| 106 | 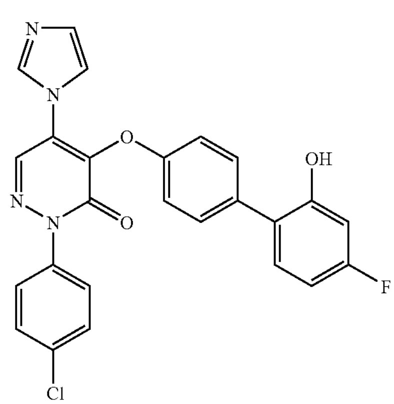 | MS (B): 475 (M + H) (100)<br>HPLC: 3.78 (99) | 10 |

| Example No. | Structure | Analysis (data in ° C. relate to the melting point) | General process |
|---|---|---|---|
| 107 | 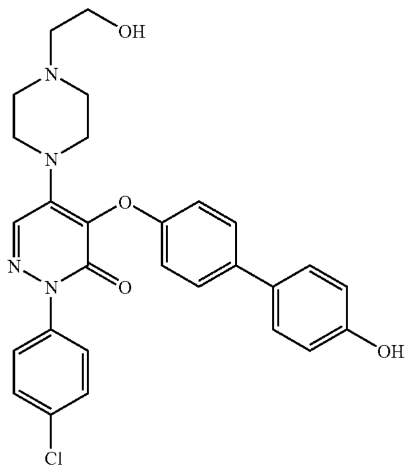 | MS (B): 519 (M + H) (100)<br>HPLC: 6.48 (100) | 10 |
| 108 | 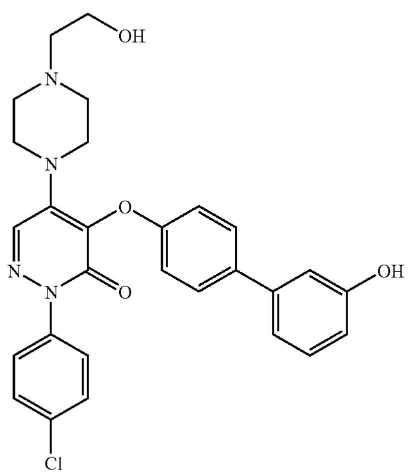 | MS (B): 519 (M + H) (100)<br>HPLC: 6.53 (91) | 10 |
| 109 | 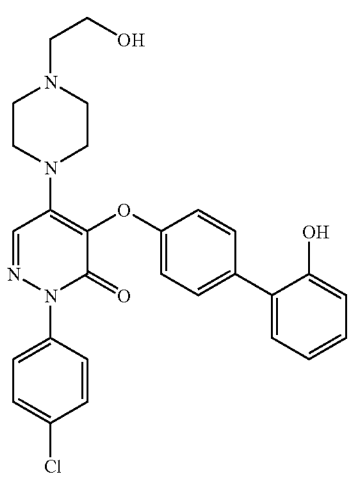 | MS (B): 519 (M + H) (100)<br>HPLC: 6.65 (98) | 10 |

-continued
| Example No. | Structure | Analysis (data in ° C. relate to the melting point) | General process |
|---|---|---|---|
| 110 | 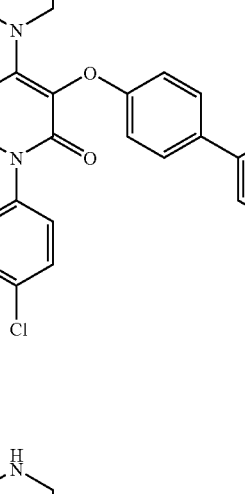 | MS (B): 537 (M + H) (100)<br>HPLC: 6.84 (100) | 10 |
| 111 | 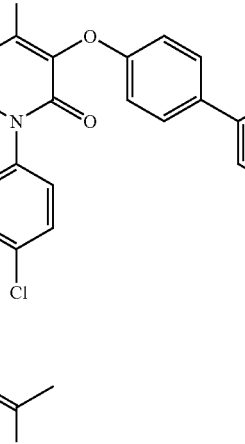 | MS (B): 493 (M + H) (100)<br>HPLC: 6.86 (91) | 10 |
| 112 | 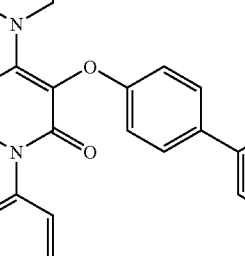 | MS (B): 535 (M + H) (100)<br>HPLC: 8.45 (98) | 10 |

-continued

| Example No. | Structure | Analysis (data in ° C. relate to the melting point) | General process |
|---|---|---|---|
| 113 | 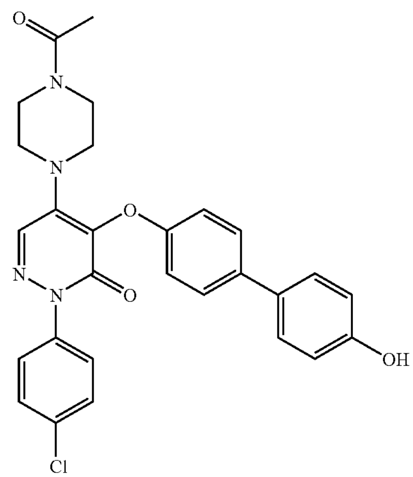 | MS (D): 517/519 (M + H) (100)<br>HPLC: 7.89 (94) | 10 |
| 114 | 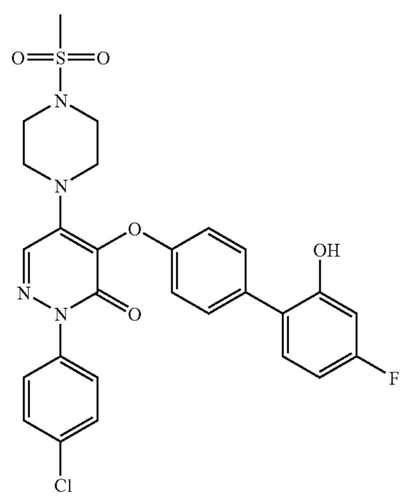 | MS (A): 571 (M + H) (100)<br>HPLC: 9.01 (99) | 10 |
| 115 | 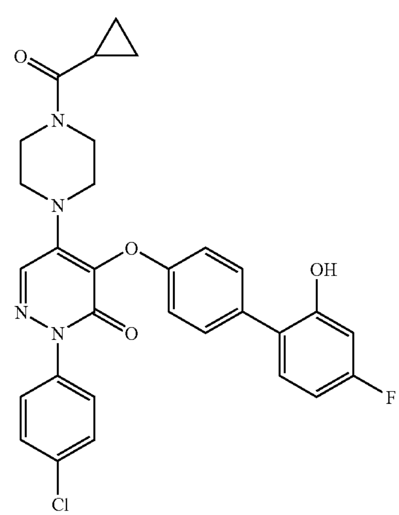 | MS (A): 561 (M + H) (100)<br>HPLC: 8.97 (96) | 10 |

-continued

| Example No. | Structure | Analysis (data in ° C. relate to the melting point) | General process |
|---|---|---|---|
| 116 | 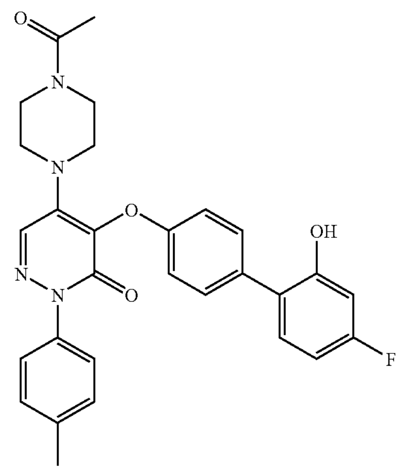 | MS (A): 515 (M + H) (100) HPLC: 8.18 (99) | 10 |
| 117 | 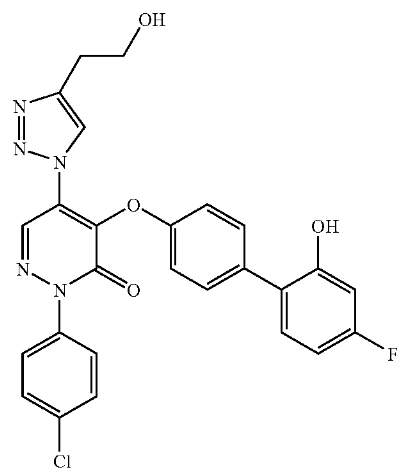 | MS (D): 520 (M + H) (100) HPLC: 8.72 (100) | 10 |
| 118 | 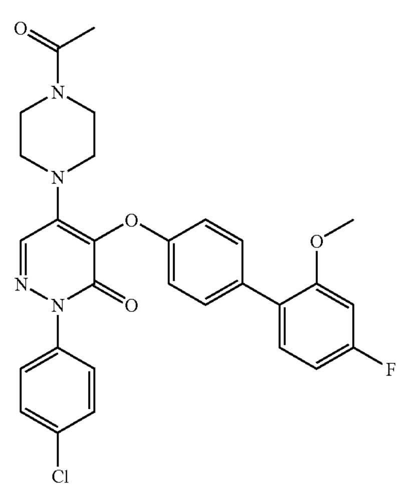 | MS (D): 549/551 (M + H) (100) HPLC: 9.31 (99) | 11 |

-continued
| Example No. | Structure | Analysis (data in ° C. relate to the melting point) | General process |
|---|---|---|---|
| 119 | 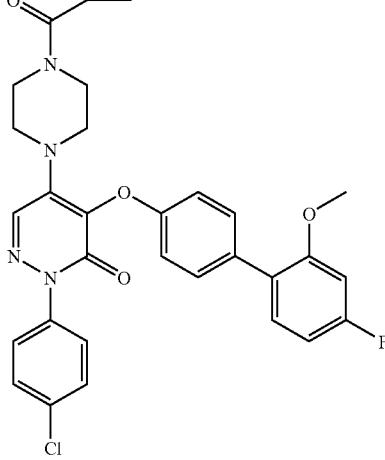 | MS (A): 575 (M + H) (100)<br>HPLC: 9.72 (97) | 11 |
| 120 | 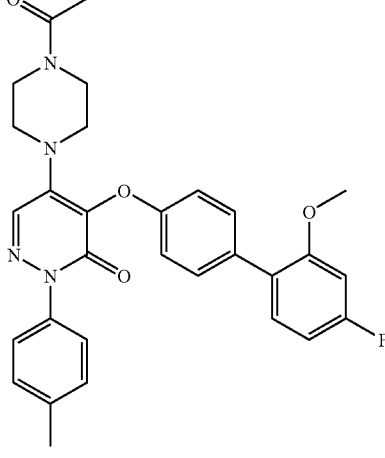 | MS (B): 529 (M + H) (100)<br>HPLC: 8.89 (95) | 11 |
| 121 | 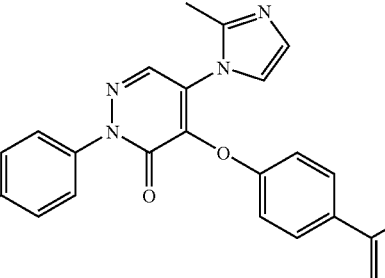 | MS (A): 455 (M + H) (100)<br>HPLC: 7.94 (94) | 16a |

-continued

| Example No. | Structure | Analysis (data in ° C. relate to the melting point) | General process |
|---|---|---|---|
| 122 | 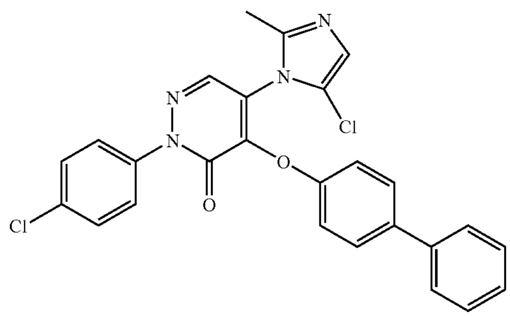 | MS (A): 489 (M + H) (100) HPLC: 10.15 (94) | 16a |
| 123 | 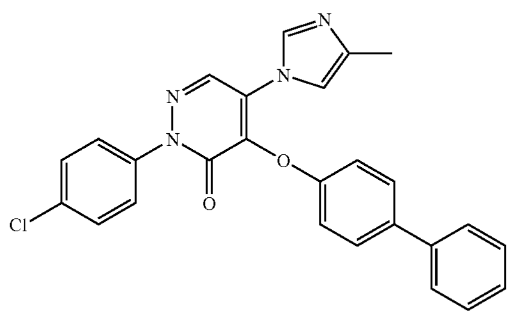 | MS (A): 455 (M + H) (100) HPLC: 8.15 (95) | 16a |
| 124 | 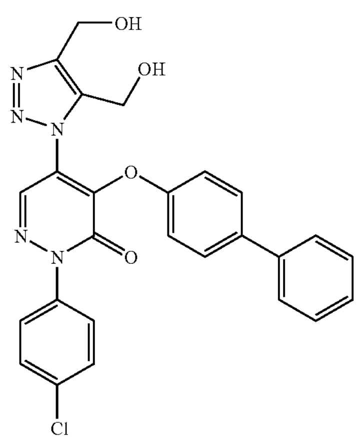 | MS (B): 502 (M + H) (100) HPLC: 8.69 (98) | 14 |
| 125 | 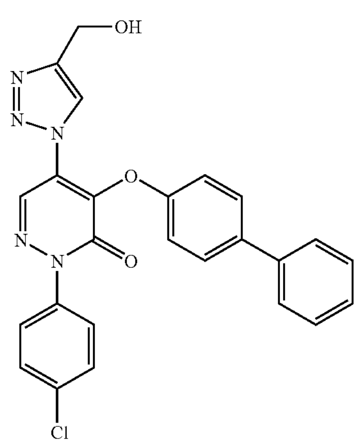 | MS (B): 472 (M + H) (100) HPLC: 9.33 (99) | 14 |

-continued
| Example No. | Structure | Analysis (data in ° C. relate to the melting point) | General process |
|---|---|---|---|
| 126 | 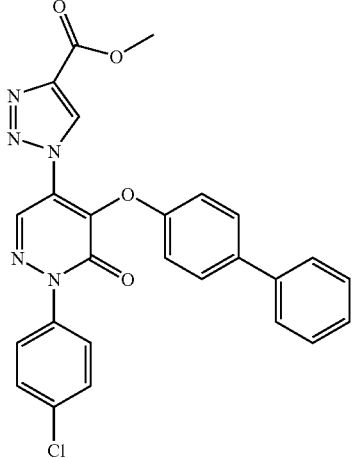 | MS (B): 500 (M + H) (100) HPLC: 10.20 (98) | 14 |
| 127 | 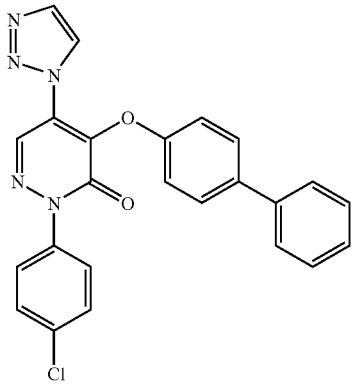 | MS (B): 442 (M + H) (100) HPLC: 10.12 (96) | 14 |
| 128 | 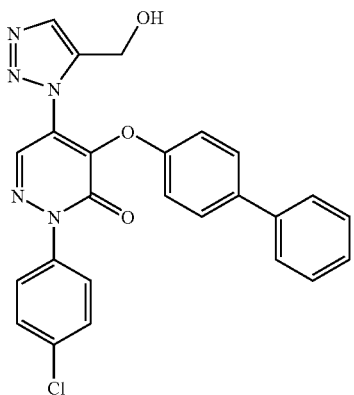 | MS (B): 472 (M + H) (100) HPLC: 9.20 (84) | 14 |

-continued

| Example No. | Structure | Analysis (data in °C. relate to the melting point) | General process |
|---|---|---|---|
| 129 | 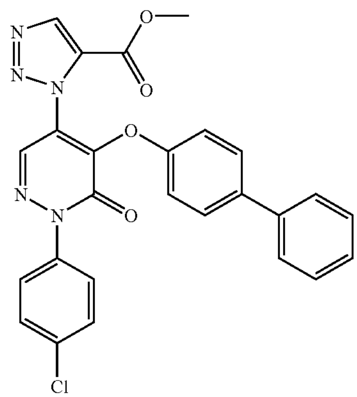 | MS (B): 500 (M + H) (100)<br>HPLC: 10.21 (96) | 14 |
| 130 | 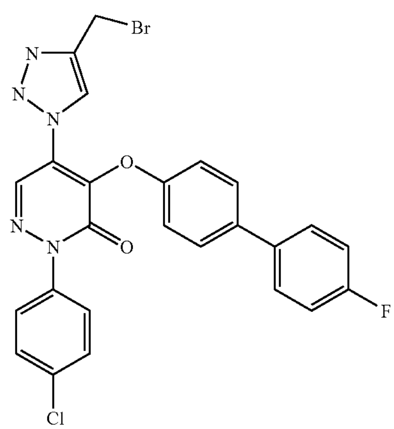 | MS (D): 552/554 (M + H) (100)<br>HPLC: 10.60 (97) | 14 |
| 131 | 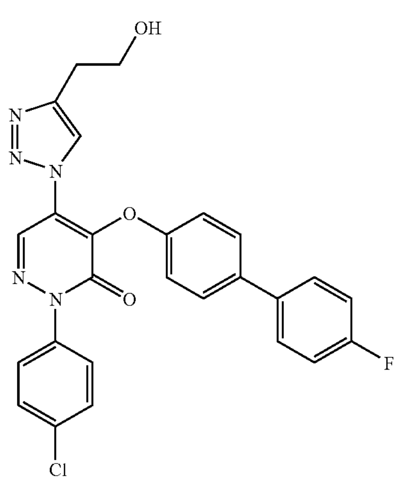 | MS (A): 504 (M + H) (100)<br>HPLC: 9.37 (98) | 14 |

-continued

| Example No. | Structure | Analysis (data in ° C. relate to the melting point) | General process |
|---|---|---|---|
| 132 | 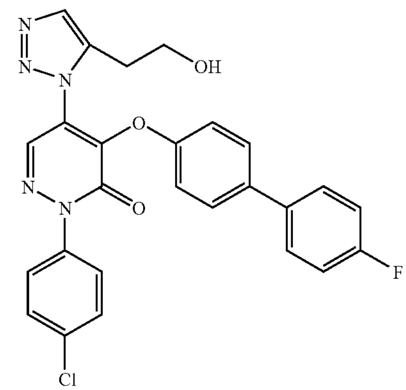 | MS (B): 504 (M + H) (100)<br>HPLC: 9.16 (100) | 14 |
| 133 | 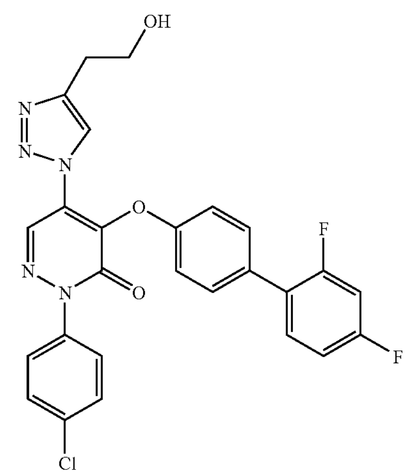 | MS (B): 522 (M + H) (100)<br>HPLC: 9.78 (96) | 14 |
| 134 | 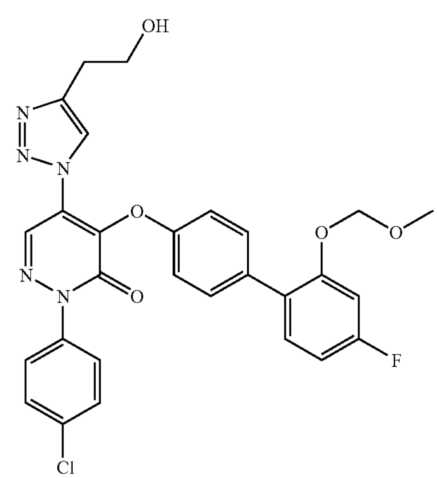 | MS (B): 564 (M + H) (100)<br>HPLC: 9.94 (99) | 14 |

-continued
| Example No. | Structure | Analysis (data in ° C. relate to the melting point) | General process |
|---|---|---|---|
| 135 | 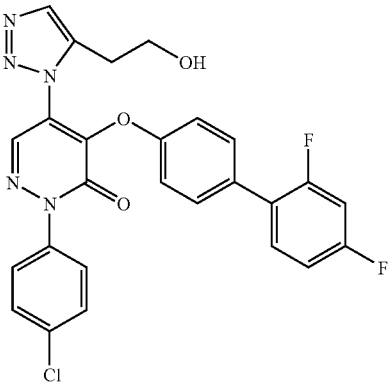 | MS (D): 522 (M + H) (100)<br>HPLC: 9.22 (94) | 14 |
| 136 | 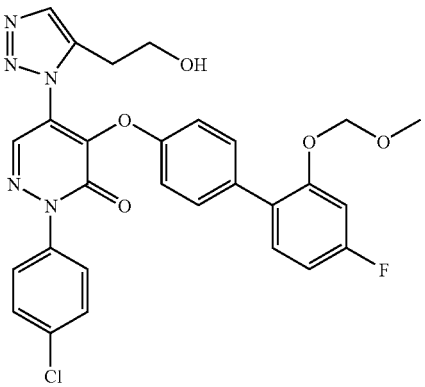 | MS (B): 563 (M + ) (38)<br>HPLC: 9.67 (99) | 14 |
| 137 | 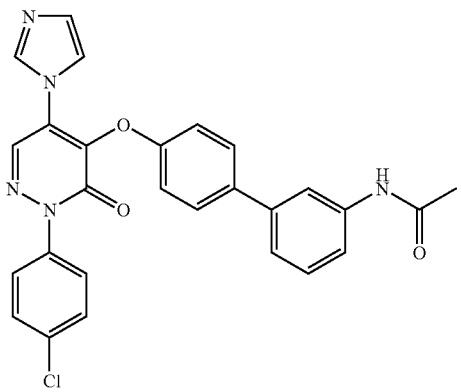 | MS (B): 498 (M + H) (100)<br>HPLC: 7.58 (96) | 2 |

-continued

| Example No. | Structure | Analysis (data in °C. relate to the melting point) | General process |
|---|---|---|---|
| 138 | 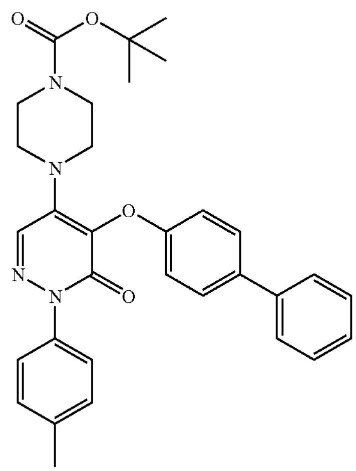 | MS (A): 539 (M + H) (100)<br>HPLC: 10.89 (98) | 6-a |
| 139 | 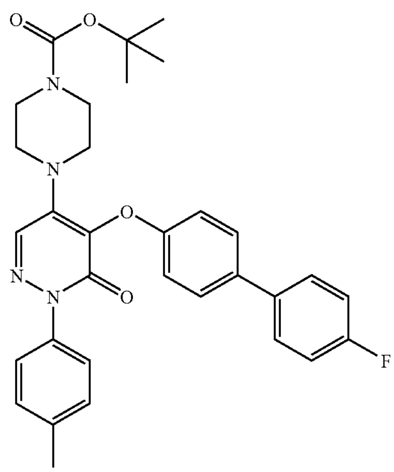 | MS (B): 557 (M + H) (100) | 6-a |
| 140 | 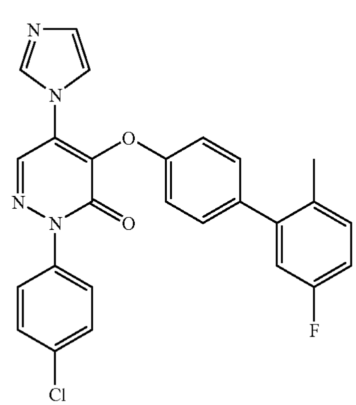 | MS (B): 473 (M + H) (100)<br>HPLC: 9.25 (94) | 9-a |

-continued

| Example No. | Structure | Analysis (data in ° C. relate to the melting point) | General process |
|---|---|---|---|
| 141 | (structure) | MS (A): 473 (M + NH₄) (100), 456 (M + H) (52)<br>HPLC: 6.64 (97) | 9-a |
| 142 | (structure) | MS (B): 521 (M + H) (100)<br>HPLC: 7.45 (98) | 9-a |
| 143 | (structure) | MS (D): 490 (M + H) (100)<br>HPLC: 9.36 (99) | 9-a |

-continued

| Example No. | Structure | Analysis (data in ° C. relate to the melting point) | General process |
|---|---|---|---|
| 144 | 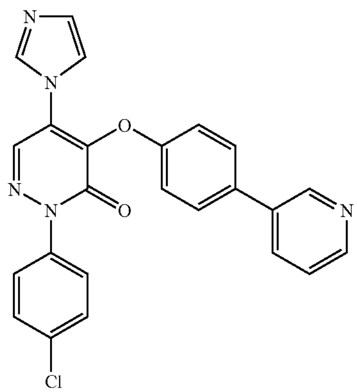 | MS (A): 442/444 (M + H) (100)<br>HPLC: 6.75 (98) | 9-b |
| 145 | 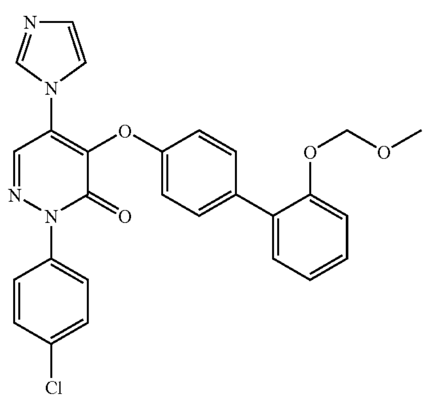 | MS (C): 500 (M) (100)<br>HPLC: 8.80 (97) | 9-b |
| 146 | 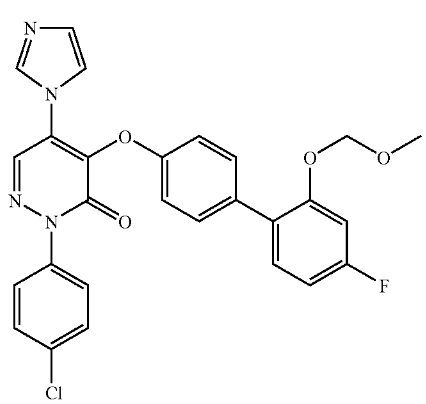 | MS (B): 541 (M + Na) (100),<br>519 (M + H) (74)<br>HPLC: 8.95 (96) | 9-b |

-continued

| Example No. | Structure | Analysis (data in ° C. relate to the melting point) | General process |
|---|---|---|---|
| 147 | 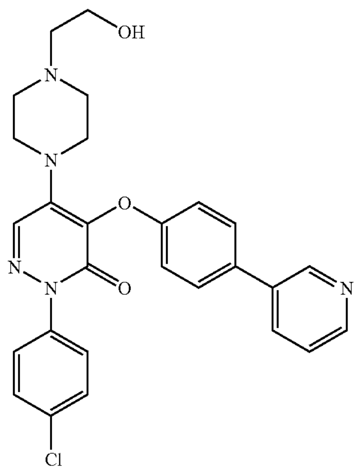 | MS (B): 504 (M + H) (100)<br>HPLC: 5.20 (96) | 9-b |
| 148 | 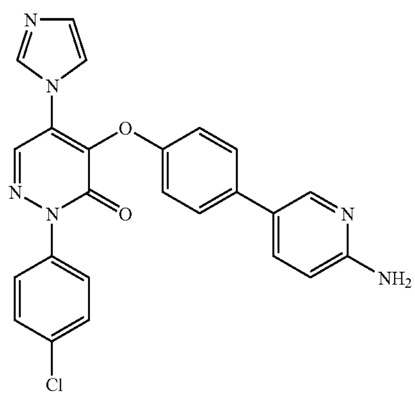 | MS (B): 457 (M + H) (100)<br>HPLC: 5.93 (95) | 9-b |
| 149 | 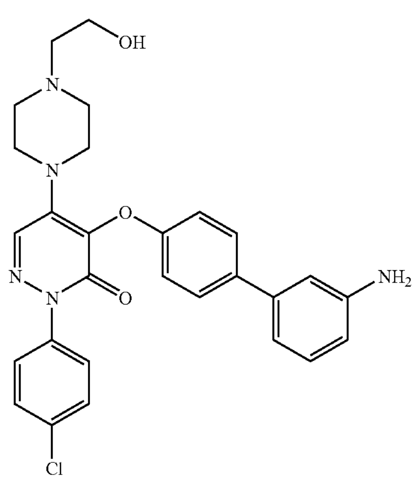 | MS (A): 518 (M + H) (100)<br>HPLC: 5.55 (96) | 9-b |

-continued

| Example No. | Structure | Analysis (data in ° C. relate to the melting point) | General process |
|---|---|---|---|
| 150 | 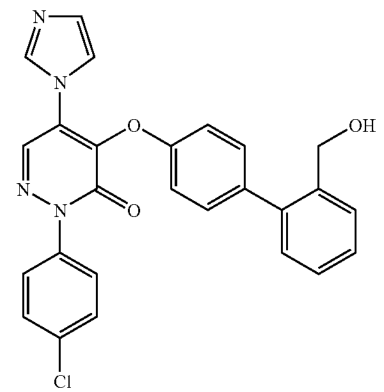 | MS (B): 471 (M + H) (100) HPLC: 7.71 (96) | 9-b |
| 151 | 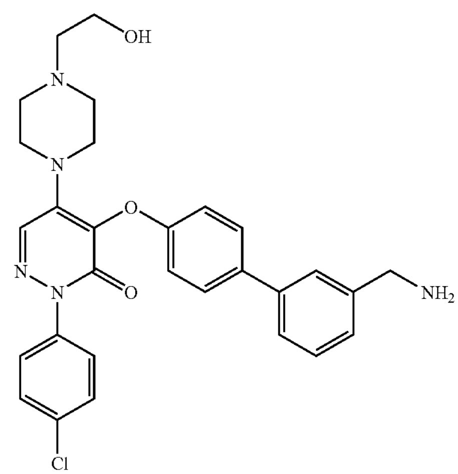 | MS (B): 532 (M + H) (100) HPLC: 5.32 (96) | 9-b |
| 152 | 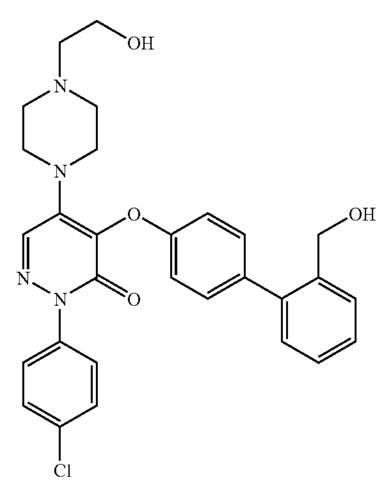 | MS (B): 533 (M + H) (100) HPLC: 6.68 (99) | 9-b |

-continued

| Example No. | Structure | Analysis (data in ° C. relate to the melting point) | General process |
|---|---|---|---|
| 153 | 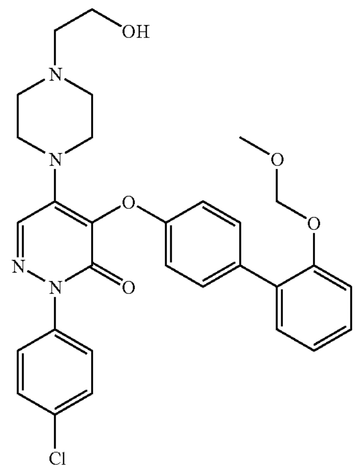 | MS (A): 563 (M + H) (100) HPLC: 7.30 (97) | 9-b |
| 154 | 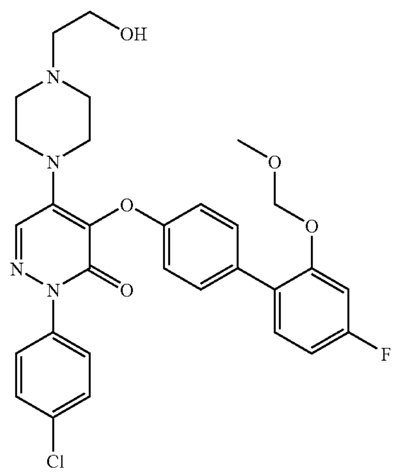 | MS (A): 581 (M + H) (100) HPLC: 7.51 (96) | 9-b |
| 155 | 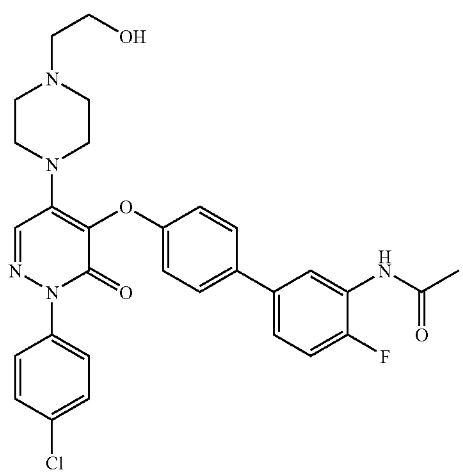 | MS (B): 578 (M + H) (100) HPLC: 6.51 (93) | 9-b |

-continued

| Example No. | Structure | Analysis (data in ° C. relate to the melting point) | General process |
|---|---|---|---|
| 156 | 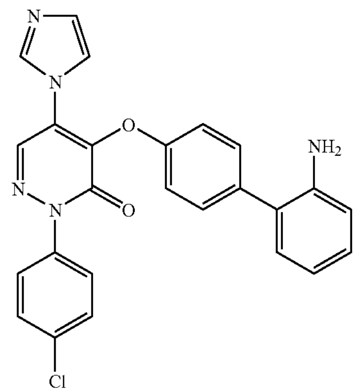 | MS (D): 456 (M + H) (100)<br>HPLC: 3.83 (97) | 9-b |
| 157 | 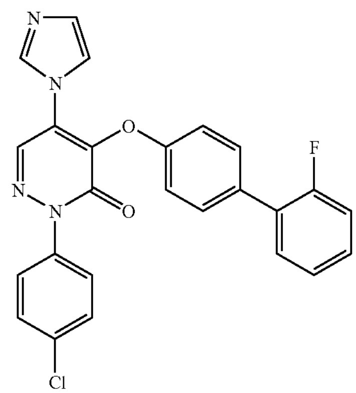 | MS (D): 459/461 (M + H) (100)<br>HPLC: 4.47 (100) | 9-b |
| 158 | 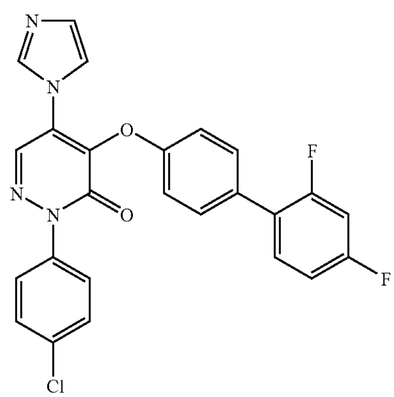 | MS (D): 477/479 (M + H) (100)<br>HPLC: 4.53 (100) | 9-b |
| 159 | 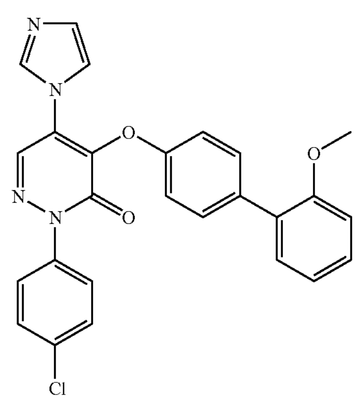 | MS (D): 471/473 (M + H) (100)<br>HPLC: 4.45 (100) | 9-b |

-continued
| Example No. | Structure | Analysis (data in ° C. relate to the melting point) | General process |
|---|---|---|---|
| 160 | 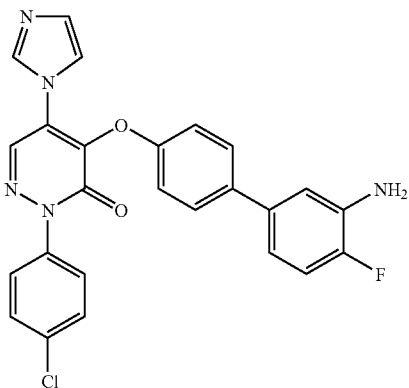 | MS (D): 474 (M + H) (100)<br>HPLC: 4.05 (98) | 9-b |
| 161 | 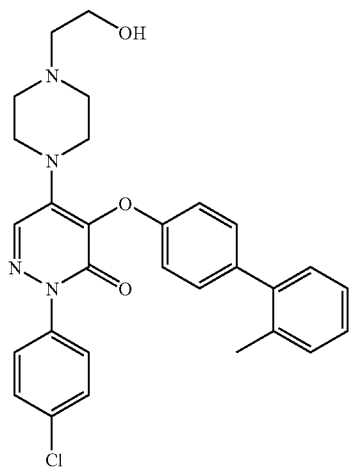 | MS (F): 517 (M + H) (100) | 9-b |
| 162 | 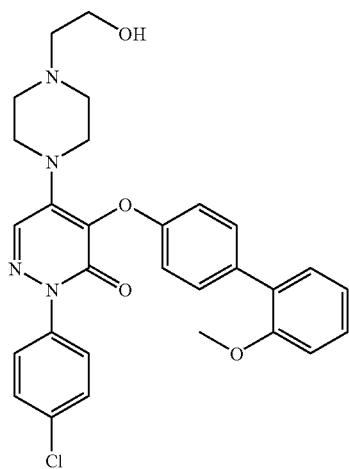 | MS (F): 533 (M + H) (100) | 9-b |

-continued
| Example No. | Structure | Analysis (data in ° C. relate to the melting point) | General process |
|---|---|---|---|
| 163 | 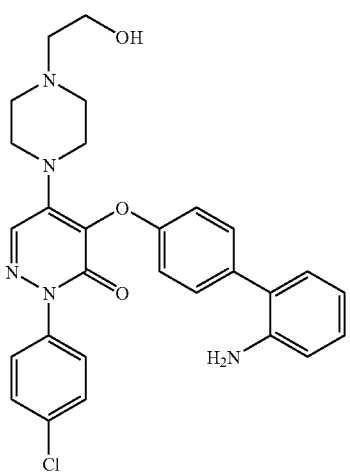 | MS (F): 518 (M + H) (100) | 9-b |
| 164 | 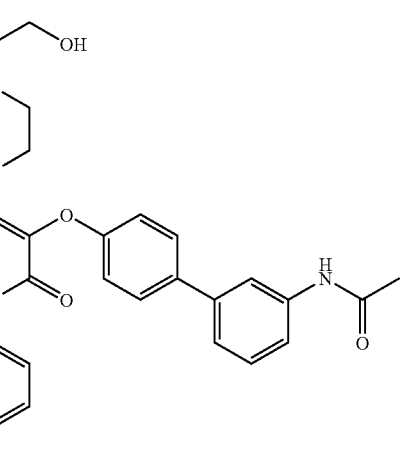 | MS (F): 560 (M + H) (100) | 9-b |
| 165 | 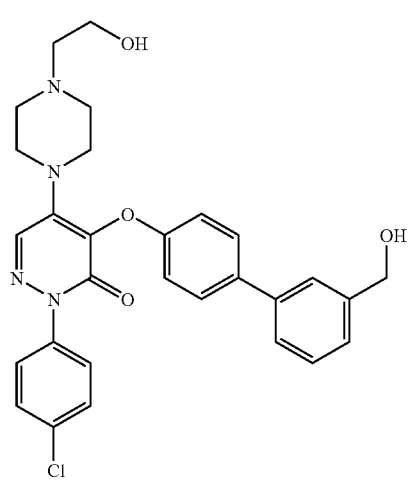 | MS (F): 533 (M + H) (100) | 9-b |

-continued

| Example No. | Structure | Analysis (data in ° C. relate to the melting point) | General process |
|---|---|---|---|
| 166 | 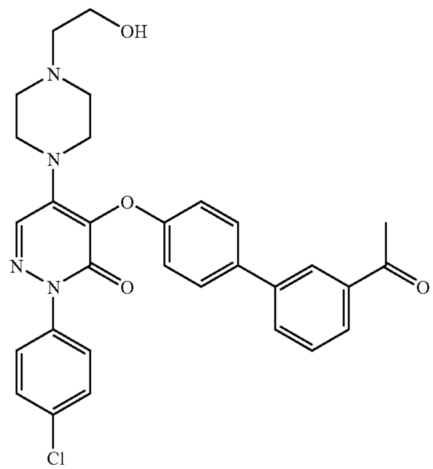 | MS (F): 545 (M + H) (100) | 9-b |
| 167 | 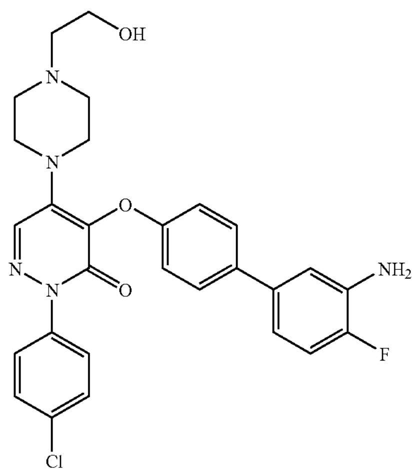 | MS (F): 536 (M + H) (100) | 9-b |
| 168 | 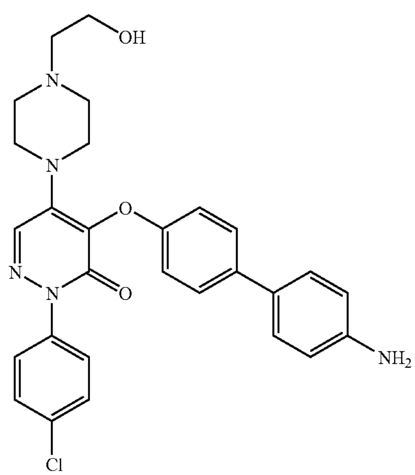 | MS (F): 518 (M + H) (100) | 9-b |

-continued

| Example No. | Structure | Analysis (data in ° C. relate to the melting point) | General process |
|---|---|---|---|
| 169 | 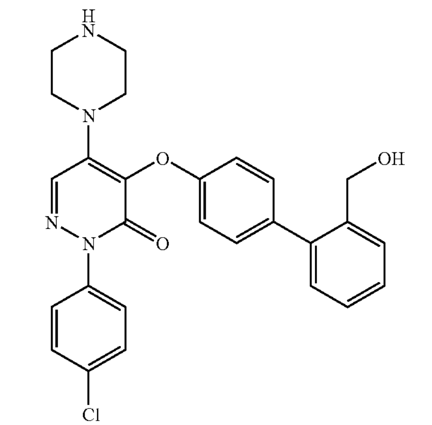 | MS (B): 489 (M + H) (100)<br>HPLC: 6.60 (98) | 9-c |
| 170 | 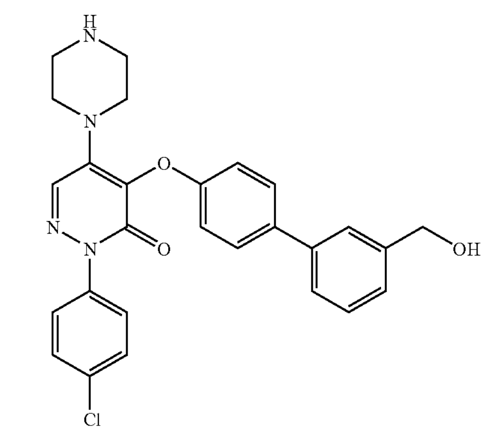 | MS (A): 489 (M + H) (100)<br>HPLC: 6.48 (98) | 9-c |
| 171 | 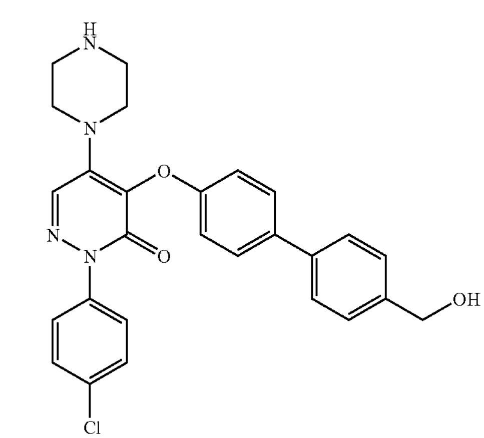 | MS (B): 489 (M + H) (100)<br>HPLC: 6.37 (96) | 9-c |

-continued

| Example No. | Structure | Analysis (data in ° C. relate to the melting point) | General process |
|---|---|---|---|
| 172 | 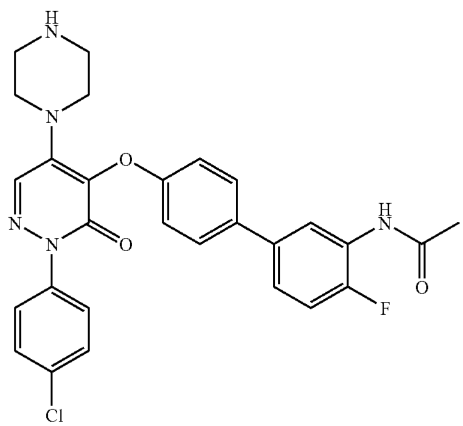 | MS (B): 534 (M + H) (100)<br>HPLC: 6.55 (97) | 9-c |
| 173 | 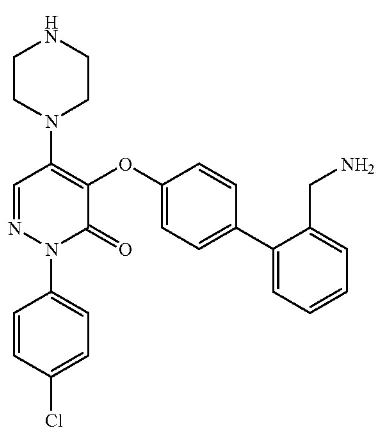 | MS (B): 488 (M + H) (100)<br>HPLC: 6.33 (99) | 9-c |
| 174 | 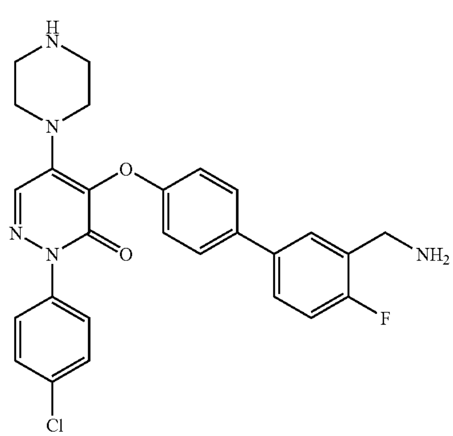 | MS (B): 506 (M + H) (100)<br>HPLC: 5.39 (98) | 9-c |

-continued

| Example No. | Structure | Analysis (data in ° C. relate to the melting point) | General process |
|---|---|---|---|
| 175 | 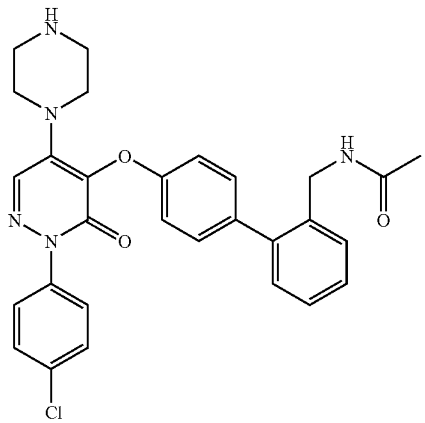 | MS (B): 530 (M + H) (100)<br>HPLC: 6.54 (100) | 9-c |
| 176 | 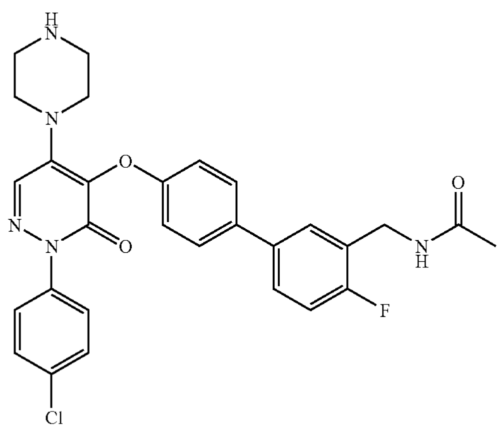 | MS (B): 548 (M + H) (100)<br>HPLC: 6.55 (98) | 9-c |
| 177 | 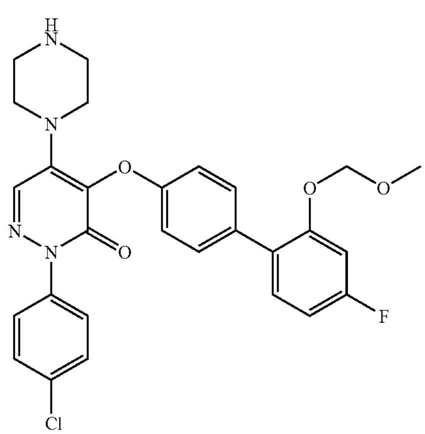 | MS (B): 537 (M + H) (100)<br>HPLC: 7.46 (94) | 9-c |

-continued

| Example No. | Structure | Analysis (data in °C. relate to the melting point) | General process |
|---|---|---|---|
| 178 | 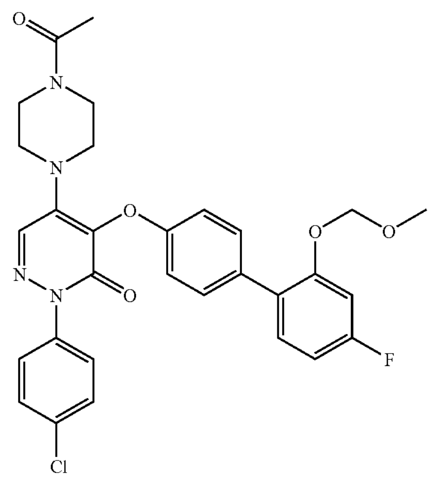 | MS (B): 579 (M + H) (100)<br>HPLC: 9.21 (93) | 9-c |
| 179 | 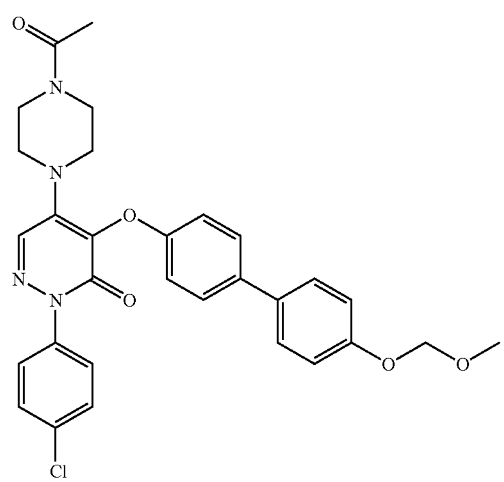 | MS (B): 561 (M + H) (100)<br>HPLC: 8.91 (99) | 9-c |
| 180 | 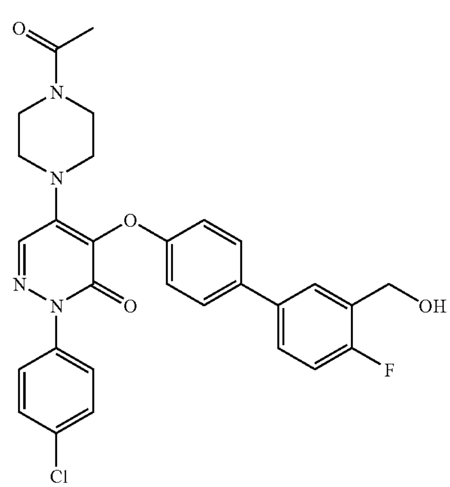 | MS (E): 549 (M + H) (100)<br>HPLC: 8.04 (97) | 9-c |

-continued

| Example No. | Structure | Analysis (data in ° C. relate to the melting point) | General process |
|---|---|---|---|
| 181 | 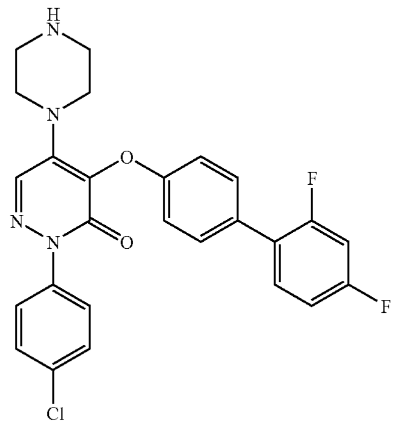 | MS (B): 495 (M + H) (100)<br>HPLC: 7.47 (94) | 9-c |
| 182 | 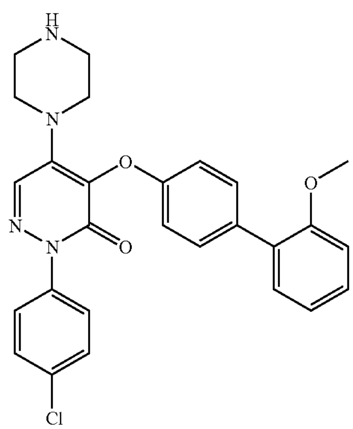 | MS (B): 489 (M + H) (100)<br>HPLC: 7.25 (92) | 9-c |
| 183 | 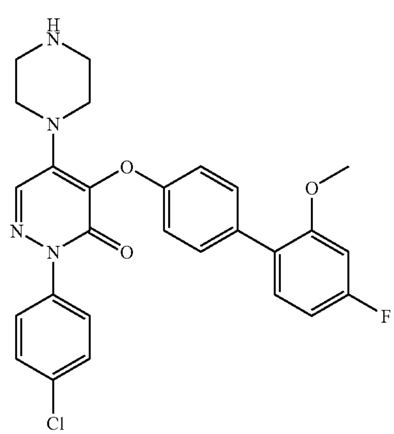 | MS (D): 507 (M + H) (100)<br>HPLC: 7.40 (91) | 9-c |

-continued

| Example No. | Structure | Analysis (data in ° C. relate to the melting point) | General process |
|---|---|---|---|
| 184 | 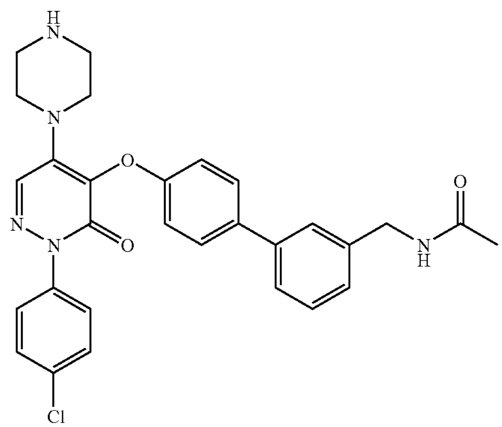 | MS (D): 530 (M + H) (100)<br>HPLC: 6.37 (96) | 9-c |
| 185 | 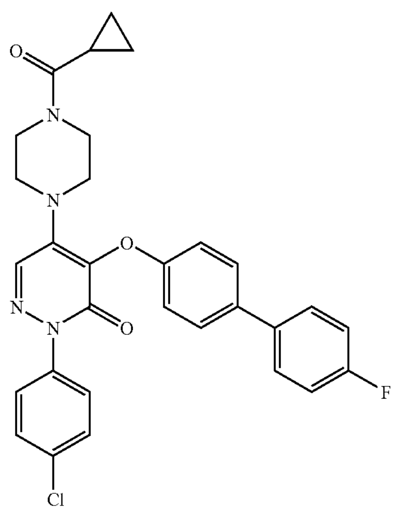 | MS (A): 545 (M + H) (100)<br>HPLC: 9.67 (92) | 9-c |
| 186 | 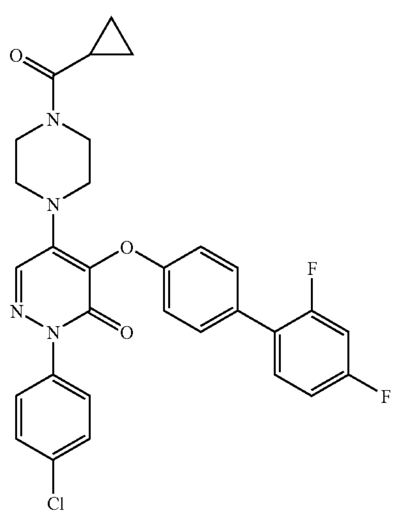 | MS (A): 563 (M + H) (100)<br>HPLC: 9.77 (91) | 9-c |

-continued
| Example No. | Structure | Analysis (data in ° C. relate to the melting point) | General process |
|---|---|---|---|
| 187 | 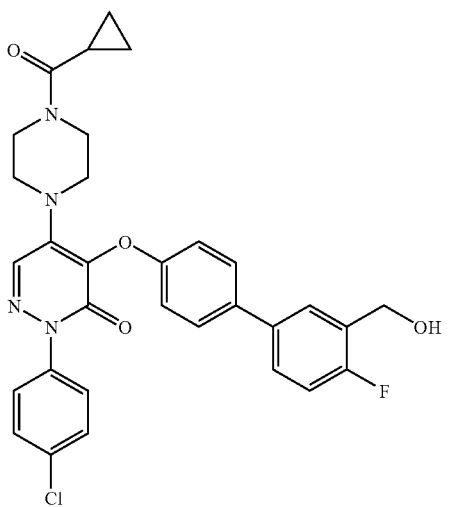 | MS (D): 575 (M + H) (100)<br>HPLC: 8.57 (97) | 9-c |
| 188 | 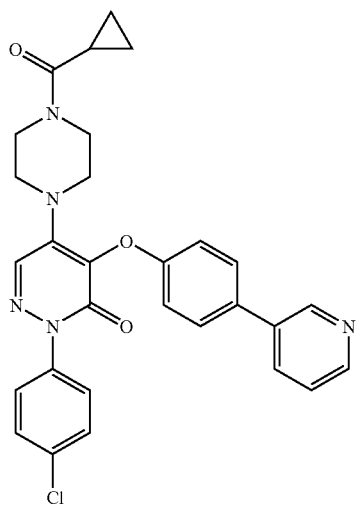 | MS (D): 528 (M + H) (100)<br>HPLC: 6.55 (95) | 9-c |
| 189 | 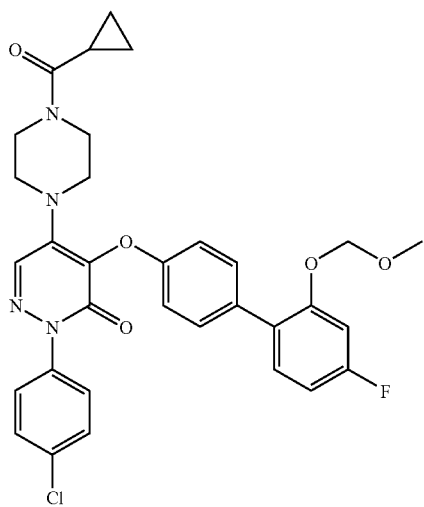 | MS (A): 605 (M + H) (100)<br>HPLC: 9.74 (99) | 9-c |

-continued

| Example No. | Structure | Analysis (data in ° C. relate to the melting point) | General process |
|---|---|---|---|
| 190 | 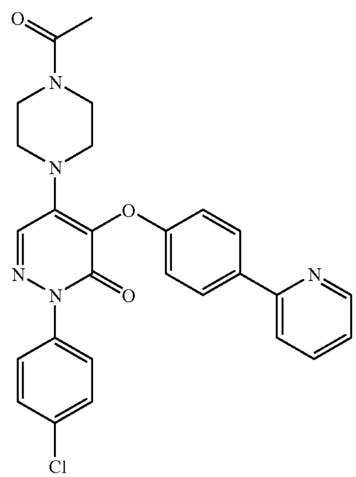 | MS (A): 502 (M + H) (100)<br>HPLC: 6.16 (92) | 9-c |
| 191 | 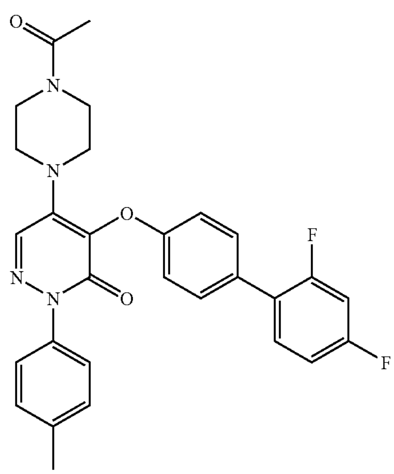 | MS (A): 517 (M + H) (100)<br>HPLC: 8.93 (98) | 9-c |
| 192 | 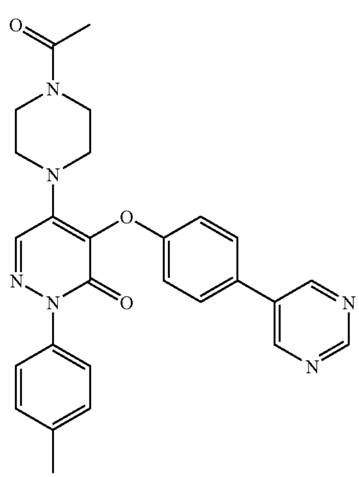 | MS (A): 483 (M + H) (100)<br>HPLC: 6.79 (98) | 9-c |

-continued

| Example No. | Structure | Analysis (data in ° C. relate to the melting point) | General process |
|---|---|---|---|
| 193 | 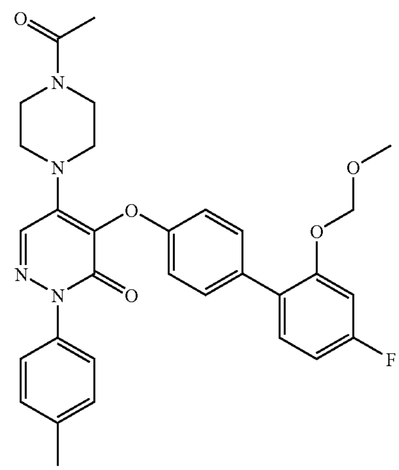 | MS (A): 559 (M + H) (100)<br>HPLC: 8.92 (97) | 9-c |
| 194 | 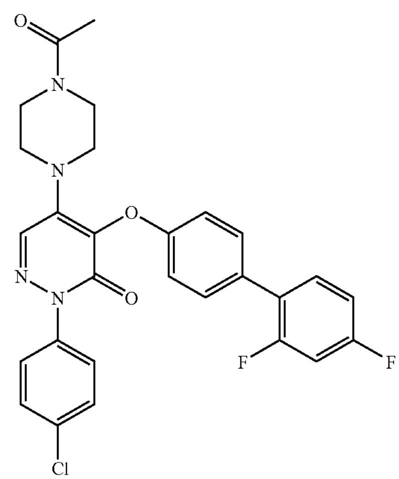 | MS (F): 537 (M + H) (100)<br>HPLC: 4.59 (100) | 9-c |
| 195 | 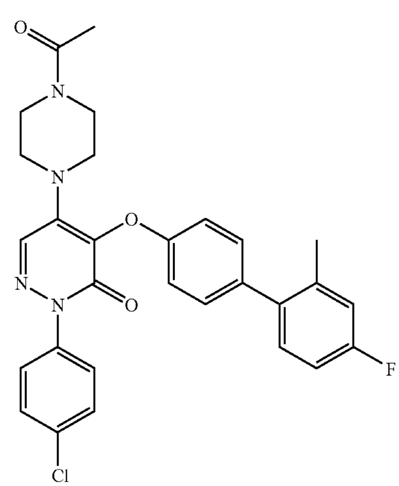 | MS (F): 533 (M + H) (100)<br>HPLC: 4.69 (100) | 9-c |

-continued

| Example No. | Structure | Analysis (data in ° C. relate to the melting point) | General process |
|---|---|---|---|
| 196 | 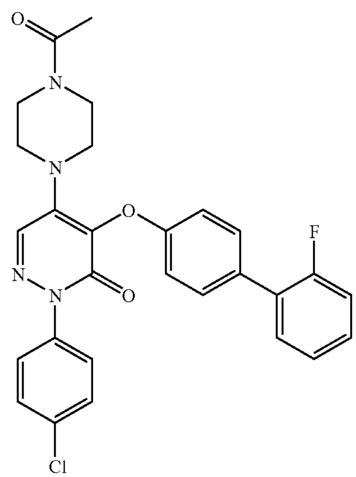 | MS (F): 519 (M + H) (100)<br>HPLC: 4.51 (100) | 9-c |
| 197 | 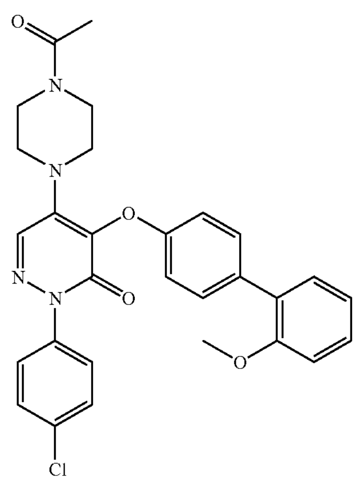 | MS (F): 531 (M + H) (100)<br>HPLC: 4.50 (100) | 9-c |
| 198 | 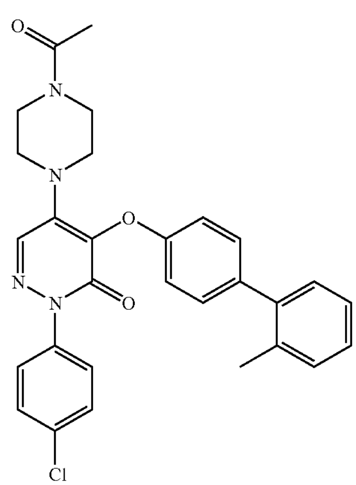 | MS (F): 515 (M + H) (100)<br>HPLC: 4.64 (100) | 9-c |

-continued

| Example No. | Structure | Analysis (data in ° C. relate to the melting point) | General process |
|---|---|---|---|
| 199 | 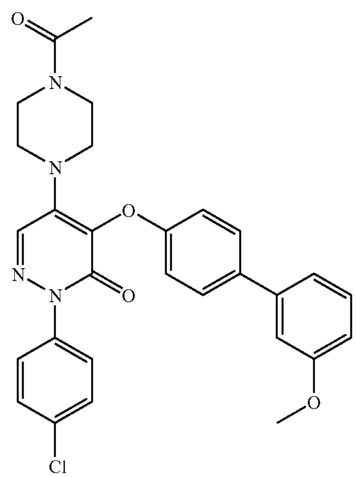 | MS (F): 531 (M + H) (100)<br>HPLC: 4.47 (100) | 9-c |
| 200 | 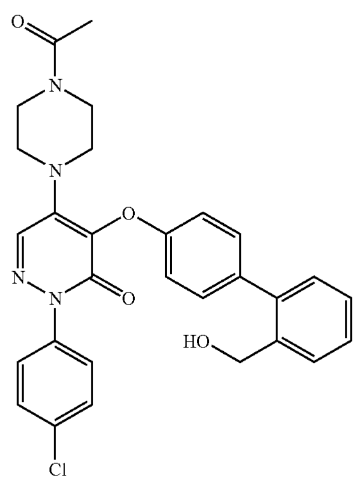 | MS (F): 531 (M + H) (100)<br>HPLC: 3.99 (93) | 9-c |
| 201 | 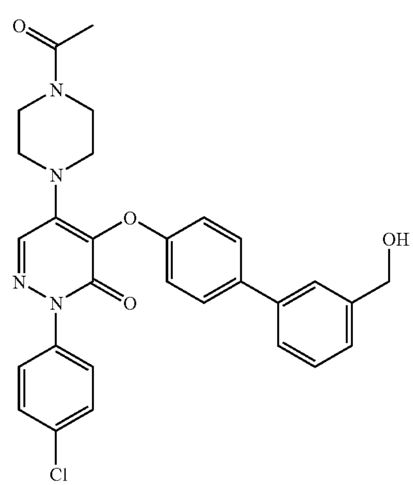 | MS (F): 531 (M + H) (100)<br>HPLC: 3.92 (94) | 9-c |

-continued

| Example No. | Structure | Analysis (data in ° C. relate to the melting point) | General process |
|---|---|---|---|
| 202 | 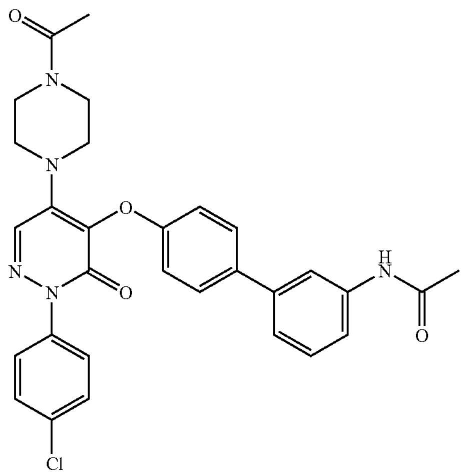 | MS (F): 558 (M + H) (100)<br>HPLC: 3.90 (100) | 9-c |
| 203 | 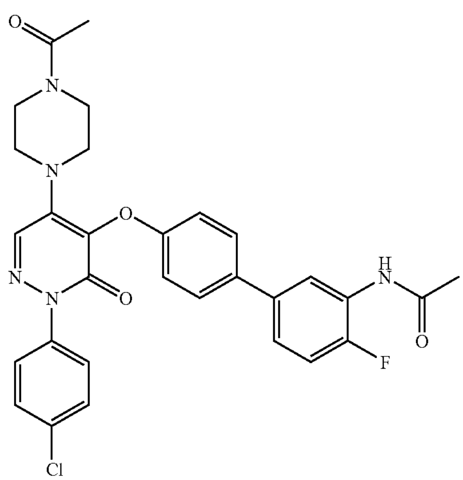 | MS (F): 576 (M + H) (100)<br>HPLC: 3.94 (93) | 9-c |
| 204 | 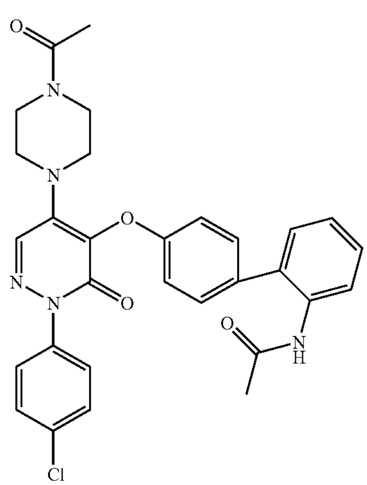 | MS (F): 558 (M + H) (100)<br>HPLC: 3.84 (100) | 9-c |

-continued

| Example No. | Structure | Analysis (data in ° C. relate to the melting point) | General process |
|---|---|---|---|
| 205 | 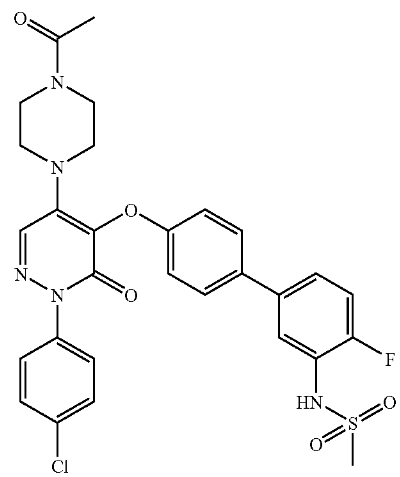 | MS (F): 612 (M + H) (100)<br>HPLC: 4.01 (100) | 9-c |
| 206 | 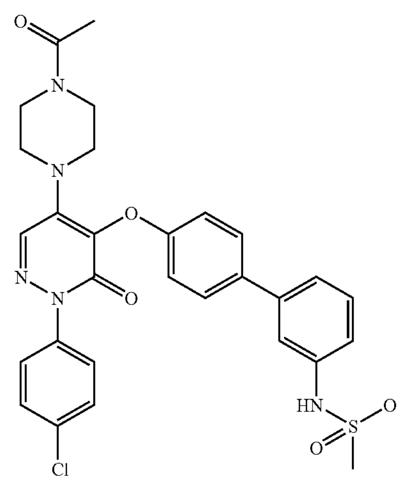 | MS (F): 594 (M + H) (100)<br>HPLC: 4.02 (100) | 9-c |
| 207 | 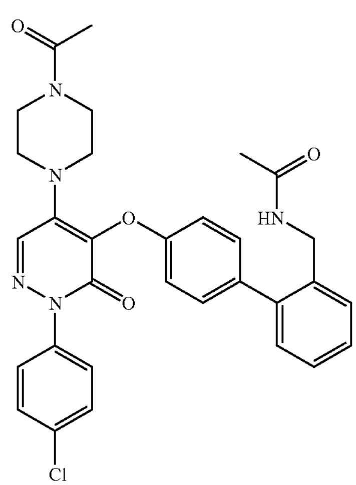 | MS (F): 572 (M + H) (100)<br>HPLC: 3.87 (100) | 9-c |

-continued

| Example No. | Structure | Analysis (data in ° C. relate to the melting point) | General process |
|---|---|---|---|
| 208 | 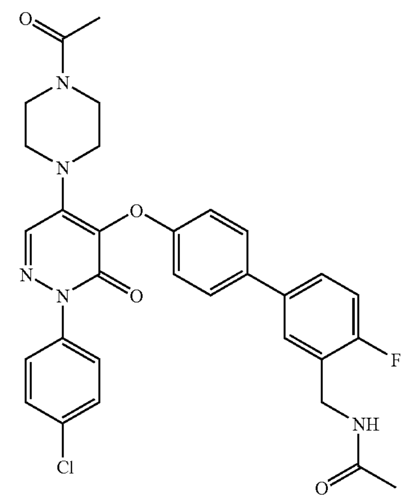 | MS (F): 590 (M + H) (100)<br>HPLC: 3.90 (100) | 9-c |
| 209 | 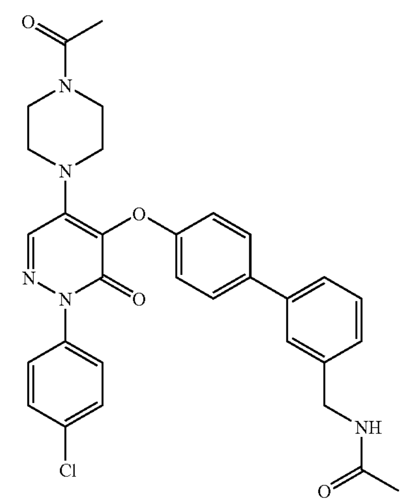 | MS (F): 572 (M + H) (100)<br>HPLC: 3.84 (100) | 9-c |
| 210 | 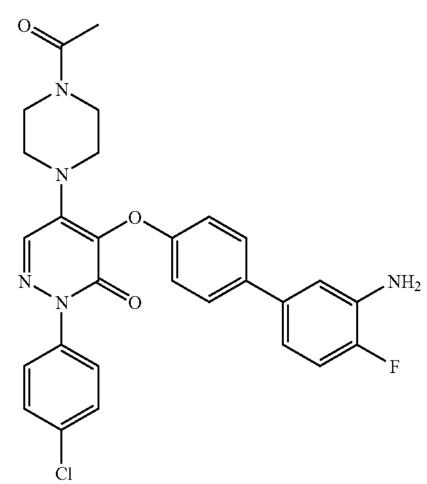 | MS (F): 534 (M + H) (100)<br>HPLC: 4.00 (100) | 9-c |

-continued

| Example No. | Structure | Analysis (data in ° C. relate to the melting point) | General process |
|---|---|---|---|
| 211 | 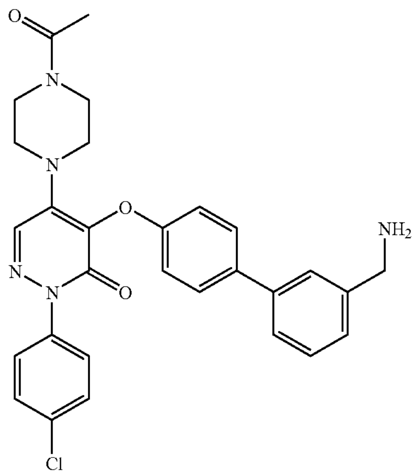 | MS (F): 530 (M + H) (100)<br>HPLC: 3.27 (100) | 9-c |
| 212 | 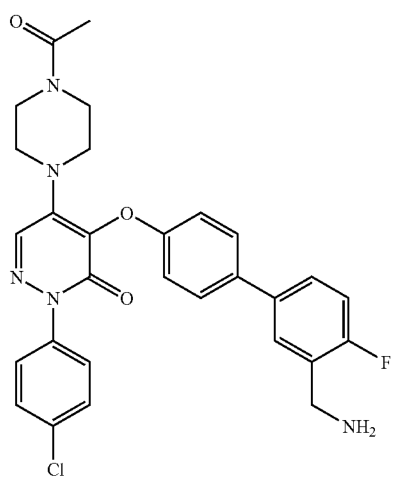 | MS (F): 548 (M + H) (100)<br>HPLC: 3.28 (100) | 9-c |
| 213 | 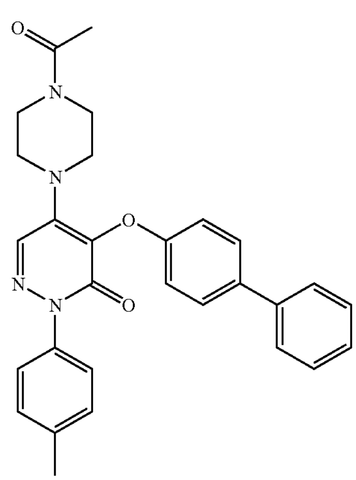 | MS (C): 481 (M + H) (100);<br>HPLC: 8.77 (98) | 3 |

-continued

| Example No. | Structure | Analysis (data in ° C. relate to the melting point) | General process |
|---|---|---|---|
| 214 | 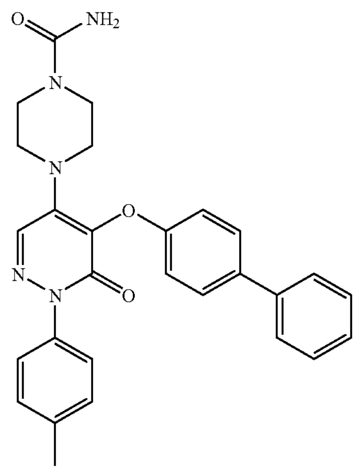 | MS (C): 482 (M + H) (100); HPLC: 8.22 (82) | 5 |
| 215 | 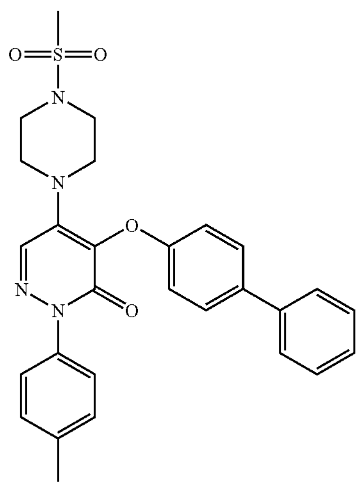 | MS (C): 517 (M + H) (100); HPLC: 9.38 (97) | 4 |
| 216 | 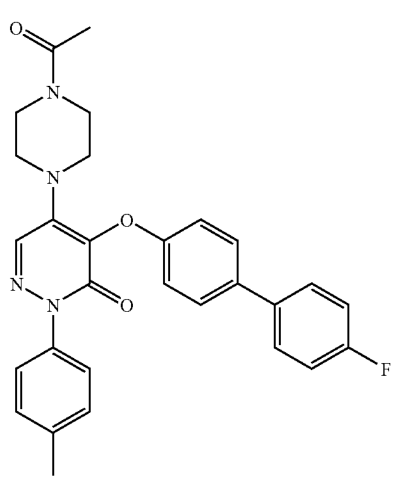 | MS (C): 499 (M + H) (100); HPLC: 8.84 (100) | 2 |

-continued

| Example No. | Structure | Analysis (data in ° C. relate to the melting point) | General process |
|---|---|---|---|
| 217 | 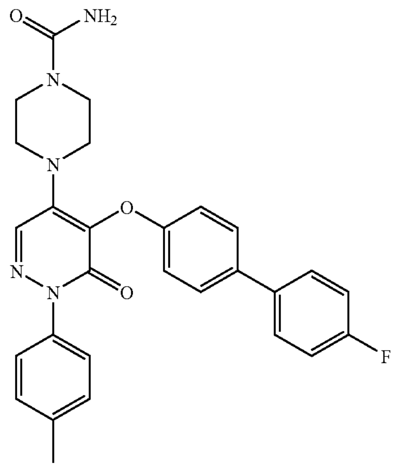 | MS (C): 500 (M + H) (100); HPLC: 8.28 (89) | 5 |
| 218 | 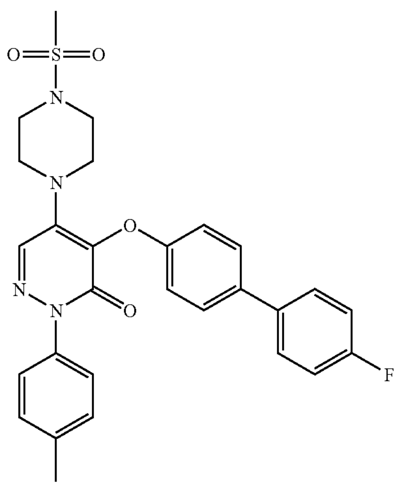 | MS (C): 535 (M + H) (100); HPLC: 9.44 (94) | 4 |
| 219 | 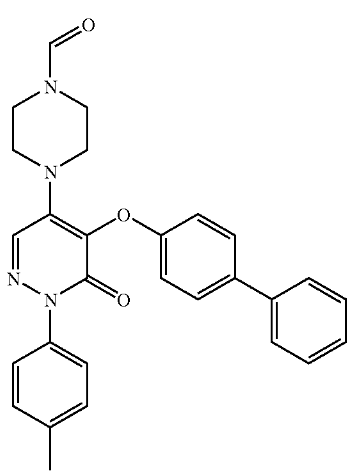 | MS (C): 467 (M + H) (100); HPLC: 8.73 (99) | 3 |

-continued
| Example No. | Structure | Analysis (data in ° C. relate to the melting point) | General process |
|---|---|---|---|
| 220 | 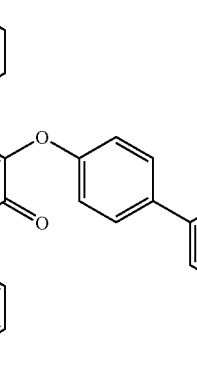 | MS (C): 485 (M + H) (100); HPLC: 8.80 (86) | 3 |
| 221 | 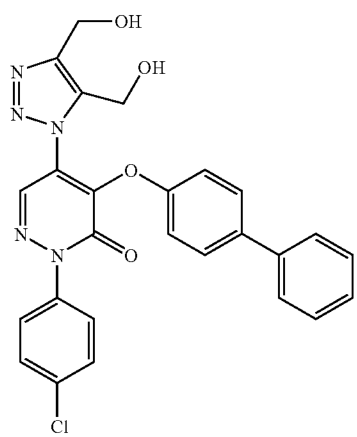 | MS (C): 558 (M + H) (100); HPLC: 10.32 (99) | 14 |
| 222 | 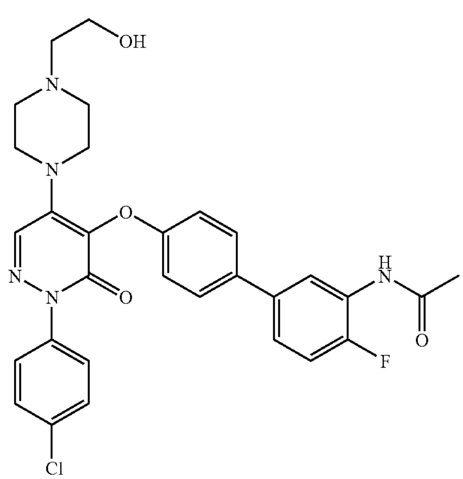 | | 1 |

| Example No. | Structure | Analysis (data in °C. relate to the melting point) | General process |
|---|---|---|---|
| 223 | 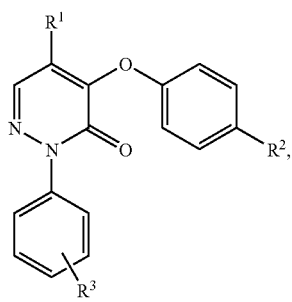 | MS (C): 582 (M + H) (100); HPLC: 7.39 (96) | 1 |

The invention claimed is:

1. A compound of the formula (I)

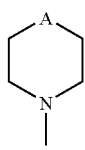

in which

R¹ is 5- to 7-membered, saturated or partially unsaturated heterocyclyl which is linked via a ring nitrogen atom and optionally has a further heteroatom or hetero chain member from the series N, O, S, SO or $SO_2$, and which may be substituted once or twice, identically or differently, by substitutents selected from the group of halogen, $(C_1-C_6)$-alkyl, $(C_2-C_6)$-alkenyl, $(C_3-C_8)$-cycloalkyl, hydroxy, oxo, carboxyl, $(C_1-C_6)$-alkoxycarbonyl, $(C_1-C_6)$-alkanoyl, $(C_3-C_8)$-cycloalkylcarbonyl, $(C_1-C_6)$-alkylsulfonyl, aminocarbonyl,

and $(C_1-C_6)$-alkylaminocarbonyl, where $(C_1-C_6)$-alkyl and $(C_1-C_6)$-alkanoyl in turn may each be substituted by halogen, hydroxy, $(C_1-C_4)$-alkoxy, $(C_1-C_4)$-alkoxycarbonyl, amino, mono- or di-$(C_1-C_4)$-alkylamino, $(C_1-C_4)$-alkoxycarbonylamino or 5- or 6-membered heterocyclyl having up to two heteroatoms from the series N, O and/or S, or R¹ is 5-membered heteroaryl which is linked via a ring nitrogen atom and has up to two further ring nitrogen atoms, and which may be substituted once to three times, identically or differently, by halogen, $(C_1-C_6)$-alkoxycarbonyl or $(C_1-C_6)$-alkyl which is in turn optionally substituted by hydroxy or halogen, R² is $(C_6-C_{10})$-aryl which may be substituted once or twice, identically differently, by substituents selected from the group of halogen, nitro, cyano, $(C_1-C_6)$-alkyl, trifluoromethyl, $(C_1-C_6)$-alkanoyl, $(C_1-C_6)$-alkoxy, hydroxy, $(C_1-C_6)$-acyloxy, amino, $(C_1-C_6)$-acylamino, mono- and di-[$(C_1-C_6)$-alkylsulfonyl]amino, where $(C_1-C_6)$-alkyl and $(C_1-C_6)$-alkoxy in turn may each be substituted by hydroxy, amino, $(C_1-C_4)$-alkoxy or $(C_1-C_4)$-acylamino, or R² is 5- or 6-membered heteroaryl which has up to two ring nitrogen atoms and which may be substituted by amino, hydroxy, halogen, $(C_1-C_6)$-alkyl or $(C_1-C_6)$-alkoxy, and R³ is hydrogen, halogen, $(C_1-C_6)$-alkyl, trifluoromethyl, nitro, cyano, carboxyl or $(C_1-C_6)$-alkoxycarbonyl, or a salt, solvate or solvate of a salt thereof.

2. The compound of the formula (I) as claimed in claim 1, in which

R¹ is a group of the formula in which

A is $CR^4R^5$, O, S, $NR^6$ or $—CH_2NR^6—$, where

R$^4$ and R$^5$ are independently of one another hydrogen, (C$_1$-C$_4$)-alkyl, which may be substituted by hydroxy, or hydroxy, fluorine, carboxyl or (C$_1$-C$_4$)-alkoxycarbonyl, or together with the carbon atom to which they are bonded form a carbonyl group, and R$^6$ is hydrogen, (C$_2$-C$_4$)-alkenyl, (C$_3$-C$_6$)-cycloalkyl, (C$_1$-C$_4$)-alkoxycarbonyl, formyl, acetyl, (C$_3$-C$_6$)-cycloalkylcarbonyl, (C$_1$-C$_4$)-alkylsulfonyl, aminocarbonyl, (C$_1$-C$_4$)-alkylaminocarbonyl or is (C$_1$-C$_4$)-alkyl which in turn may be substituted by hydroxy, methoxy, ethoxy, (C$_1$-C$_4$)-alkoxycarbonyl, amino, dimethylamino, diethylamino, pyrrolidino, piperidino or morpholino, or R$^1$ is 5-membered heteroaryl which is linked via a ring nitrogen atom and has up to two further ring nitrogen atoms and which may be substituted once or twice, identically or differently, by fluorine, chlorine, (C$_1$-C$_4$)-alkoxycarbonyl or (C$_1$-C$_4$)-alkyl which in turn is optionally substituted by hydroxy, R$^2$ is phenyl which may be substituted once or twice, identically or differently, by substituents selected from the group of fluorine, chlorine, cyano, (C$_1$-C$_4$)-alkyl, trifluoromethyl, formyl, acetyl, (C$_1$-C$_4$)-alkoxy, hydroxy, acetoxy, pivaloyloxy, amino, formylamino, acetylamino and methylsulfonylamino, where (C$_1$-C$_4$)-alkyl and (C$_1$-C$_4$)-alkoxy in turn may each be substituted by hydroxy, amino, methoxy, ethoxy or acetylamino, or R$^2$ is pyrrolyl, pyridyl or pyrimidinyl, each of which may be substituted by amino, fluorine, chlorine, methyl, ethyl, methoxy or ethoxy, and R$^3$ is hydrogen, fluorine, chlorine, bromine, methyl, ethyl, trifluoromethyl, nitro or cyano, or a salt, solvate or solvate of a salt thereof.

3. The compound of the formula (I) as claimed in claim 1, in which

R$^1$ is imidazolyl which is attached via a ring nitrogen atom or is piperazinyl which is attached via a ring nitrogen atom and which may be substituted on the second ring nitrogen atom by methyl, ethyl, 2-hydroxyethyl, 2-methoxyethyl, acetyl, tert-butoxycarbonyl or methylsulfonyl, R$^2$ is phenyl which may be substituted by fluorine or hydroxy in position 4 relative to the linkage point on the phenyl ring, and R$^3$ is located in position 4 relative to the linkage point of the pyridazinone ring and is hydrogen, fluorine, chlorine, methyl or trifluoromethyl, or a salt, solvate or solvate of a salt thereof.

4. The compound of the formula (I) as claimed in claim 1, wherein the compound has one of the following structures:

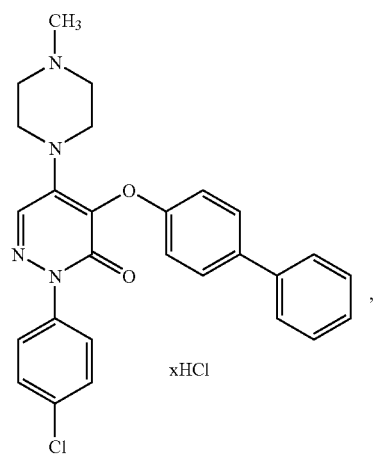

,

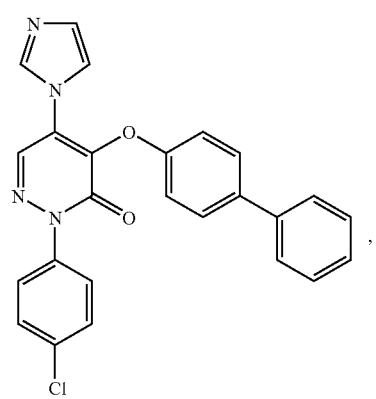

,

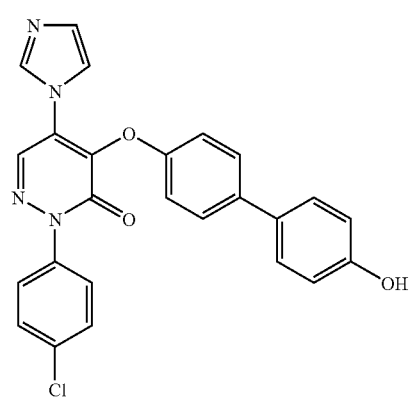

or a salt, solvate or solvate of a salt thereof.

5. A process for preparing the compounds of the formula (I) as defined in claim 1, wherein first a compound of the formula (II)

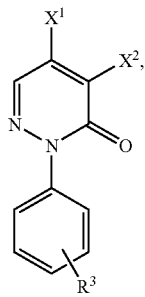
(II)

in which

R³ has the meaning indicated in claim 1, and

X¹ and X² are each halogen, is converted with a compound of the formula (III)

R¹—H  (III), in which R¹ has the meaning indicated in claim 1, into a compound of the formula (IV)

in which R¹, R³ and X² each have the meaning indicated above, and the latter is then reacted with a compound of the formula (V)

(V)

in which R² has the meaning indicated in claim 1.

6. A pharmaceutical composition comprising at least one compound of the formula (I) as defined in claim 1, and at least one further excipient.

* * * * *